US011649241B2

(12) United States Patent
Zak et al.

(10) Patent No.: US 11,649,241 B2
(45) Date of Patent: May 16, 2023

(54) PYRAZOLOCHLOROPHENYL COMPOUNDS, COMPOSITIONS AND METHODS OF USE THEREOF

(71) Applicant: Genentech, Inc., South San Francisco, CA (US)

(72) Inventors: Mark Zak, Davidsonville, MD (US); F. Anthony Romero, Redwood City, CA (US); Po-wai Yuen, Beijing (CN); Emily J. Hanan, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 17/174,733

(22) Filed: Feb. 12, 2021

(65) Prior Publication Data

US 2021/0179626 A1     Jun. 17, 2021

Related U.S. Application Data

(63) Continuation of application No. 16/561,447, filed on Sep. 5, 2019, now abandoned, which is a continuation of application No. PCT/EP2018/056129, filed on Mar. 13, 2018.

(30) Foreign Application Priority Data

Mar. 14, 2017    (WO) ................ PCT/CN2017/076598

(51) Int. Cl.
| | | |
|---|---|---|
| C07D 487/04 | (2006.01) | |
| C07D 471/04 | (2006.01) | |
| C07D 491/048 | (2006.01) | |
| C07D 498/04 | (2006.01) | |
| C07D 513/04 | (2006.01) | |

(52) U.S. Cl.
CPC ......... *C07D 487/04* (2013.01); *C07D 471/04* (2013.01); *C07D 491/048* (2013.01); *C07D 498/04* (2013.01); *C07D 513/04* (2013.01)

(58) Field of Classification Search
CPC ................ C07D 487/04; C07D 471/04; C07D 491/048; C07D 498/04; C07D 513/04
See application file for complete search history.

(56) References Cited

U.S. PATENT DOCUMENTS 9,346,815 B2    5/2016    Zak et al.

FOREIGN PATENT DOCUMENTS

| JP | 2007-516194 A | 6/2007 |
|---|---|---|
| JP | 2012-532112 A | 12/2012 |
| JP | 2016-535772 A | 11/2016 |
| WO | 2005/002552 A2 | 1/2005 |
| WO | 2005/002552 A3 | 1/2005 |
| WO | 2006/070202 A1 | 7/2006 |
| WO | 2011/003065 A2 | 1/2011 |
| WO | 2015/068856 A1 | 5/2015 |
| WO | 2015/177326 A1 | 11/2015 |
| WO | 2017/140825 A1 | 8/2017 |

OTHER PUBLICATIONS

GVK BIO et al., CAS Registry Database, 1348439-69-9, (CAS Registry No. 1348366-33-5; Registry No. 1348342-66-4; Registry No. 1348042-57-8; Registry No. 1347970-24-4; Registry No. 1347873-72-6; 2,1-Benzisoxazole-3-carboxamide, N-[3-[5-(2,2-difluoroethyl)-4,5,6,7-tetrahydro-3-H-imidazo[4,5-c]pyridin-2-yl]-1H-pyrazol-4-yl]), pp. 1-4; Submission Date Dec. 4, 2011.
GVK BIO et al., CAS Registry Database, 1349237-47-3, (C19 H18 F N7 O2; 2,1-Benzisoxazole-3-carboxamide, N-[3-[5-(2-fluoroethyl)-4,5,6,7-tetrahydro-3H-imidazo{4,5-c]pyridin-2-yl]-1H-pyrazol-4-yl]), pp. 1-2; Submission Date Dec. 5, 2011.
Hanan, E., et al., "Discovery of Potent and Selective Pyrazolopyrimidine Janus Kinase 2 Inhibitors" J Med Chem 55(22):10090-10107 (Nov. 26, 2012).
International Preliminary Report on Patentability—PCT/EP2018/056129 dated Sep. 17, 2019.
International Search Report for PCT/EP2018/056129 dated Jan. 4, 2019.
Ukrorgsyntez, Limited, CAS Registry Database, 1825504-02-6, (C18 H16 N6 O2; Imidazo [1,2-b]pyridazine-3-carboxamide, 6-methoxy-2-methyl-N-(3-phenyl-1H-pyrazol-4-yl)), pp. 1; Submission Date Dec. 9, 2015.
Ukrorgsyntez, Limtied et al., CAS Registry Database, 1935725-26-0, (C17 H12 F N5 O; 1H-Benzimidazole-6-carboxamide, N-[3-(2-fluorophenyl)-1H-pyrazol-4-yl]), pp. 1; Submission Date Jun. 20, 2016.

*Primary Examiner* — Rebecca L Anderson
(74) *Attorney, Agent, or Firm* — Robert C. Hall

(57) ABSTRACT

Compounds of Formula I and methods of use as Janus kinase inhibitors are described herein.

4 Claims, No Drawings

PYRAZOLOCHLOROPHENYL COMPOUNDS, COMPOSITIONS AND METHODS OF USE THEREOF

CROSS-REFERENCE TO RELATED APPLICATION

This application is a continuation of U.S. application Ser. No. 16/561,447 filed on Sep. 5, 2019, which is a continuation of International Application No. PCT/EP2018/056129 filed on Mar. 13, 2018, which claims the benefit of priority to International Application No. PCT/CN2017/076598, filed Mar. 14, 2017, the disclosures of which are incorporated herein by reference.

FIELD OF THE INVENTION

The field of the invention pertains to compounds of Formula I, and subformulas thereof, which are inhibitors of a Janus kinase, such as JAK1, as well as compositions containing these compounds, and methods of use including, but not limited to, diagnosis or treatment of patients suffering from a condition responsive to the inhibition of a JAK kinase.

BACKGROUND OF INVENTION

Cytokine pathways mediate a broad range of biological functions, including many aspects of inflammation and immunity. Janus kinases (JAK), including JAK1, JAK2, JAK3 and TYK2, are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets (Schindler et al., 2007, J. Biol. Chem. 282: 20059-63). JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence. Exemplary therapeutic benefits of the inhibition of JAK enzymes are discussed, for example, in International Application No. WO 2013/014567.

JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFN-gamma), and IL-2 and IL-6 cytokine receptor complexes (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). JAK1 knockout mice die perinatally due to defects in LIF receptor signaling (Kisseleva et al., 2002, Gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4 and IL-6 pathways. A humanized monoclonal antibody targeting the IL-6 pathway (Tocilizumab) was approved by the European Commission for the treatment of moderate-to-severe rheumatoid arthritis (Scheinecker et al., 2009, Nat. Rev. Drug Discov. 8:273-274).

CD4 T cells play an important role in asthma pathogenesis through the production of TH2 cytokines within the lung, including IL-4, IL-9 and IL-13 (Cohn et al., 2004, Amur Rev. Immunol. 22:789-815). IL-4 and IL-13 induce increased mucus production, recruitment of eosinophils to the lung, and increased production of IgE (Kasaian et al., 2008, Biochem. Pharmacol. 76(2): 147-155). IL-9 leads to mast cell activation, which exacerbates the asthma symptoms (Kearley et al., 2011, Am. J. Resp. Crit. Care Med., 183(7): 865-875). The IL-4Rα chain activates JAK1 and binds to either IL-4 or IL-13 when combined with the common gamma chain or the IL-13Rα1 chain respectively (Pemis et al., 2002, J. Clin. Invest. 109(10): 1279-1283). The common gamma chain can also combine with IL-9Rα to bind to IL-9, and IL-9Rα activates JAK1 as well (Demoulin et al., 1996, Mol. Cell Biol. 16(9):4710-4716). While the common gamma chain activates JAK3, it has been shown that JAK1 is dominant over JAK3, and inhibition of JAK1 is sufficient to inactivate signaling through the common gamma chain despite JAK3 activity (Haan et al., 2011, Chem. Biol. 18(3):314-323). Inhibition of IL-4, IL-13 and IL-9 signaling by blocking the JAK/STAT signaling pathway can alleviate asthmatic symptoms in pre-clinical lung inflammation models (Mathew et al., 2001, J. Exp. Med. 193(9): 1087-1096; Kudlacz et. al., 2008, Eur. J. Pharmacol. 582(1-3): 154-161).

Biochemical and genetic studies have shown an association between JAK2 and single-chain (e.g., EPO), IL-3 and interferon gamma cytokine receptor families (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). Consistent with this, JAK2 knockout mice die of anemia (O'Shea et al., 2002, Cell, 109 (suppl.): S121-S131). Kinase activating mutations in JAK2 (e.g., JAK2 V617F) are associated with myeloproliferative disorders in humans.

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID) (O'Shea et al., 2002, Cell, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, Arthritis & Rheumatism 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, Gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and IL-23 cytokines (Ustekinumab) was recently approved by the European Commission for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

There exists a need in the art for additional or alternative treatments of conditions mediated by JAK kinases, such as those described above.

SUMMARY OF INVENTION

One aspect of the invention includes a compound of Formula (I):

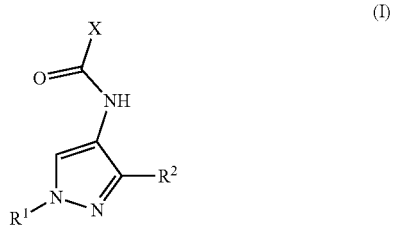

or a salt thereof, wherein:

$R^1$ is $C_2$-$C_6$alkenyl, $C_2$-$C_6$alkynyl, —($C_0$-$C_3$alkyl)CN, —($C_0$-$C_3$alkyl)$OR^a$, —($C_0$-$C_3$alkyl)$R^a$, —($C_0$-$C_3$alkyl)$SR^a$, —($C_0$-$C_3$alkyl)$NR^aR^b$, —($C_0$-$C_3$alkyl)$OCF_3$, —($C_0$-$C_3$alkyl)$CF_3$, —($C_0$-$C_3$alkyl)$NO_2$, —($C_0$-$C_3$alkyl)C(O)$R^a$, —($C_0$-$C_3$alkyl)C(O)$OR^a$, —($C_0$-$C_3$alkyl)C(O)$NR^aR^b$, —($C_0$-$C_3$alkyl)$NR^aC(O)R^b$, —($C_0$-$C_3$alkyl)S(O)$_{1-2}R^a$, —($C_0$-$C_3$alkyl)$NR^aS(O)_{1-2}R^b$, —($C_0$-$C_3$alkyl)S(O)$_{1-2}NR^aR^b$, —($C_0$-$C_3$alkyl)(5-6-membered heteroaryl) or —($C_0$-$C_3$alkyl)phenyl, wherein $R^1$ is optionally substituted by halogen, $C_1$-$C_3$alkyl, oxo, —$CF_3$, —($C_0$-$C_3$alkyl)$OR^c$ or —($C_0$-$C_3$alkyl)$NR^cR^d$;

each $R^a$ is independently selected from the group consisting of hydrogen, $C_1$-$C_6$alkyl, $C_3$-$C_6$ cycloalkyl, 3-10 membered heterocyclyl, 5-6 membered heteroaryl, —C(O)$R^c$, —C(O)$OR^c$, —C(O)$NR^cR^d$, —$NR^cC(O)R^d$, —S(O)$_{1-2}R^c$, —$NR^cS(O)_{1-2}R^d$ and —S(O)$_{1-2}$ $NR^cR^d$, wherein any $C_3$-$C_6$ cycloalkyl, 3-10 membered heterocyclyl, and 5-6 membered heteroaryl of $R^a$ is optionally substituted with $R^e$;

each $R^b$ is independently selected from the group consisting of hydrogen and $C_1$-$C_3$alkyl, wherein said alkyl is optionally substituted by halogen or oxo;

each $R^c$ and $R^d$ is independently selected from the group consisting of hydrogen, 3-6 membered heterocyclyl, $C_3$-$C_6$ cycloalkyl, and $C_1$-$C_3$alkyl, wherein any 3-6 membered heterocyclyl, $C_3$-$C_6$ cycloalkyl, and $C_1$-$C_3$alkyl of $R^c$ and $R^d$ is optionally substituted by halogen or oxo; or $R^c$ and $R^d$ are taken together with the atom to which they are attached to form a 3-6-membered heterocyclyl, optionally substituted by halogen, oxo, —$CF_3$ or $C_1$-$C_3$alkyl;

each $R^e$ is independently selected from the group consisting of oxo, $OR^f$, $NR^fR^g$, halogen, 3-10 membered heterocyclyl, $C_3$-$C_6$ cycloalkyl, and $C_1$-$C_6$alkyl, wherein any $C_3$-$C_6$ cycloalkyl and $C_1$-$C_6$alkyl of $R^e$ is optionally substituted by $OR^f$, $NR^fR^g$, halogen, 3-10 membered heterocyclyl, oxo, or cyano, and wherein any 3-10 membered heterocyclyl of $R^e$ is optionally substituted by halogen, oxo, cyano, —$CF_3$, $NR^hR^k$, 3-6 membered heterocyclyl, or $C_1$-$C_3$alkyl that is optionally substituted by halogen, oxo, $OR^f$, or $NR^hR^k$;

each $R^f$ and $R^g$ is independently selected from the group consisting of hydrogen, $C_1$-$C_6$alkyl. 3-6 membered heterocyclyl, and $C_3$-$C_6$ cycloalkyl, wherein any $C_1$-$C_6$alkyl. 3-6 membered heterocyclyl, and $C_3$-$C_6$ cycloalkyl of $R^f$ and $R^g$ is optionally substituted by $R^m$;

each $R^h$ and $R^k$ is independently selected from the group consisting of hydrogen and $C_1$-$C_6$alkyl that is optionally substituted by halogen, cyano, 3-6 membered heterocyclyl, or oxo; or $R^h$ and $R^k$ are taken together with the atom to which they are attached to form a 3-6-membered heterocyclyl that is optionally substituted by halogen, cyano, oxo, —$CF_3$ or $C_1$-$C_3$alkyl that is optionally substituted by halogen or oxo;

each $R^m$ is independently selected from the group consisting of halogen, cyano, oxo, $C_3$-$C_6$cycloalkyl, hydroxy, and $NR^hR^k$, wherein any $C_3$-$C_6$cycloalkyl of $R^m$ is optionally substituted with halogen, oxo, cyano, or $C_1$-$C_3$alkyl;

$R^2$ is phenyl, 5-6 membered heteroaryl, $C_3$-$C_6$ cycloalkyl or 3-10 membered heterocyclyl, wherein $R^2$ is optionally substituted by 1-5 $R^n$;

each $R^n$ is independently selected from the group consisting of $C_1$-$C_6$, alkyl, $C_2$-$C_6$ alkenyl, $C_2$-$C_6$ alkynyl, oxo, halogen, —($C_0$-$C_3$ alkyl)CN, —($C_0$-$C_3$ alkyl)$OR^o$, —($C_0$-$C_3$ alkyl)$SR^o$, —($C_0$-$C_3$ alkyl)$NR^oR^p$, —($C_0$-$C_3$ alkyl)$OCF_3$, —($C_0$-$C_3$ alkyl)$CF_3$, —($C_0$-$C_3$ alkyl)$NO_2$, —($C_0$-$C_3$ alkyl)C(O)$R^o$, —($C_0$-$C_3$ alkyl)C(O)$OR^o$, —($C_0$-$C_3$ alkyl)C(O)$NR^oR^p$, —($C_0$-$C_3$ alkyl)$NR^oC(O)R^p$, —($C_0$-$C_3$ alkyl)S(O)$_{1-2}R^o$, —($C_0$-$C_3$ alkyl)$NR^oS(O)_{1-2}R^p$, —($C_0$-$C_3$ alkyl)S(O)$_{1-2}NR^oR^p$, —($C_0$-$C_3$ alkyl)($C_3$-$C_6$ cycloalkyl), —($C_0$-$C_3$ alkyl)(3-6-membered heterocyclyl), —($C_0$-$C_3$ alkyl)C(O)(3-6-membered heterocyclyl), —($C_0$-$C_3$ alkyl)(5-6-membered heteroaryl) and —($C_0$-$C_3$ alkyl)phenyl, wherein each $R^n$ is independently optionally substituted with halogen, $C_1$-$C_3$ alkyl, oxo, —$CF_3$, —($C_0$-$C_3$ alkyl)$OR^r$ or —($C_0$-$C_3$ alkyl)$NR^rR^s$; or two $R^n$ are taken together to form —O($CH_2$)$_{1-3}$O—;

each $R^o$ is independently selected from the group consisting of hydrogen, $C_1$-$C_6$, alkyl, $C_3$-$C_6$ cycloalkyl, 3-6 membered heterocyclyl, —C(O)$R^r$, —C(O)$OR^r$, —C(O)$NR^rR^s$, —$NR^rC(O)R^s$, —S(O)$_{1-2}R^r$, —$NR^rS(O)_{1-2}R^s$ and —S(O)$_{1-2}NR^rR^s$, wherein said alkyl, cycloalkyl and heterocyclyl are independently optionally substituted by oxo, $C_1$-$C_3$ alkyl, $OR^r$, $NR^rR^s$ or halogen; and each $R^p$ is independently selected from the group consisting of hydrogen and $C_1$-$C_3$ alkyl, wherein said alkyl is independently optionally substituted by halogen or oxo; or $R^o$ and $R^p$ are taken together with the atom to which they are attached to form a 3-6-membered heterocyclyl, optionally substituted by halogen, oxo, —$CF_3$ or $C_1$-$C_3$ alkyl;

each $R^r$ and $R^s$ is independently selected from the group consisting of hydrogen and $C_1$-$C_3$ alkyl optionally substituted by halogen or oxo; or $R^r$ and $R^s$ are taken together with the atom to which they are attached to form a 3-6-membered heterocyclyl, optionally substituted by halogen, oxo, —$CF_3$ or $C_1$-$C_3$ alkyl; and X is a 9-10 membered bicyclic heteroaryl that comprises 2 or 3 atoms each independently selected from the group consisting of O, S, and N, wherein the 9-10 membered bicyclic heteroaryl is optionally substituted with $R^u$; provided X is not,

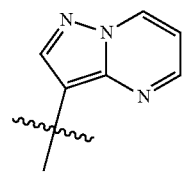 [SMILES: *c1cnn2cccnc12]

optionally substituted with $R^u$;

each $R^u$ is independently selected from the group consisting of hydrogen, halo, $C_1$-$C_6$ alkyl, $C_3$-$C_6$ cycloalkyl, 3-6 membered heterocyclyl, —$OR^v$, —C(O)$R^v$, —C(O)$OR^v$, —C(O)NR$^v$R$^w$, —NR$^v$R$^w$, —NR$^v$C(O)R$^w$, —S(O)$_{1-2}$R$^v$, —NR$^v$S(O)$_{1-2}$R$^w$ and —S(O)$_{1-2}$NR$^v$R$^w$, wherein said alkyl, cycloalkyl and heterocyclyl are independently optionally substituted by oxo, C$_1$-C$_3$ alkyl, —OR$^v$, —NR$^v$R$^w$ or halogen; and each R$^v$ and R$^w$ is independently selected from the group consisting of hydrogen and C$_1$-C$_3$ alkyl optionally substituted by halogen or oxo; or R$^v$ and R$^w$ are taken together with the atom to which they are attached to form a 3-6-membered heterocyclyl, optionally substituted by halogen, oxo, —CF$_3$ or C$_1$-C$_3$ alkyl.

Also provided is a pharmaceutical composition that comprises a compound of the invention and a pharmaceutically acceptable carrier, diluent or excipient.

Another aspect includes a compound of the invention for use in therapy, such as the treatment of an inflammatory disease or cancer.

Another aspect includes a method of preventing, treating or lessening the severity of a disease or condition responsive to the inhibition of a Janus kinase, such as JAK1 kinase, in a patient. The method can comprise administering to the patient a therapeutically effective amount of a compound of the invention.

Another aspect includes the use of a compound of the invention in the manufacture of a medicament for the treatment of a disease responsive to the inhibition of a Janus kinase, such as JAK1 kinase.

Another aspect includes a kit for treating a disease or disorder responsive to the inhibition of a Janus kinase, such as JAK1 kinase. The kit can comprise a first pharmaceutical composition comprising a compound of the invention, and instructions for use.

Certain compounds of the invention possess beneficial potency as inhibitors of one or more Janus kinase (e.g. JAK1). Certain compounds are also, a) selective for one Janus kinase over other kinases, b) selective for JAK1 over other Janus kinases, and/or c) possess other properties (e.g. melting point, pK, solubility, etc.) necessary for formulation and administration by inhalation. Certain compounds of formula (I) may be particularly useful for treating conditions such as asthma.

DETAILED DESCRIPTION OF THE INVENTION

Definitions

"Halogen" or "halo" refers to F, Cl, Br or I. Additionally, terms such as "haloalkyl," are meant to include monohaloalkyl and polyhaloalkyl.

The term "alkyl" refers to a saturated linear or branched-chain monovalent hydrocarbon radical, wherein the alkyl radical may be optionally substituted. In one example, the alkyl radical is one to eighteen carbon atoms (C$_1$-C$_{18}$). In other examples, the alkyl radical is C$_0$-C$_6$, C$_0$-C$_5$, C$_0$-C$_3$, C$_1$-C$_{12}$, C$_1$-C$_{10}$, C$_1$-C$_8$, C$_1$-C$_6$, C$_1$-C$_5$, C$_1$-C$_4$, or C$_1$-C$_3$. C$_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl and 1-octyl. In some embodiments, substituents for "optionally substituted alkyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl and heterocyclic portions thereof may be optionally substituted, such as by one to four instances of substituents selected from this same list.

The term "alkenyl" refers to linear or branched-chain monovalent hydrocarbon radical with at least one site of unsaturation, i.e., a carbon-carbon double bond, wherein the alkenyl radical may be optionally substituted, and includes radicals having "cis" and "trans" orientations, or alternatively, "E" and "Z" orientations. In one example, the alkenyl radical is two to eighteen carbon atoms (C$_2$-C$_{18}$). In other examples, the alkenyl radical is C$_2$-C$_{12}$, C$_2$-C$_{10}$, C$_2$-C$_8$, C$_2$-C$_6$ or C$_2$-C$_3$. Examples include, but are not limited to, ethenyl or vinyl (—CH=CH$_2$), prop-1-enyl (—CH=CHCH$_3$), prop-2-enyl (—CH$_2$CH=CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl. In some embodiments, substituents for "optionally substituted alkenyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl and heterocyclic portions thereof may be optionally substituted, such as by one to four instances of substituents selected from this same list.

The term "alkynyl" refers to a linear or branched monovalent hydrocarbon radical with at least one site of unsaturation, i.e., a carbon-carbon, triple bond, wherein the alkynyl radical may be optionally substituted. In one example, the alkynyl radical is two to eighteen carbon atoms (C$_2$-C$_{18}$). In other examples, the alkynyl radical is C$_2$-C$_{12}$, C$_2$-C$_{10}$, C$_2$-C$_8$, C$_2$-C$_6$ or C$_2$-C$_3$. Examples include, but are not limited to, ethynyl (—C≡CH), prop-1-ynyl (—C≡CCH$_3$), prop-2-ynyl (propargyl, —CH$_2$C≡CH), but-1-ynyl, but-2-ynyl and but-3-ynyl. In some embodiments, substituents for "optionally substituted alkynyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl and heterocyclic portions thereof may be optionally substituted, such as by one to four instances of substituents selected from this same list.

"Alkylene" refers to a saturated, branched or straight chain hydrocarbon group having two monovalent radical centers derived by the removal of two hydrogen atoms from the same or two different carbon atoms of a parent alkane. In one example, the divalent alkylene group is one to eighteen carbon atoms ($C_1$-$C_{18}$). In other examples, the divalent alkylene group is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. The group $C_0$ alkylene refers to a bond. Example alkylene groups include methylene (—$CH_2$—), 1,1-ethyl (—$CH(CH_3)$—), (1,2-ethyl (—$CH_2CH_2$—), 1,1-propyl (—$CH(CH_2CH_3)$—), 2,2-propyl (—$C(CH_3)_2$—), 1,2-propyl (—$CH(CH_3)CH_2$—), 1,3-propyl (—$CH_2CH_2CH_2$—), 1,1-dimethyleth-1,2-yl (—$C(CH_3)_2CH_2$—), 1,4-butyl (—$CH_2CH_2CH_2CH_2$—), and the like.

The term "heteroalkyl" refers to a straight or branched chain monovalent hydrocarbon radical, consisting of the stated number of carbon atoms, or, if none are stated, up to 18 carbon atoms, and from one to five heteroatoms selected from the group consisting of O, N, Si and S, and wherein the nitrogen and sulfur atoms can optionally be oxidized and the nitrogen heteroatom can optionally be quaternized. In some embodiments, the heteroatom is selected from O, N and S, wherein the nitrogen and sulfur atoms can optionally be oxidized and the nitrogen heteroatom can optionally be quaternized. The heteroatom(s) can be placed at any interior position of the heteroalkyl group, including the position at which the alkyl group is attached to the remainder of the molecule (e.g., —O—$CH_2$—$CH_3$). Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S(O)$_2$—$CH_3$, —Si($CH_3$)$_3$ and —$CH_2$—CH=N—$OCH_3$. Up to two heteroatoms can be consecutive, such as, for example, —$CH_2$—NH—$OCH_3$ and —$CH_2$—O—Si($CH_3$)$_3$. Heteroalkyl groups can be optionally substituted. In some embodiments, substituents for "optionally substituted heteroalkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

"Amino" means primary (i.e., —$NH_2$), secondary (i.e., —NRH), tertiary (i.e., —NRR) and quaternary (i.e., —N(+)RRR) amines, that are optionally substituted, in which each R is the same or different and selected from alkyl, cycloalkyl, aryl, and heterocyclyl, wherein the alkyl, cycloalkyl, aryl and heterocyclyl groups are as defined herein. Particular secondary and tertiary amines are alkylamine, dialkylamine, arylamine, diarylamine, aralkylamine and diaralkylamine, wherein the alkyl and aryl portions can be optionally substituted. Particular secondary and tertiary amines are methylamine, ethylamine, propylamine, isopropylamine, phenylamine, benzylamine, dimethylamine, diethylamine, dipropylamine and diisopropylamine. In some embodiments, R groups of a quaternary amine are each independently optionally substituted alkyl groups.

"Aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl. Substituted phenyl or substituted aryl means a phenyl group or aryl group substituted with one, two, three, four or five substituents, for example, 1-2, 1-3 or 1-4 substituents, such as chosen from groups specified herein (see "optionally substituted" definition), such as F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2,4-difluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl) phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, 2-chloro-5-difluoromethoxy and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. In some embodiments, a substituent of an aryl, such as phenyl, comprises an amide. For example, an aryl (e.g., phenyl) substituent may be —$(CH_2)_{0-4}$CONR'R", wherein R' and R" each independently refer to groups including, for example, hydrogen; unsubstituted $C_1$-$C_6$ alkyl; $C_1$-$C_6$, alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$, heteroalkyl substituted by halogen, OH, CN, unsubstituted $C_1$-$C_6$ alkyl, unsubstituted $C_1$-$C_6$, alkoxy, oxo or NR'R"; unsubstituted $C_6$-$C_{10}$ aryl; $C_6$-$C_{10}$ aryl substituted by halogen, OH, CN, unsubstituted $C_1$-$C_6$, alkyl, unsubstituted $C_1$-$C_6$, alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$, alkyl, unsubstituted $C_1$-$C_6$, alkoxy, oxo or NR'R"; or R' and R" can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$, alkyl, unsubstituted $C_1$-$C_6$, alkoxy, oxo or NR'R".

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane. In some embodiments, substituents for "optionally substituted cycloalkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, isopropyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list. In some embodiments, a substituent of a cycloalkyl comprises an amide. For example, a cycloalkyl substituent may be —$(CH_2)_{0-4}$CONR'R", wherein R' and R" each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R"; or R' and R" can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R".

"Heterocyclic group", "heterocyclic", "heterocycle", "heterocyclyl", or "heterocyclo" are used interchangeably and refer to any mono-, bi-, tricyclic or spiro, saturated or unsaturated, aromatic (heteroaryl) or non-aromatic (e.g., heterocycloalkyl), ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles, e.g., 5-6 membered heteroaryl. In another example, heterocyclyl includes 3-11 membered heterocycloyalkyls, such as 4-11 membered heterocycloalkyls. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]-hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo

[2.2.2]hexanyl, 2-azabicyclo-[3.2.1]octanyl, 8-azabicyclo[3.2.1]octanyl, 2-azabicyclo[2.2.2]octanyl, 8-azabicyclo-[2.2.2]octanyl, 7-oxabicyclo[2.2.1]heptane, azaspiro[3.5]nonanyl, azaspiro[2.5]-octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list. In some embodiments, a substituent of a heterocyclic group, such as a heteroaryl or heterocycloalkyl, comprises an amide. For example, a heterocyclic (e.g., heteroaryl or heterocycloalkyl) substituent may be —$(CH_2)_{0-4}CONR'R''$, wherein R' and R'' each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R''; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R''; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R''; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R''; or R' and R'' can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$, alkoxy, oxo or NR'R''.

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) 13th ed. Table 7-2 [1985], Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list. In some embodiments, a substituent of a heteroaryl comprises an amide. For example, a heteroaryl substituent may be —$(CH_2)_{0-4}CONR'R''$, wherein R' and R'' each independently refer to groups including, for example, hydrogen; unsubstituted $C_1$-$C_6$ alkyl; $C_1$-$C_6$ alkyl substituted by halogen, OH, CN, unsubstituted $C_1$-$C_6$, alkyl, unsubstituted $C_1$-$C_6$ alkoxy, oxo or NR'R''; unsubstituted $C_1$-$C_6$, heteroalkyl; Ci-G, heteroalkyl substituted by halogen, OH, CN, unsubstituted $C_1$-$C_6$ alkyl, unsubstituted $C_1$-$C_6$ alkoxy, oxo or NR'R''; unsubstituted $C_6$-$C_{10}$ aryl; $C_6$-$C_{10}$ aryl substituted by halogen, OH, CN, unsubstituted $C_1$-$C_6$, alkyl, unsubstituted $C_1$-$C_6$, alkoxy, or NR'R''; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R''; or R' and R'' can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$, alkoxy, oxo or NR'R''.

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "alkoxy" refers to a linear or branched monovalent radical represented by the formula —OR in which R is alkyl, as defined herein. Alkoxy groups include methoxy, ethoxy, propoxy, isopropoxy, mono-, di- and tri-fluoromethoxy and cyclopropoxy.

"Acyl" means a carbonyl containing substituent represented by the formula —C(O)—R in which R is hydrogen, alkyl, cycloalkyl, aryl or heterocyclyl, wherein the alkyl, cycloalkyl, aryl and heterocyclyl are as defined herein. Acyl groups include alkanoyl (e.g., acetyl), aroyl (e.g., benzoyl), and heteroaroyl (e.g., pyridinoyl).

"Optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

Optional substituents for alkyl radicals, alone or as part of another substituent (e.g., alkoxy), as well as alkylenyl, alkenyl, alkynyl, heteroalkyl, heterocycloalkyl, and cycloalkyl, also each alone or as part of another substituent, can be a variety of groups, such as those described herein, as well as selected from the group consisting of halogen; oxo; CN; NO; $N_3$; —OR'; perfluoro-$C_1$-$C_4$ alkoxy; unsubstituted $C_3$-$C_7$ cycloalkyl; $C_3$-$C_7$ cycloalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl (e.g., phenyl); $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R"; —NR'R"; —SR'; —SiR'R"R'''; —OC(O)R'; —C(O)R'; —$CO_2$R'; —CONR'R"; —OC(O)NR'R"; —NR"C(O)R'; —NR'''C(O)NR'R"; —NR"C(O)$_2$R'; —S(O)$_2$R'; —S(O)$_2$NR'R"; —NR'S(O)$_2$R"; —NR''' S(O)$_2$NR'R"; amidinyl; guanidinyl; —(CH$_2$)$_{1-4}$—OR'; —(CH$_2$)$_{14}$—NR'R"; —(CH$_2$)$_{1-4}$—SR'; —(CH$_2$)$_{1-4}$—SiR'R"R'''; —(CH$_2$)$_{1-4}$—OC(O)R'; —(CH$_2$)$_{1-4}$—C(O)R'; —(CH$_2$)$_{1-4}$—$CO_2$R'; and —(CH$_2$)$_{1-4}$CONR'R", or combinations thereof, in a number ranging from zero to (2m'+1), where m' is the total number of carbon atoms in such radical.

R', R" and R''' each independently refer to groups including, for example, hydrogen; unsubstituted $C_1$-$C_6$, alkyl; $C_1$-$C_6$ alkyl substituted by halogen, OH, CN, unsubstituted $C_1$-$C_6$, alkyl, unsubstituted $C_1$-$C_6$, alkoxy, oxo or NR'R"; unsubstituted $C_1$-$C_6$, heteroalkyl; $C_1$-$C_6$ heteroalkyl substituted by halogen, OH, CN, unsubstituted $C_1$-$C_6$, alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$, alkyl, unsubstituted $C_1$-$C_6$, alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$, alkyl, unsubstituted $C_1$-$C_6$, alkoxy, oxo or NR'R". When R' and R" are attached to the same nitrogen atom, they can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$, alkyl, unsubstituted $C_1$-$C_6$, alkoxy, oxo or NR'R". For example, —NR'R" is meant to include 1-pyrrolidinyl and 4-morpholinyl.

Similarly, optional substituents for the aryl and heteroaryl groups are varied. In some embodiments, substituents for aryl and heteroaryl groups are selected from the group consisting of halogen; CN; NO; $N_3$; —OR'; perfluoro-$C_1$-$C_6$ alkoxy; unsubstituted $C_3$-$C_7$ cycloalkyl; $C_3$-$C_7$ cycloalkyl substituted by halogen, OH, CN, unsubstituted $C_1$-$C_6$, alkyl, unsubstituted $C_1$-$C_6$, alkoxy, oxo or NR'R"; unsubstituted $C_6$-$C_{10}$ aryl (e.g., phenyl); $C_6$-$C_{10}$ aryl substituted by halogen, OH, CN, unsubstituted $C_1$-$C_6$, alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$, alkoxy, oxo or NR'R"; —NR'R"; —SR'; —SiR'R"R'''; —OC(O)R'; —C(O)R'; —$CO_2$R'; —CONR'R"; —OC(O)NR'R"; —NR"C(O)R'; —NR'''C(O)NR'R"; —NR"C(O)$_2$R'; —S(O)$_2$R'; —S(O)$_2$NR'R"; —NR'S(O)$_2$R"; —NR'' 'S(O)$_2$NR'R"; amidinyl; guanidinyl; —(CH$_2$)$_{1-4}$—OR'; —(CH$_2$)$_{1-4}$—NR'R"; —(CH$_2$)$_{1-4}$—SR'; —(CH$_2$)$_{1-4}$—SiR'R"R'''; —(CH$_2$)$_{1-4}$—OC(O)R'; —(CH$_2$)$_{1-4}$—C(O)R'; —(CH$_2$)$_{1-4}$—$CO_2$R'; and —(CH$_2$)$_{1-4}$ CONR'R", or combinations thereof, in a number ranging from zero to (2m'+1), where m' is the total number of carbon atoms in such radical. R', R" and R''' each independently refer to groups including, for example, hydrogen; unsubstituted $C_1$-$C_6$ alkyl; $C_1$-$C_6$, alkyl substituted by halogen, OH, CN, unsubstituted $C_1$-$C_6$, alkyl, unsubstituted $C_1$-$C_6$, alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R". When R' and R" are attached to the same nitrogen atom, they can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R". For example, —NR'R" is meant to include 1-pyrrolidinyl and 4-morpholinyl.

The term "oxo" refers to =O or (=O)$_2$.

As used herein a wavy line "〰" that intersects a bond in a chemical structure indicate the point of attachment of the atom to which the wavy bond is connected in the chemical structure to the remainder of a molecule, or to the remainder of a fragment of a molecule. In some embodiments, an arrow together with an asterisk is used in the manner of a wavy line to indicate a point of attachment.

In certain embodiments, divalent groups are described genetically without specific bonding configurations. It is understood that the generic description is meant to include both bonding configurations, unless specified otherwise. For example, in the group $R^1$-$R^2$-$R^3$ if the group $R^2$ is described as —CH$_2$C(O)—, then it is understood that this group can be bonded both as $R^1$—CH$_2$C(O)—$R^3$, and as $R^1$—C(O)CH$_2$—$R^3$, unless specified otherwise.

The phrase "pharmaceutically acceptable" refers to molecular entities and compositions that do not produce an adverse, allergic or other untoward reaction when administered to an animal, such as, for example, a human, as appropriate.

Compounds of the present invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-10-sulphonate, for example (1S)-(+)-10-camphorsulfonic acid salt), glutamate, glutarate, hippurate (2-(benzoylamino)acetate), orotate, xylate (p-xylene-2-sulphonate), and pamoic (2,2'-dihydroxy-1,1'-dinaphthylmethane-3,3'-dicarboxylate).

A "sterile" formulation is aseptic or free from all living microorganisms and their spores.

"Stereoisomers" refer to compounds that have identical chemical constitution, but differ with regard to the arrangement of the atoms or groups in space. Stereoisomers include diastereomers, enantiomers, conformers and the like.

"Chiral" refers to molecules which have the property of non-superimposability of the mirror image partner, while the term "achiral" refers to molecules which are superimposable on their mirror image partner.

"Diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds of the present invention can exist in unsolvated forms as well as solvated forms, including hydrated forms. A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the present invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}$C or $^{3}$H) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-Methoxybenzyl), Boc (tert-Butyloxycarbonyl), Fmoc (9-Fluorenylmethyloxycarbonyl) and Cbz (Carbobenzyloxy). Further examples of these groups are found in T. W. Greene and P. G. M. Wuts, "Protecting Groups in Organic Synthesis, 3$^{rd}$ ed., John Wiley & Sons, Inc., 1999. The term "protected amino" refers to an amino group substituted with one of the above amino-protecting groups.

"Carboxy-protecting group" as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4''-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl) methylsilyl)ethyl, p-toluenesulfonylethyl, 4-nitrobenzylsulfonylethyl, allyl, cinnamyl, 1-(trimethylsilylmethyl) prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, 3$^{rd}$ ed., John Wiley & Sons, Inc., 1999. The term "protected carboxy" refers to a carboxy group substituted with one of the above carboxy-protecting groups.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g., TBS, TBDPS) groups. Further examples of these groups are found in T. W. Greene and P. G. M. Wuts, "Protecting Groups in Organic Synthesis, 3$^{rd}$ ed., John Wiley & Sons, Inc., 1999. The term "protected hydroxy" refers to a hydroxy group substituted with one of the above hydroxy-protecting groups.

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of Formula I, or a compound of Table 1 or of Examples 1-15, to a patient, the patient is typically in need thereof.

The term "Janus kinase" refers to JAK1, JAK2, JAK3 and TYK2 protein kinases. In some embodiments, a Janus kinase may be further defined as one of JAK1, JAK2, JAK3 or TYK2. In any embodiment, any one of JAK1, JAK2, JAK3 and TYK2 may be specifically excluded as a Janus kinase. In some embodiments, a Janus kinase is JAK1. In some embodiments, a Janus kinase is a combination of JAK1 and JAK2.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., JAK1 activity) compared to normal.

In some embodiments, a compound of Formula I, or a compound of Table 1 or of Examples 1-15, is selective for inhibition of JAK1 over JAK3 and TYK2. In some embodiments, a compound of Formula I, or a compound of Table 1 or of Examples 1-15, is selective for inhibition of JAK1 over JAK2, JAK3, or TYK2, or any combination of JAK2, JAK3, or TYK2. In some embodiments, a compound of Formula I, or a compound of Table 1 or of Examples 1-15, is selective for inhibition of JAK1 and JAK2 over JAK3 and TYK2. In some embodiments, a compound of Formula I, or a compound of Table 1 or of Examples 1-15, is selective for inhibition of JAK1 over JAK3. By "selective for inhibition" it is meant that the compound is at least a 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, better inhibitor of a particular Janus kinase (e.g., JAK1) activity compared to another particular Janus kinase (e.g., JAK1) activity, or is at least a 2-, 3-, 4-, 5-, 10-, 25-, 50-, 100-, 250-, or 500-fold better inhibitor of a particular Janus kinase (e.g., JAK1) activity compared to another particular Janus kinase (e.g., JAK1) activity.

"Therapeutically effective amount" means an amount of a compound of the present invention, such as a compound of Formula I, or a compound of Table 1 or of Examples 1-15, that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In some embodiments, the therapeutically effective amount is an amount sufficient to decrease or alleviate the symptoms of an autoimmune or inflammatory disease (e.g., asthma). In some embodiments, a therapeutically effective amount is an amount of a chemical entity described herein sufficient to significantly decrease the activity or number of B-cells. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, such as a compound of Formula I, or a compound of Table 1 or of Examples 1-15, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

"Inflammatory disorder" refers to any disease, disorder or syndrome in which an excessive or unregulated inflammatory response leads to excessive inflammatory symptoms, host tissue damage, or loss of tissue function. "Inflammatory disorder" also refers to a pathological state mediated by influx of leukocytes or neutrophil chemotaxis.

"Inflammation" refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune responses to foreign antigens, and autoimmune responses. Accordingly, inflammatory disorders amenable to treatment with a compound of the present invention, such as a compound of Formula I, or a compound of Table 1 or of Examples 1-15, encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity responses mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" refers to any group of disorders in which tissue injury is associated with humoral or cell-mediated responses to the body's own constituents. Non-limiting examples of autoimmune diseases include rheumatoid arthritis, lupus and multiple sclerosis.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In some embodiments, inflammatory disorders which can be treated according to the methods of this invention include, but are not limited to, asthma, rhinitis (e.g., allergic rhinitis), allergic airway syndrome, atopic dermatitis, bronchitis, rheumatoid arthritis, psoriasis, contact dermatitis, chronic obstructive pulmonary disease and delayed hypersensitivity reactions.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

"Package insert" is used to refer to instructions customarily included in commercial packages of therapeutic products that contain information about the indications, usage, dosage, administration, contraindications or warnings concerning the use of such therapeutic products.

The terms "compound(s) of this invention," and "compound(s) of the present invention" and the like, unless otherwise indicated, include compounds of Formula I, or a compound of Table 1 or of Examples 1-15, and stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

Unless otherwise stated, structures depicted herein are also meant to include compounds that differ only in the presence of one or more isotopically enriched atoms. Exemplary isotopes that can be incorporated into compounds of the present invention, such as a compound of Formula I, or a compound of Table 1 or of Examples 1-15, include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds of Formula I, or a compound of Table 1 or of Examples 1-15, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

The use of the term "or" is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

Inhibitors of Janus Kinases

Also provided is a compound selected from Examples 1-15 and the compounds in Table 1, or any combination thereof.

TABLE 1

Exemplary Compounds of the Present Invention

| Example No. | Product Structure | Chemical Name | m/z |
|---|---|---|---|
| 1 | | N-(3-(5-Chloro-2-methoxyphenyl)-1-methyl-H-pyrazol-4-yl)-2-methyl-2H-pyrazolo[4,3-c]pyridine-7-carboxamide | 396.8 |
| 2 | | N-(3-(5-Chloro-2-methoxyphenyl)-1-methyl-1H-pyrazol-4-yl)-H-pyrazolo[4,3-c]pyridine-7-carboxamide | 382.8 |
| 3 | | N-(3-(5-Chloro-2-methoxyphenyl)-1H-pyrazol-4-yl)thiazolo[5,4-c]pyridine-7-carboxamide | 386.0 |
| 4 | | N-(3-(5-chloro-2-(difluoromethoxy)phenyl)-1H-pyrazol-4-yl)thiazolo[5,4-c]pyridine-7-carboxamide | 422.0 |

TABLE 1-continued

Exemplary Compounds of the Present Invention

| Example No. | Product Structure | Chemical Name | m/z |
|---|---|---|---|
| 5 | 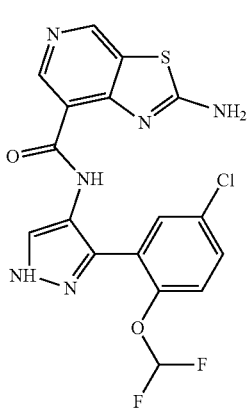 [SMILES: Nc1nc2c(C(=O)Nc3c[nH]nc3-c3cc(Cl)ccc3OC(F)F)cncc2s1] | 2-amino-N-(3-(5-chloro-2-(difluoromethoxy)phenyl)-1H-pyrazol-4-yl)thiazolo[5,4-c]pyridine-7-carboxamide | 437.1 |
| 6 | 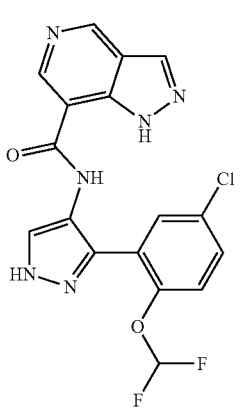 [SMILES: O=C(Nc1c[nH]nc1-c1cc(Cl)ccc1OC(F)F)c1cncc2cn[nH]c12] | N-(3-(5-chloro-2-(difluoromethoxy)phenyl)-1H-pyrazol-4-yl)-1H-pyrazolo[4,3-c]pyridine-7-carboxamide | 405.0 |
| 7 | 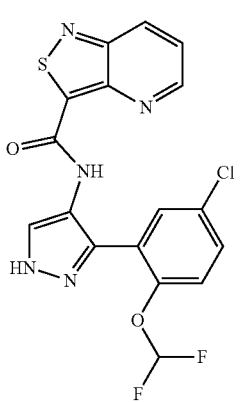 [SMILES: O=C(Nc1c[nH]nc1-c1cc(Cl)ccc1OC(F)F)c1snc2cccnc12] | N-(3-(5-chloro-2-(difluoromethoxy)phenyl)-1H-pyrazol-4-yl)isothiazolo[4,3-b]pyridine-3-carboxamide | 422.0 |

TABLE 1-continued

Exemplary Compounds of the Present Invention

| Example No. | Product Structure | Chemical Name | m/z |
|---|---|---|---|
| 8 | | N-(3-(5-chloro-2-(difluoromethoxy)phenyl)-1H-pyrazol-4-yl)-5H-pyrrolo[2,3-b]pyrazine-2-carboxamide | 405.1 |
| 9 | | 2-amino-N-(3-(5-chloro-2-(difluoromethoxy)phenyl)-1H-pyrazol-4-yl)pyrazolo[1,5-a]pyrimidine-3-carboxamide | 420.0 |
| 10 | | N-(3-(5-chloro-2-(difluoromethoxy)phenyl)-1H-pyrazol-4-yl)furo[3,2-c]pyridine-7-carboxamide | 405.1 |

TABLE 1-continued

Exemplary Compounds of the Present Invention

| Example No. | Product Structure | Chemical Name | m/z |
|---|---|---|---|
| 11 | | N-(3-(5-chloro-2-(difluoromethoxy)phenyl)-1H-pyrazol-4-yl)furo[3,2-b]pyridine-3-carboxamide | 405.1 |
| 12 | | N-(3-(5-chloro-2-(difluoromethoxy)phenyl)-1H-pyrazol-4-yl)-6-fluoropyrazolo[1,5-a]pyrimidine-3-carboxamide | LC 310114139 |
| 13 | | N-(3-(5-chloro-2-(difluoromethoxy)phenyl)-1H-pyrazol-4-yl)-5-methylpyrazolo[1,5-a]pyrimidine-3-carboxamide | 419.0 |

TABLE 1-continued

Exemplary Compounds of the Present Invention

| Example No. | Product Structure | Chemical Name | m/z |
|---|---|---|---|
| 14 | | N-(3-(5-chloro-2-(difluoromethoxy)phenyl)-1H-pyrazol-4-yl)-5-methoxypyrazolo[1,5-a]pyrimidine-3-carboxamide | 435.0 |
| 15 | | N-(3-(5-chloro-2-(difluoromethoxy)phenyl)-1H-pyrazol-4-yl)-3H-imidazo[4,5-c]pyridine-7-carboxamide | 405.1 |
| 16 | | N-(3-(5-chloro-2-(difluoromethoxy)phenyl)-1H-pyrazol-4-yl)isoxazolo[4,3-b]pyridine-3-carboxamide | |
| 17 | | N-(3-(5-chloro-2-(difluoromethoxy)phenyl)-1H-pyrazol-4-yl)imidazo[1,2-c]pyrimidine-8-carboxamide | |

TABLE 1-continued

Exemplary Compounds of the Present Invention

| Example No. | Product Structure | Chemical Name | m/z |
|---|---|---|---|
| 18 | | N-(3-(5-chloro-2-(difluoromethoxy)phenyl)-1H-pyrazol-4-yl)-1,3-dihydrofuro[3,4-c]pyridine-7-carboxamide | |
| 19 | | N-(3-(5-chloro-2-(difluoromethoxy)phenyl)-1H-pyrazol-4-yl)-1H-pyrrolo[2,3-c]pyridine-4-carboxamide | |
| 20 | | N-(3-(5-chloro-2-(difluoromethoxy)phenyl)-1H-pyrazol-4-yl)pyrazolo[1,5-a]pyrazine-7-carboxamide | |

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds of the present invention, such as a compound of Formula I, or a compound of Table 1 or of Examples 1-15, including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, an alkylcarbonyl (—CO—R) group, an alkoxycarbonyl (—CO—OR), or an acyloxyalkyl-alkoxycarbonyl (—CO—O—R—O—CO—R) group where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of Formula I or a subformula thereof. Prodrugs may be prepared by reacting a compound of the present invention, such as a compound of Formula I, or a compound of Table 1 or of Examples 1-15, with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention, such as a compound of Formula I, or a compound of Table 1 or of Examples 1-15, can be derivatized as an amide or alkyl ester. As another example, compounds of the present invention comprising free hydroxy groups can be derivatized as prodrugs by converting the hydroxy group into a group such as, but not limited to, a phosphate ester, hemi succinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1\text{-}C_6)$alkanoyloxymethyl, 1-(($C_1\text{-}C_6$)alkanoyloxy)ethyl, 1-methyl-1-(($C_1\text{-}C_6$)alkanoyl-oxy)ethyl, ($C_1\text{-}C_6$)alkoxycarbonyloxymethyl, N—($C_1\text{-}C_6$)alkoxycarbonylaminomethyl, succinoyl, ($C_1\text{-}C_6$)alkanoyl, alpha-amino($C_1\text{-}C_4$)alkanoyl, arylacyl and alpha-aminoacyl, or alpha-aminoacyl-alpha-aminoacyl, where each alpha-aminoacyl group is independently selected from the naturally occurring L-amino acids, P(O)(OH)$_2$, —P(O)(O($C_1\text{-}C_6$)alkyl)$_2$ or glycosyl (the radical resulting from the removal of a hydroxyl group of the hemiacetal form of a carbohydrate).

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

In one embodiment $R^1$ is —($C_0$-$C_3$alkyl)NR$^a$R$^b$, or a salt thereof.

In one embodiment $R^1$ is H or —($C_0$-$C_3$alkyl)R$^a$, or a salt thereof.

In one embodiment $R^1$ is —($C_0$-$C_3$alkyl)C(O)R$^a$, or a salt thereof.

In one embodiment $R^1$ is selected from the group consisting of H, methyl,

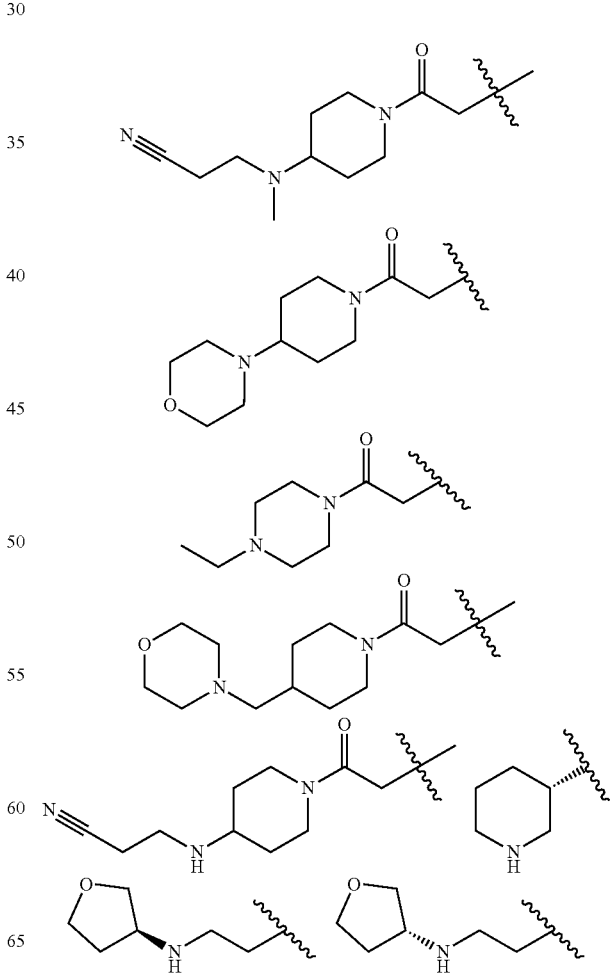

US 11,649,241 B2
37
-continued
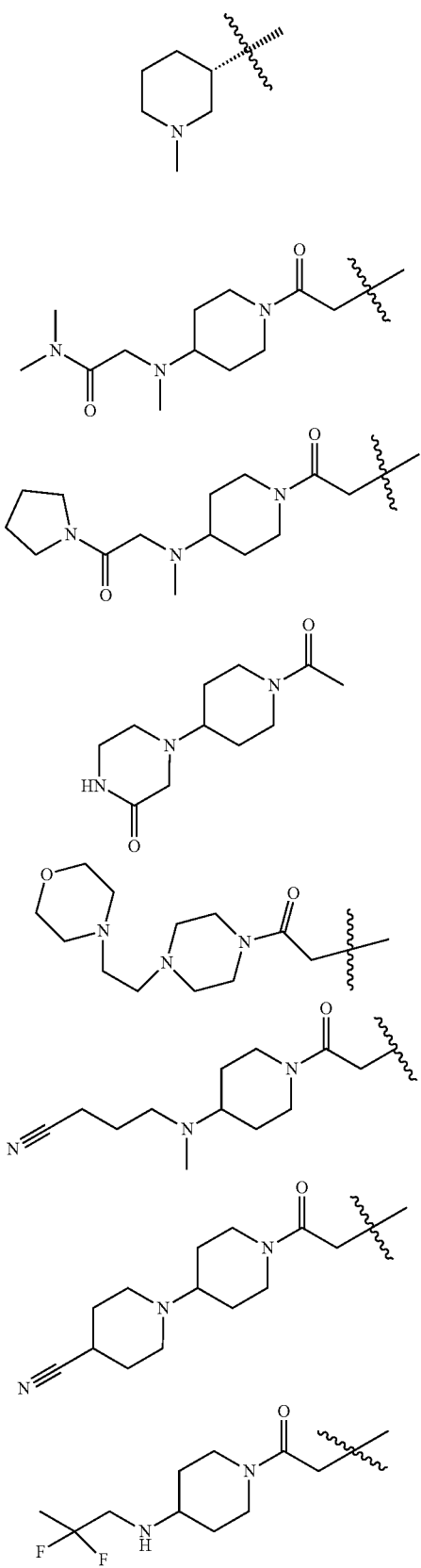
38
-continued
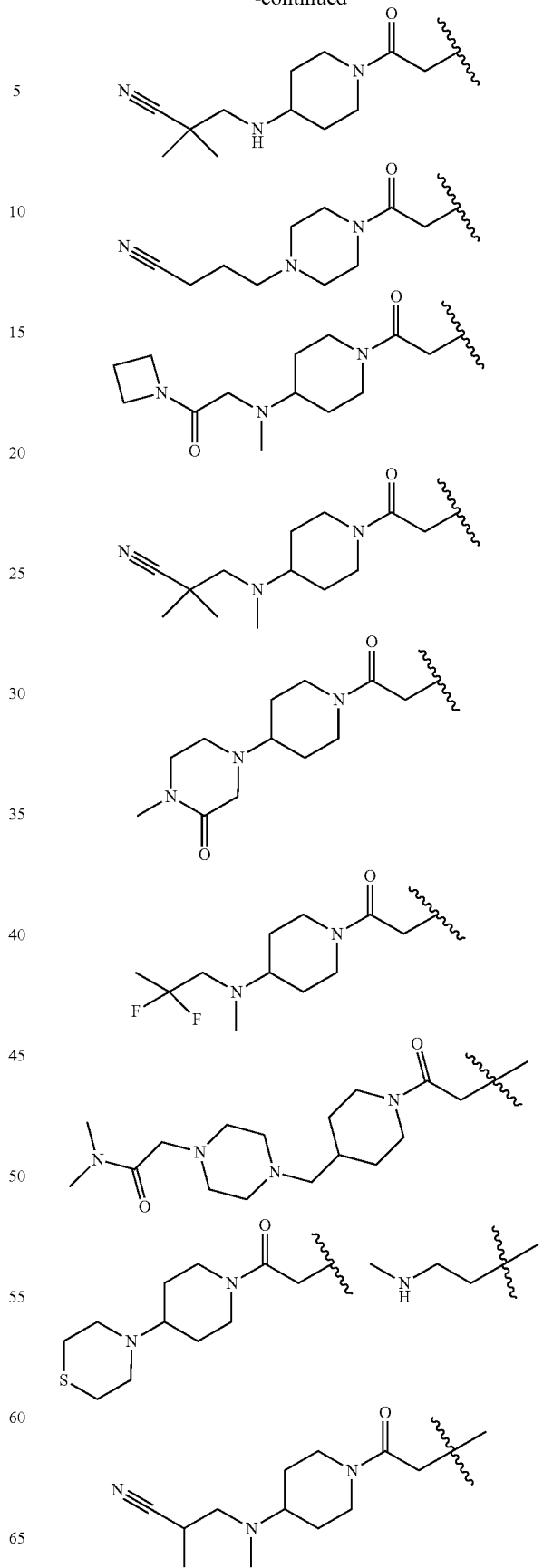

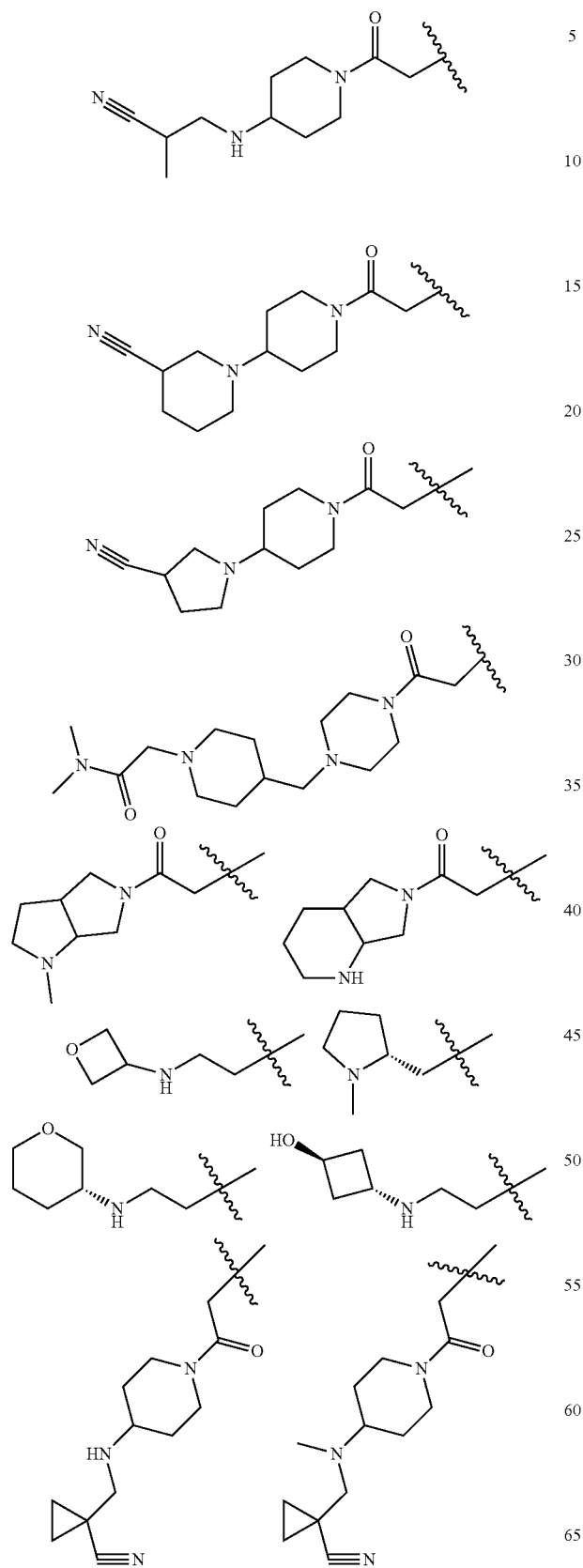
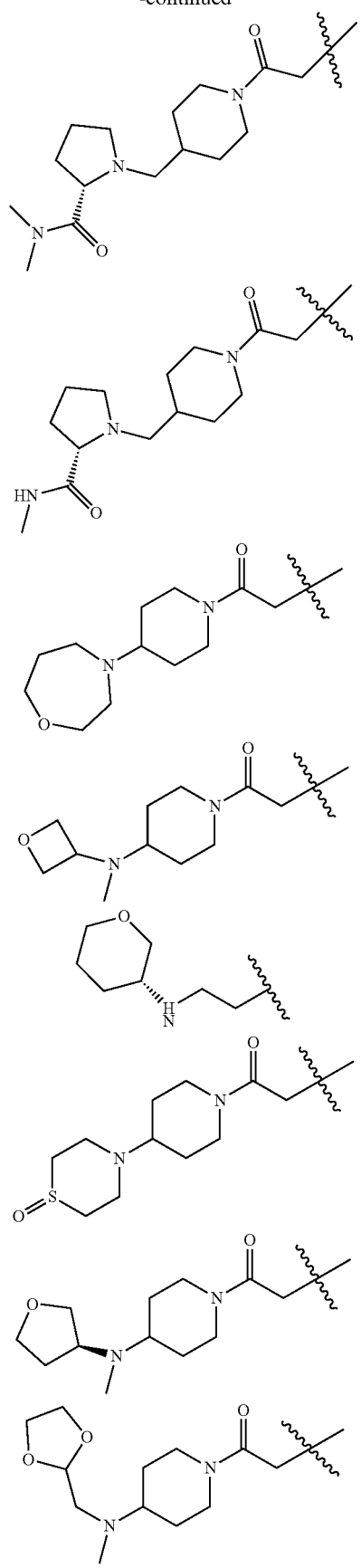

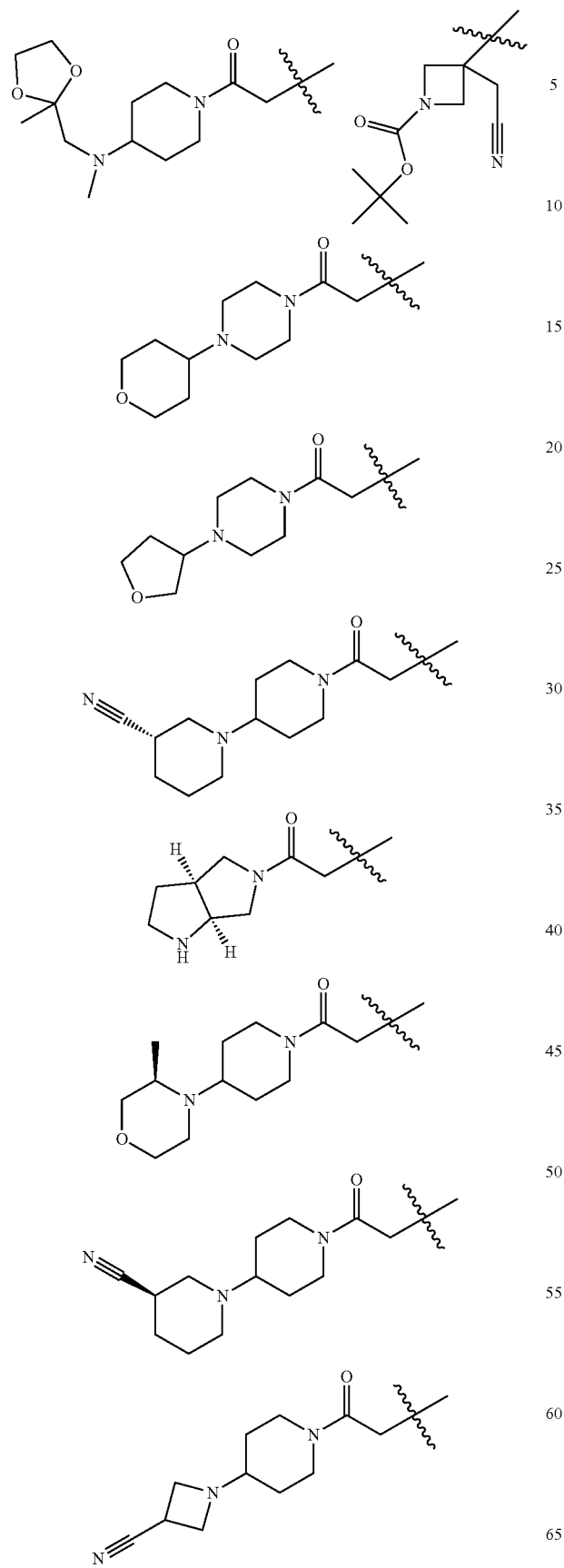
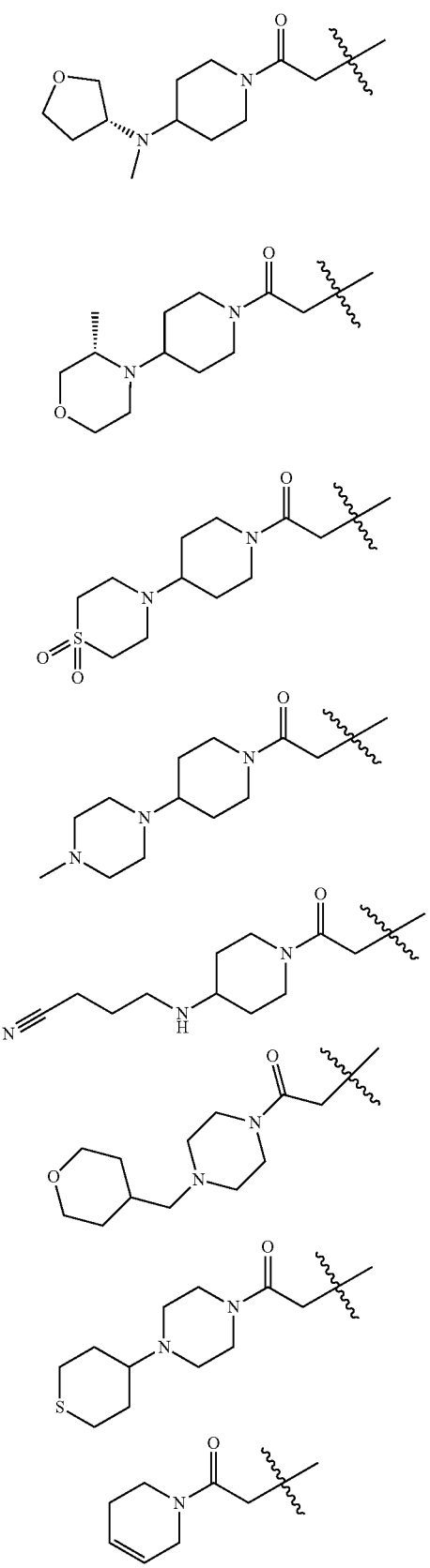

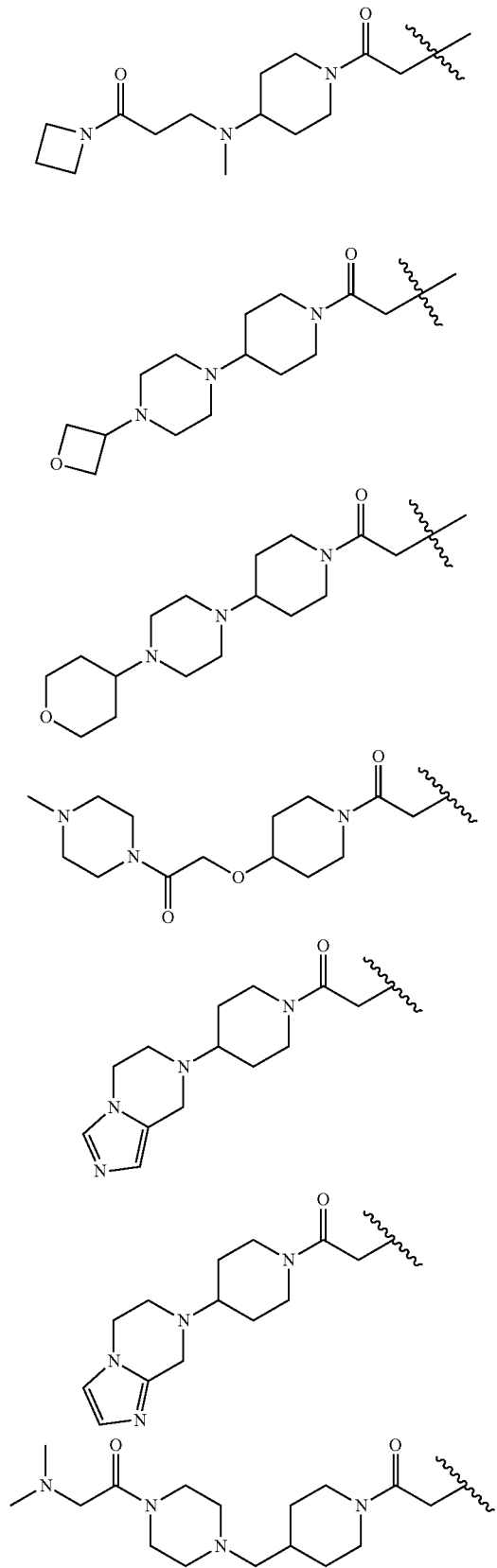
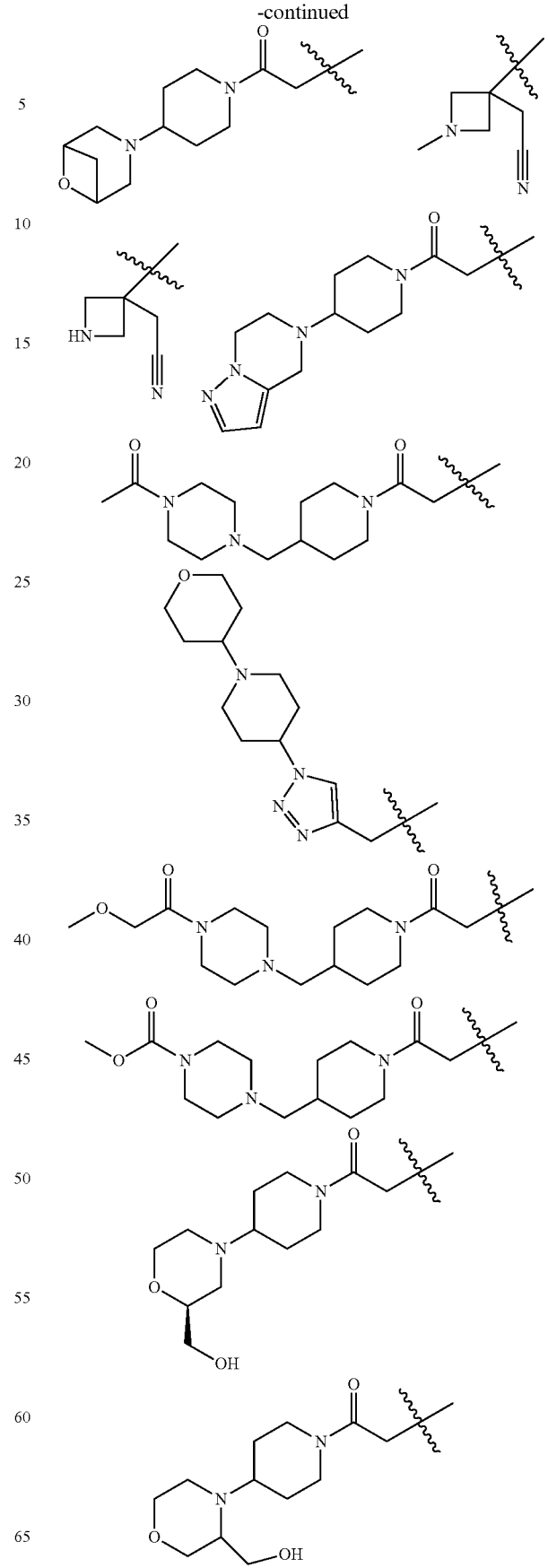

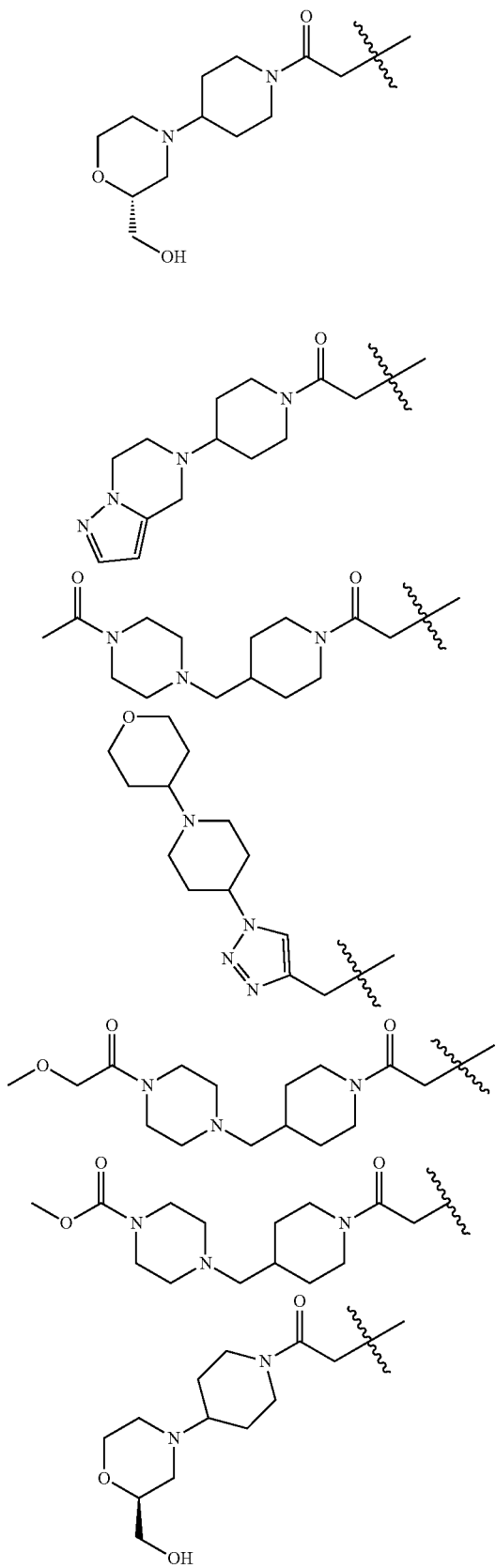
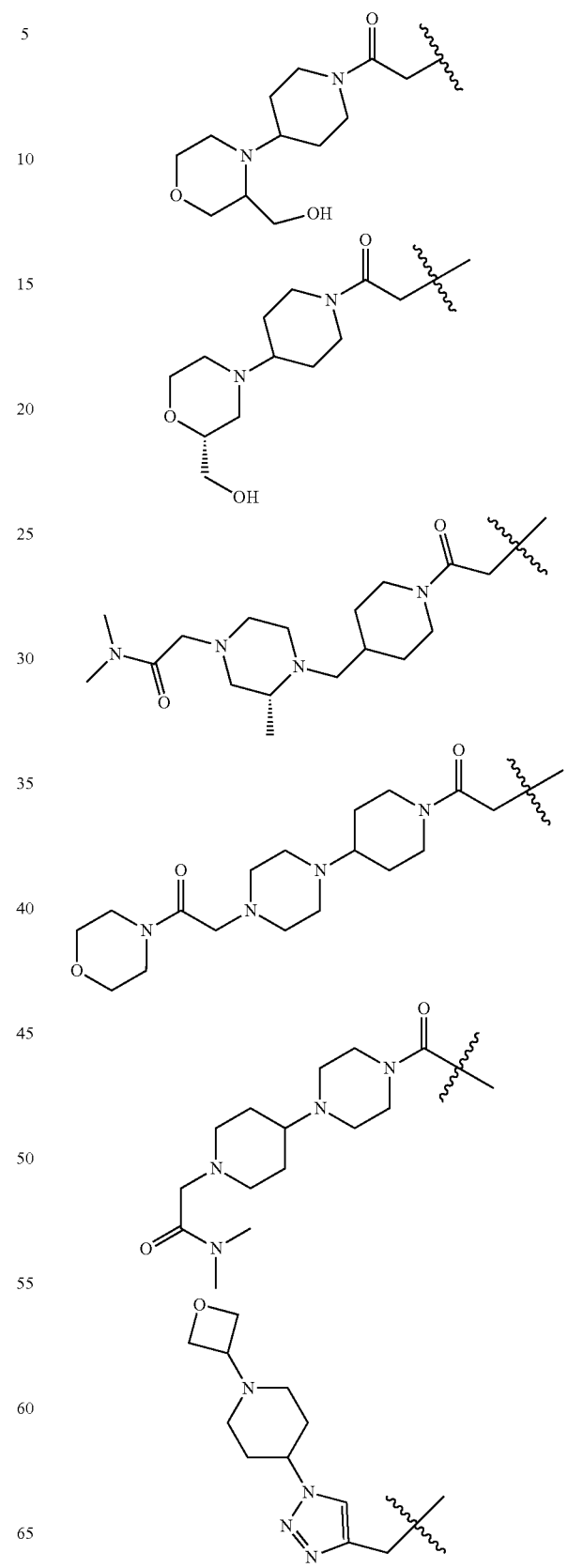

47
-continued
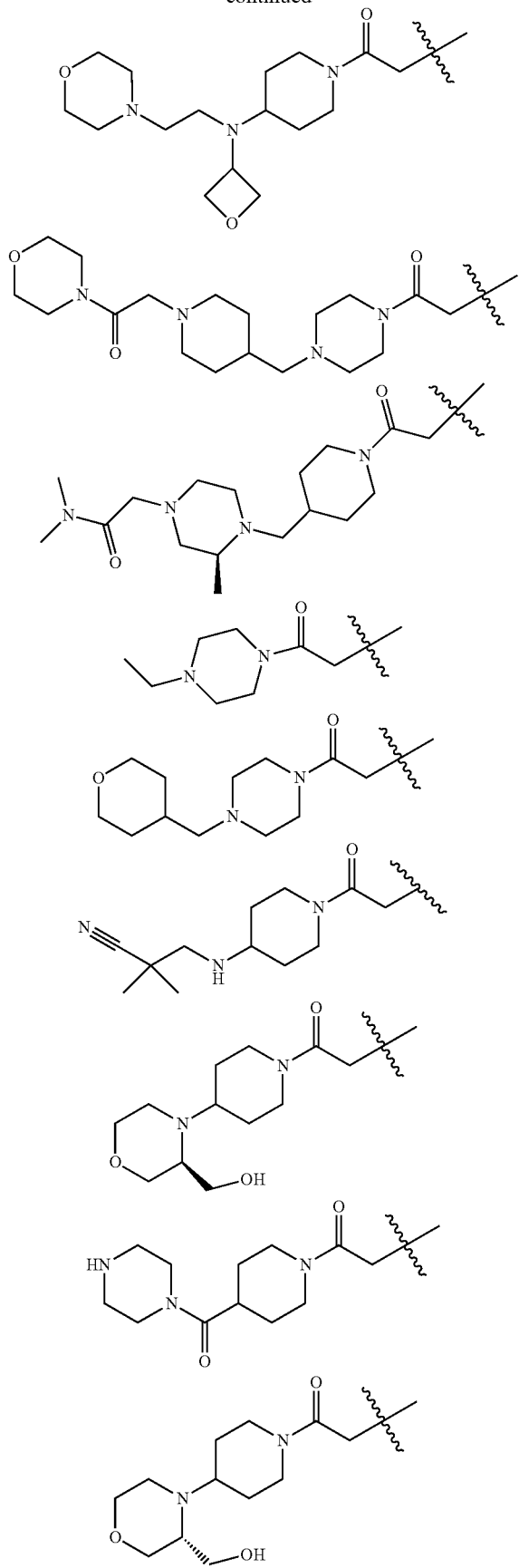
48
-continued
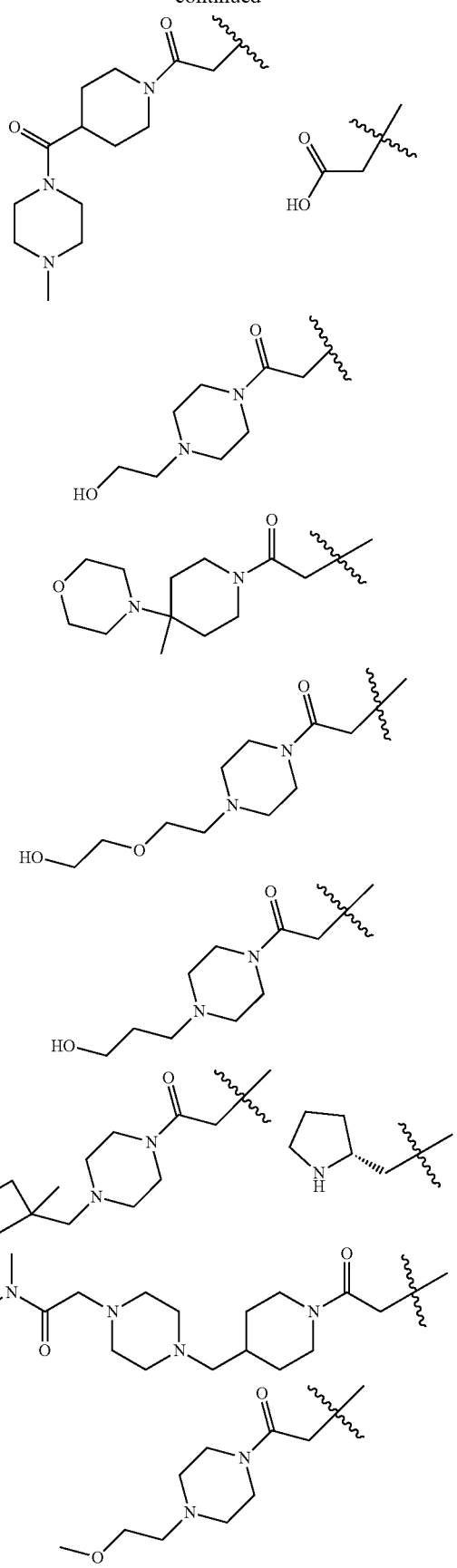

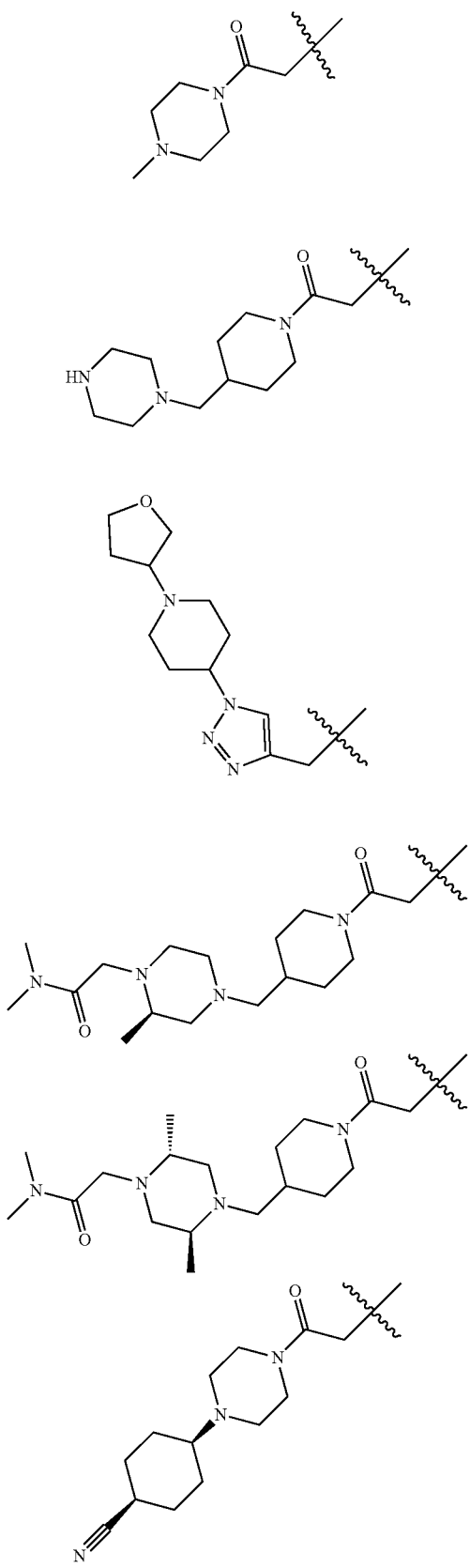
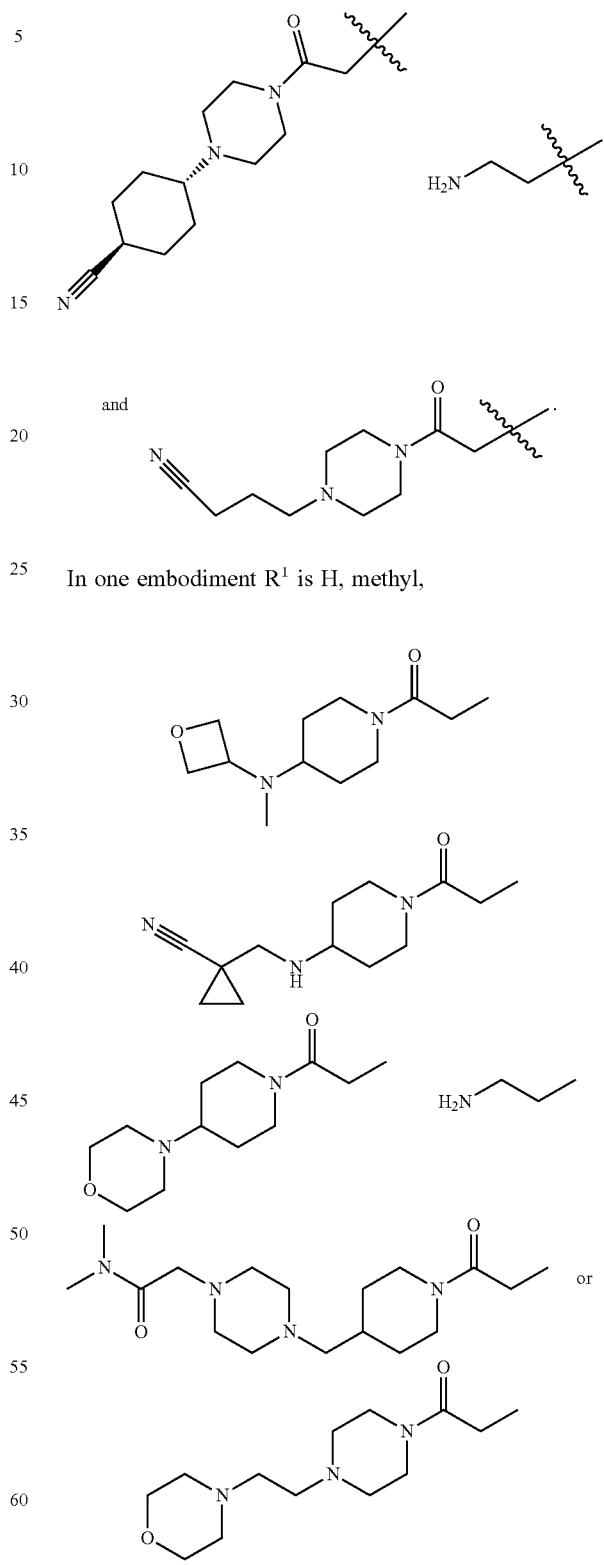
In one embodiment $R^1$ is H, methyl,
In one embodiment $R^1$ is H or methyl.
In one embodiment $R^e$ is selected from the group consisting of methyl, ethyl,

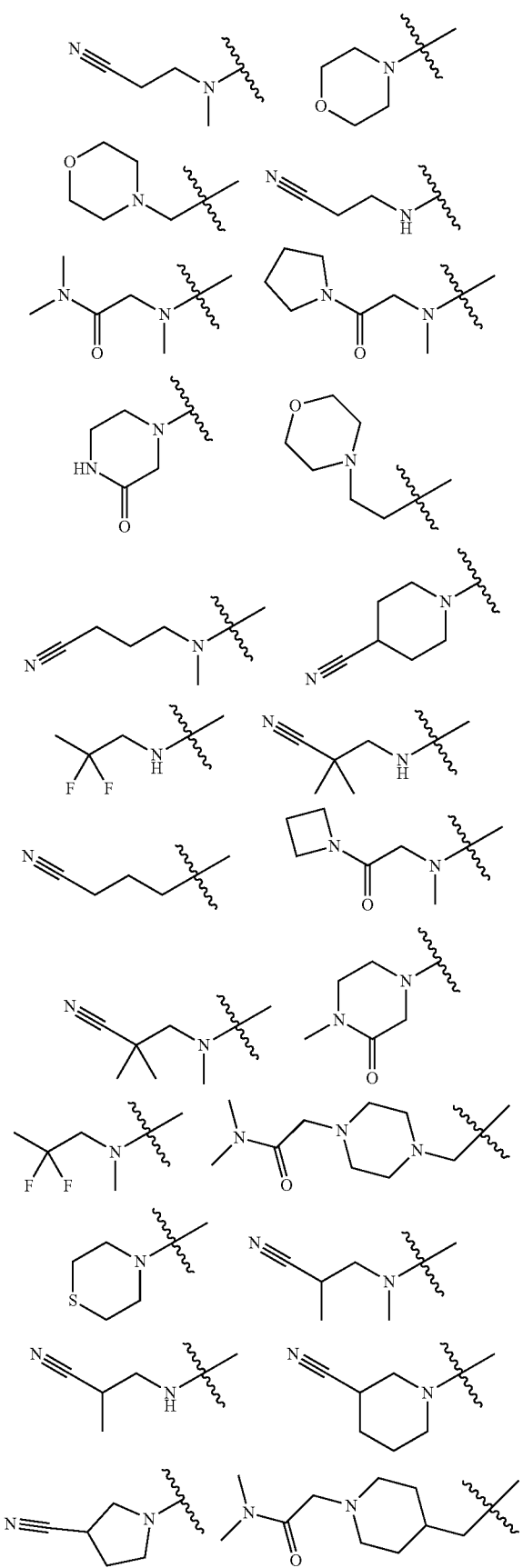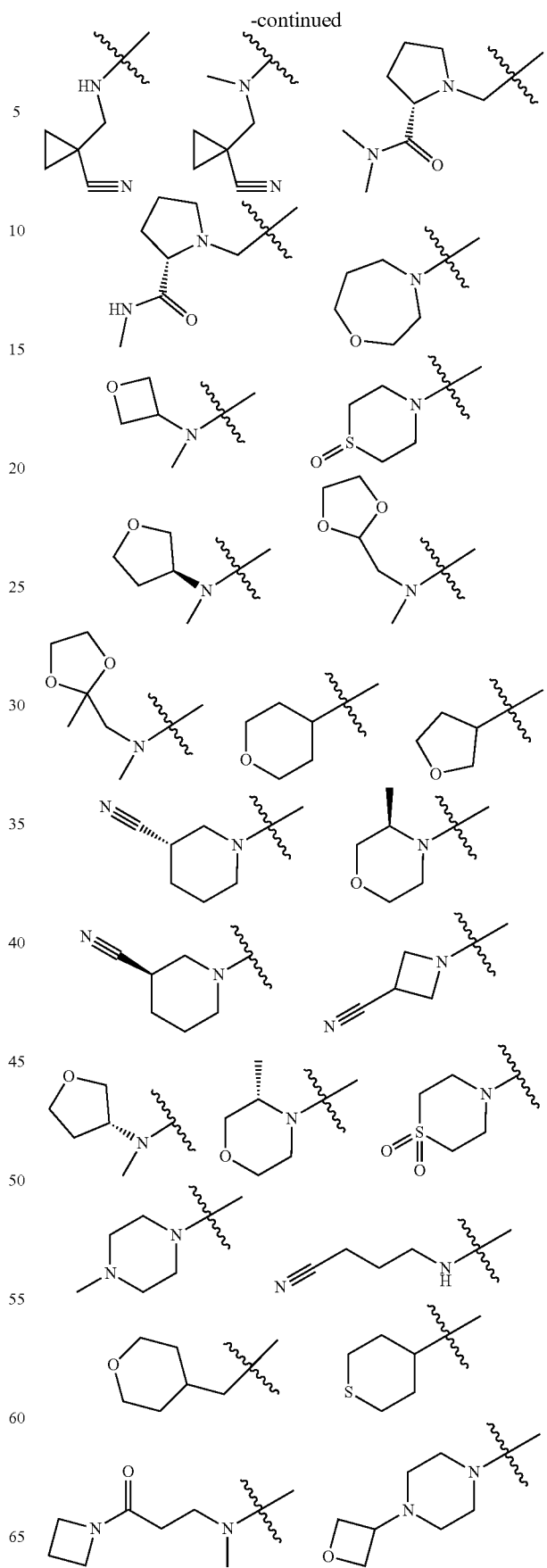

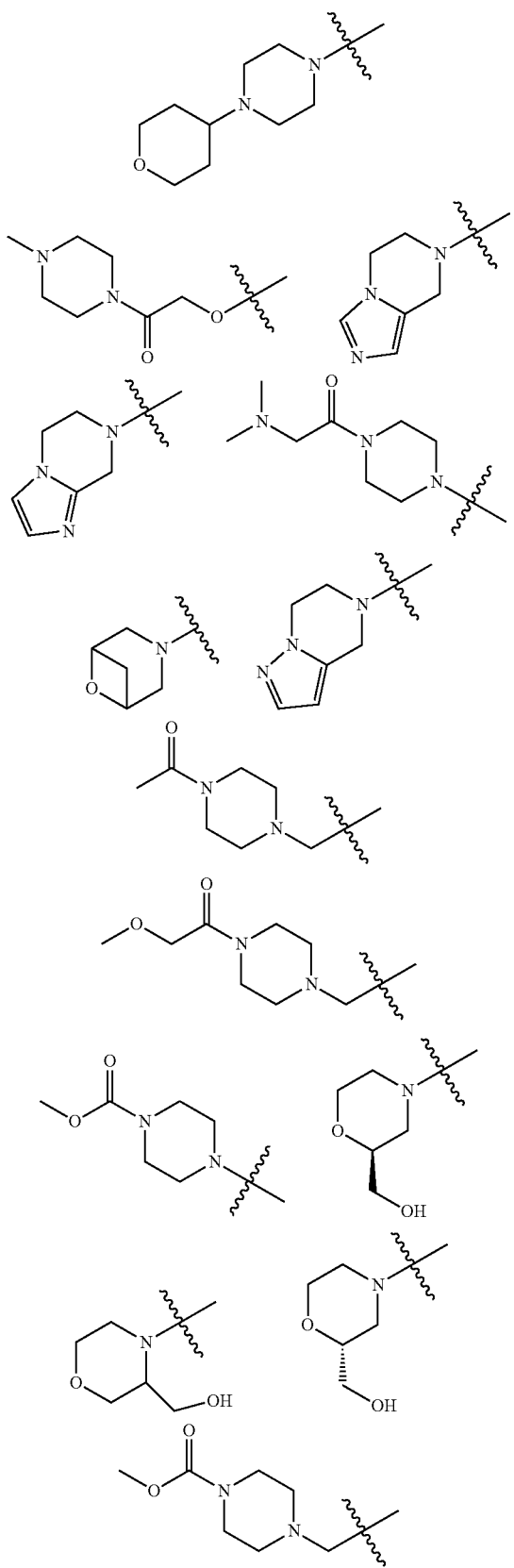
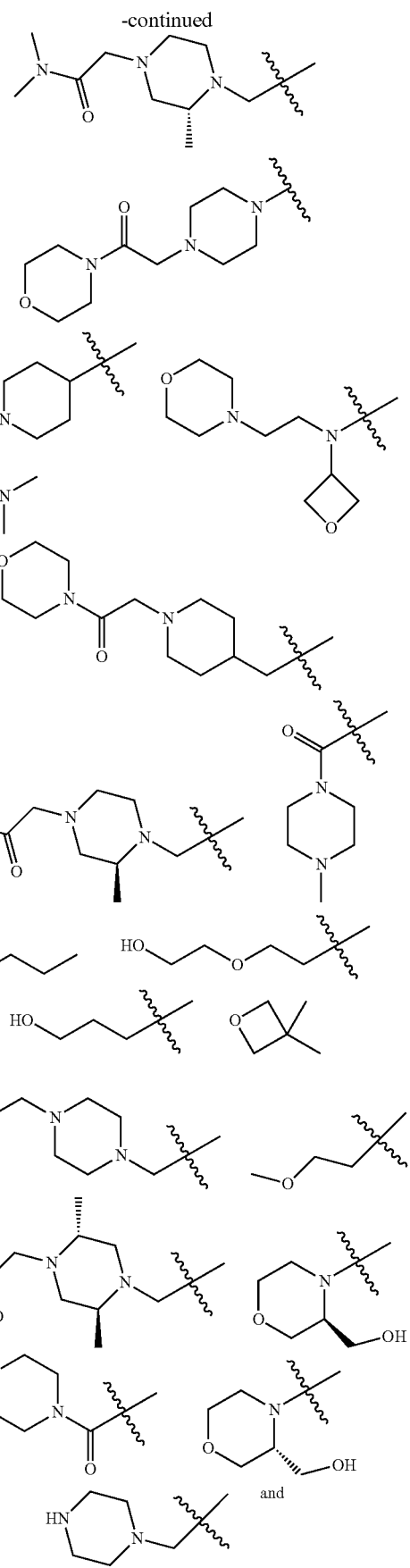

-continued

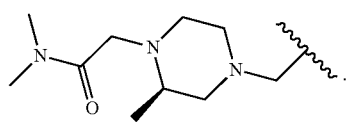

In one embodiment $R^e$ is selected from the group consisting of,

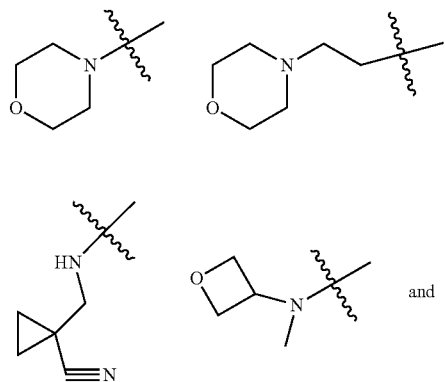

In one embodiment $R^2$ is phenyl that is optionally substituted by 1-5 $R^n$.

In one embodiment $R^2$ is phenyl that is optionally substituted by 1-2 $R^n$.

In one embodiment $R^2$ is selected from:

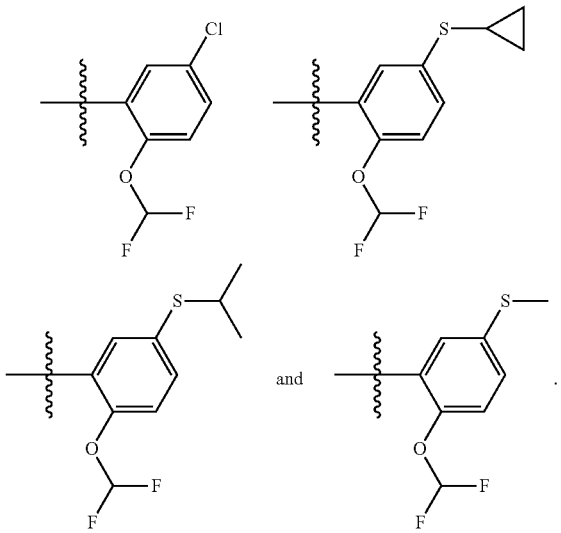

In one embodiment $R^2$ is:

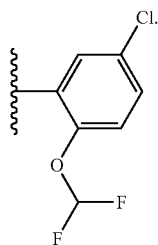 [SMILES: *c1cc(Cl)ccc1OC(F)F]

In one embodiment $R^2$ is:

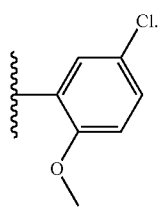 [SMILES: *c1cc(Cl)ccc1OC]

In one embodiment X is a 9-membered bicyclic heteraryl that comprises 2 or 3 atoms each independently selected from the group consisting of O, S, and N, wherein the 9-membered bicyclic heteroaryl is optionally substituted with $R^u$.

In one embodiment X is a 9-membered bicyclic heteraryl that comprises 2 atoms each independently selected from the group consisting of O, S, and N, wherein the 9-membered bicyclic heteroaryl is optionally substituted with $R^u$.

In one embodiment X is a 9-membered bicyclic heteraryl that comprises 3 atoms each independently selected from the group consisting of O, S, and N, wherein the 9-membered bicyclic heteroaryl is optionally substituted with $R^u$.

In one embodiment X is a 9-membered bicyclic heteraryl that comprises at least 2 nitrogen atoms and that is optionally substituted with $R^u$.

In one embodiment X is a 9-membered bicyclic heteraryl that comprises at least 3 nitrogen atoms and that is optionally substituted with more $R^u$.

In one embodiment X selected from the group consisting of:

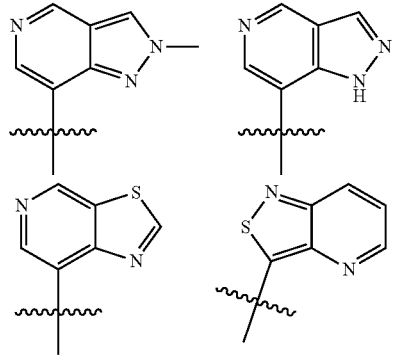

-continued

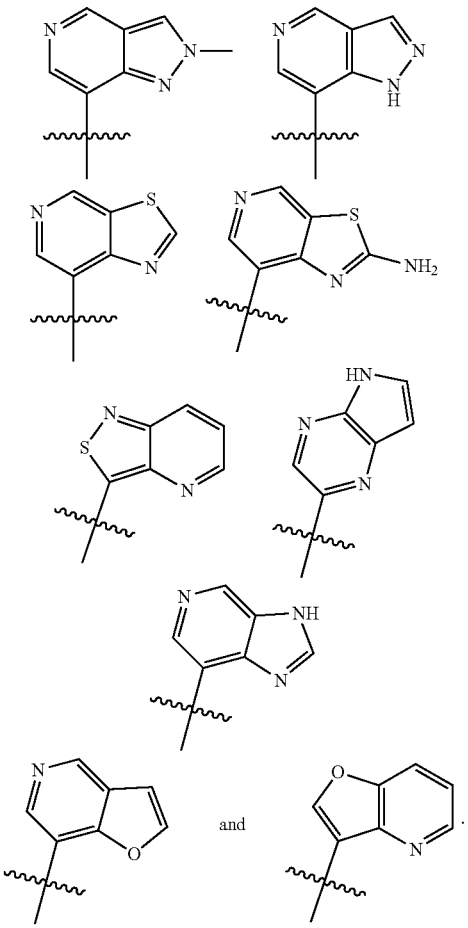

and is optionally substituted with $R^u$.

In one embodiment X selected from the group consisting of:

In one embodiment X is a 10-membered bicyclic heteraryl that comprises 2 or 3 atoms each independently selected from the group consisting of O, S, and N, wherein the 10-membered bicyclic heteroaryl is optionally substituted with $R^u$.

In one embodiment X is a 10-membered bicyclic heteraryl that comprises 2 atoms each independently selected from the group consisting of O, S, and N, wherein the 10-membered bicyclic heteroaryl is optionally substituted with $R^u$.

In one embodiment X is a 10-membered bicyclic heteraryl that comprises 3 atoms each independently selected from the group consisting of O, S, and N, wherein the 10-membered bicyclic heteroaryl is optionally substituted with $R^u$.

In one embodiment X is a 10-membered bicyclic heteraryl that comprises at least 2 nitrogen atoms and that is optionally substituted with $R^u$.

In one embodiment X is a 10-membered bicyclic heteraryl that comprises at least 3 nitrogen atoms and that is optionally substituted with $R^u$.

In one embodiment X is not selected from the group consisting of:

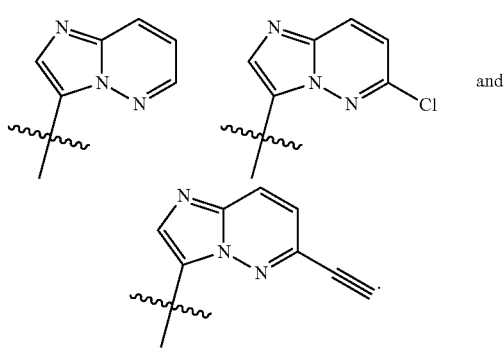

In one embodiment X is selected from the group consisting of:

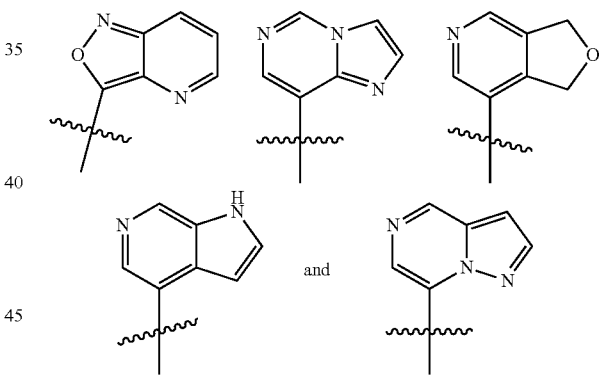

and is optionally substituted with $R^u$.

In one embodiment the invention provides a compound of the formula:

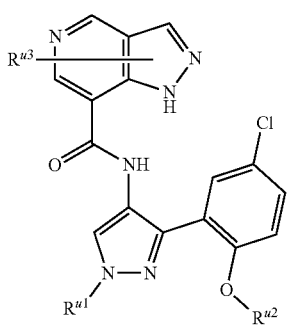

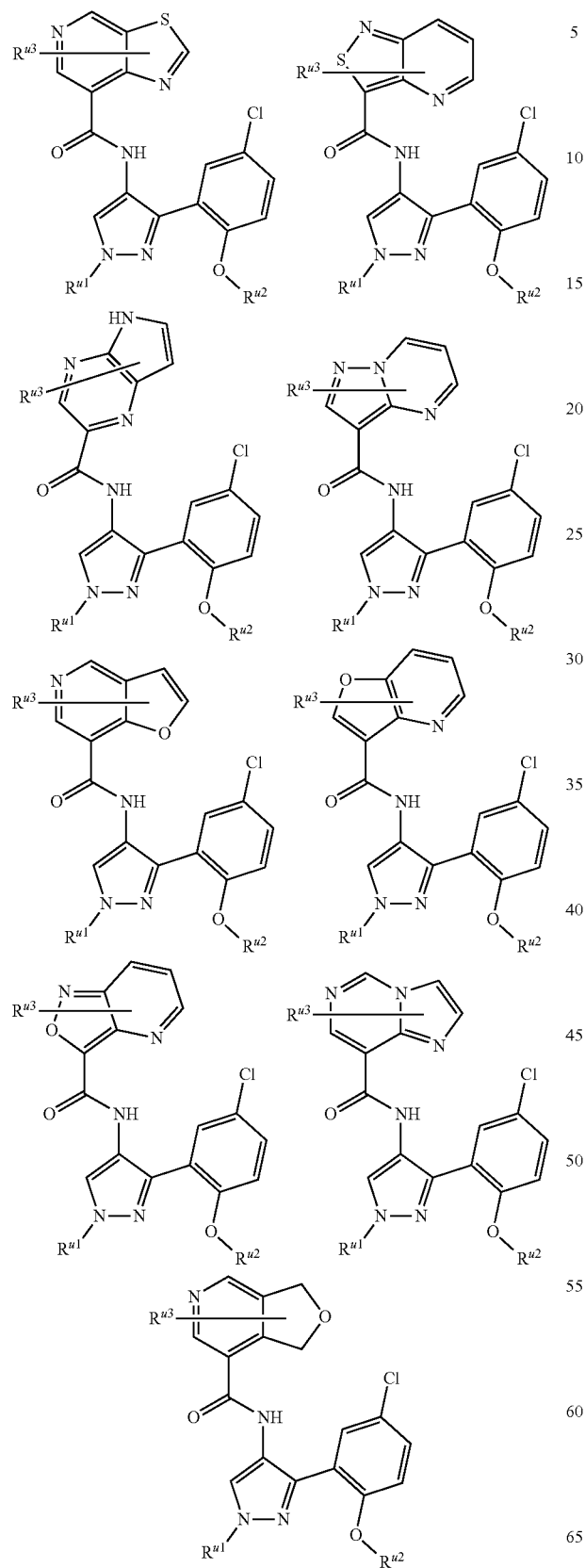
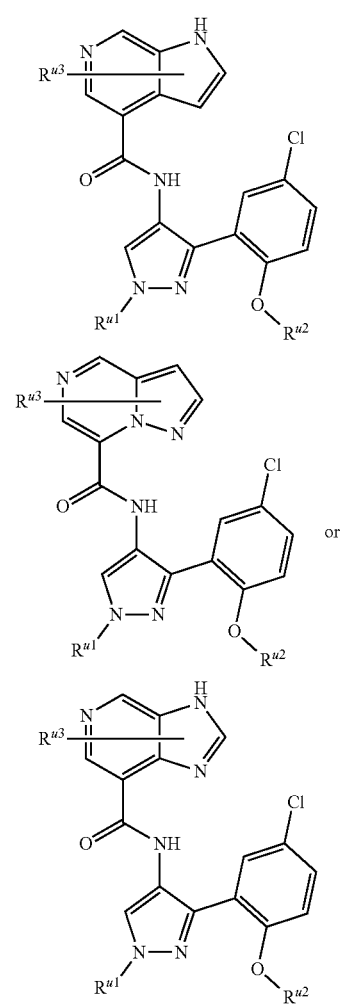
wherein:
$R^{u1}$ is H or methyl;
$R^{u2}$ is methyl or difluoromethyl; and
$R^{u3}$ is methyl, methoxy, halo, or $NH_2$;
or a salt thereof.
In one embodiment the invention provides a compound of the formula:
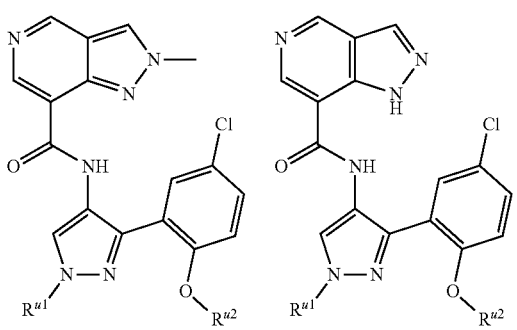

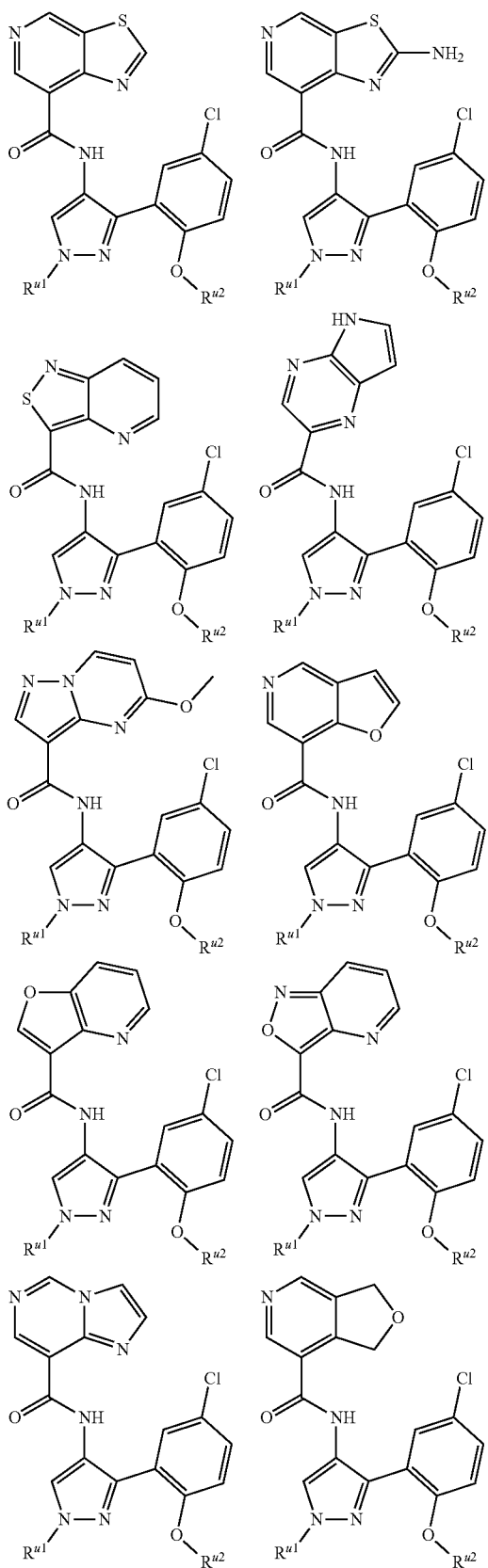
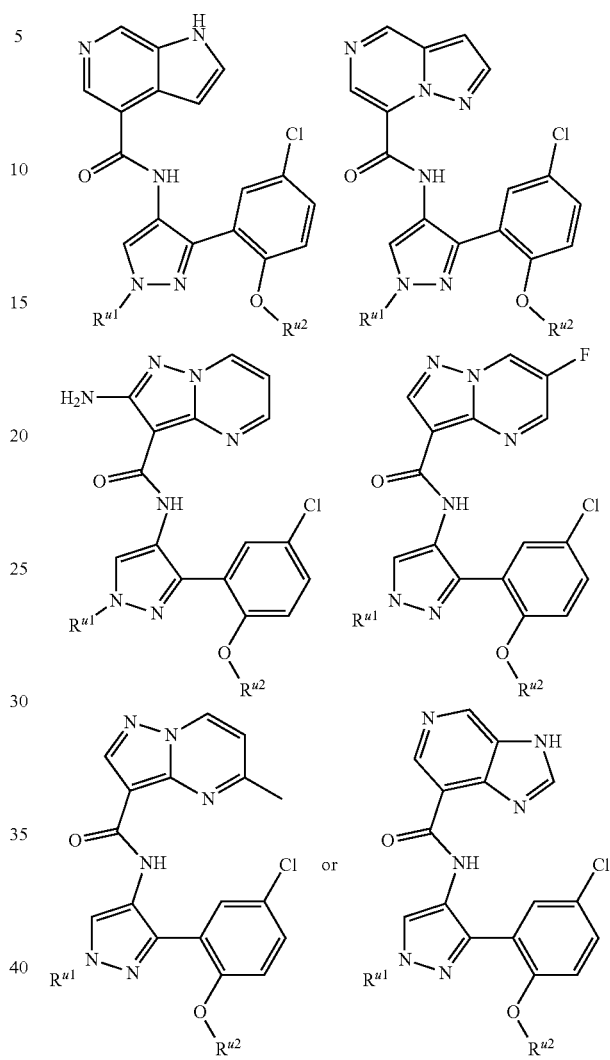
wherein:
$R^{u1}$ is H or methyl; and
$R^{u2}$ is methyl or difluoromethyl;
or a salt thereof.
In one embodiment the invention provides a compound of the formula:
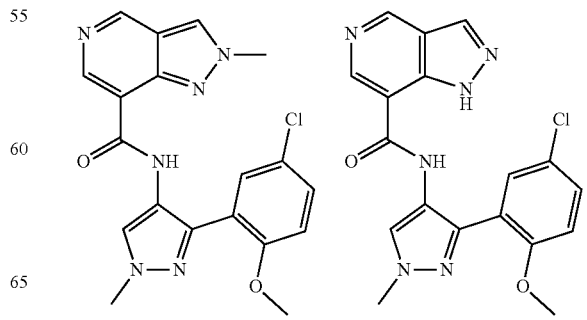

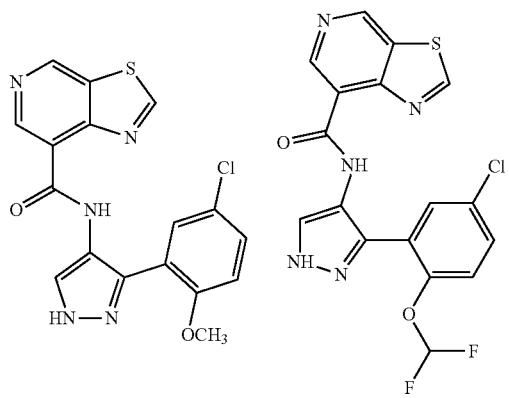
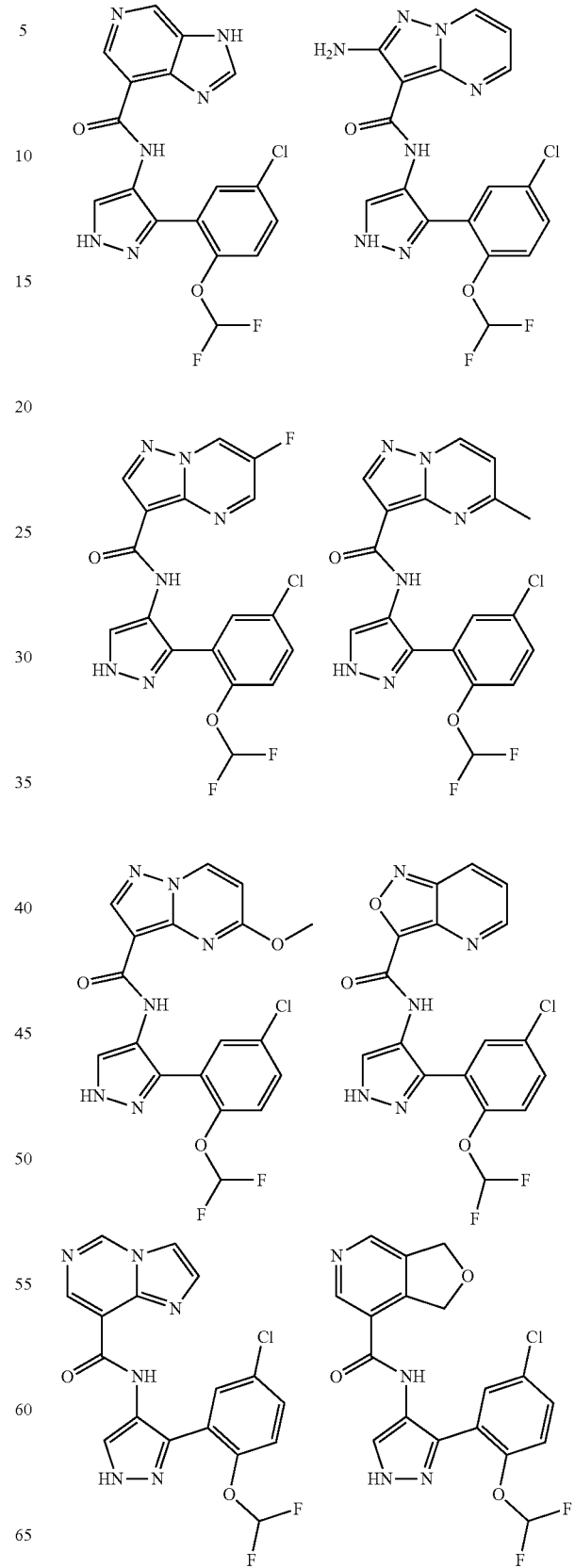

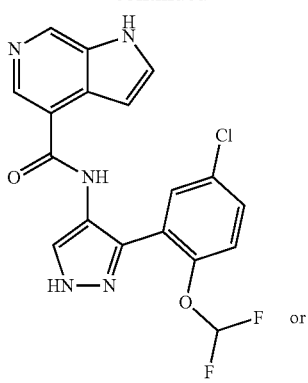

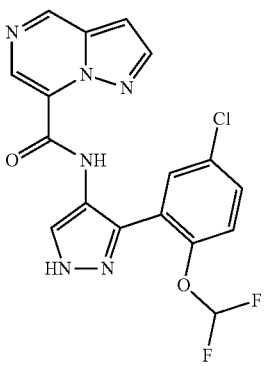

or a salt thereof.

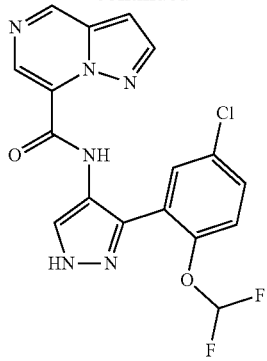

or a salt thereof.

In one embodiment the invention provides a compound of formula (I) wherein X is not:

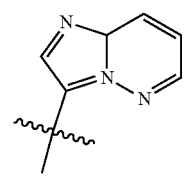

optionally substituted with $R^u$.

In one embodiment the invention provides a compound of formula (I) wherein X is not:

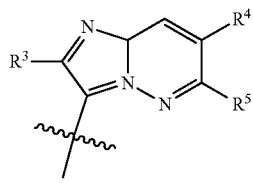

wherein:
R³ is H, halogen, cyano, $C_1$-$C_3$alkyl, $C_2$-$C_3$alkenyl, $C_2$-$C_3$alkynyl, or —$OR^t$;
R⁴ is H, halogen, cyano, $C_1$-$C_3$alkyl, $C_2$-$C_3$alkenyl, $C_2$-$C_3$alkynyl, or —$OR^t$;
R⁵ is H, halogen, cyano, $C_1$-$C_3$alkyl, $C_2$-$C_3$alkenyl, $C_2$-$C_3$alkynyl, or —$OR^t$; and
each R¹ is independently H, $C_1$-$C_6$ alkyl, $C_2$-$C_6$ alkenyl, $C_2$-$C_6$ alkynyl, or —($C_0$-$C_3$ alkyl)phenyl.

In one embodiment the invention provides a compound of formula (I) which is not:

a salt thereof.

In one embodiment the invention provides a compound of the formula:

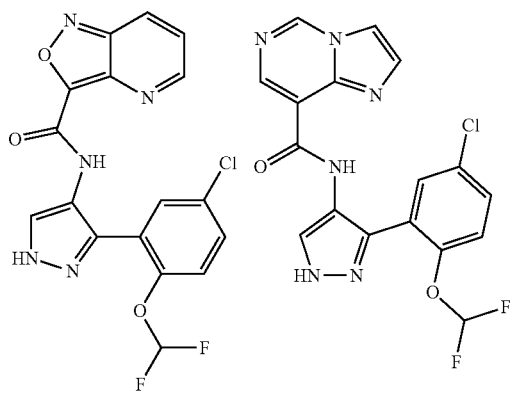

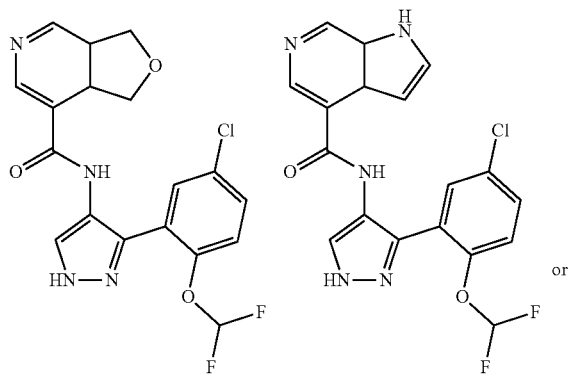

or

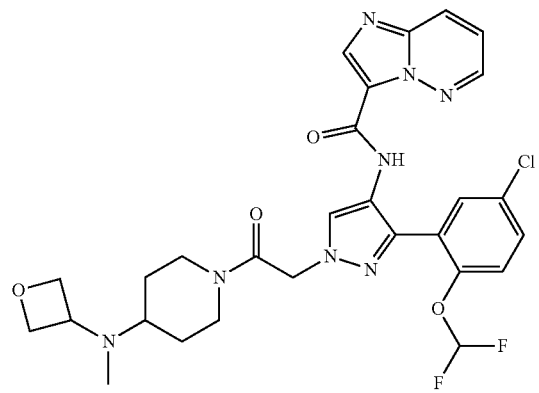

67
-continued
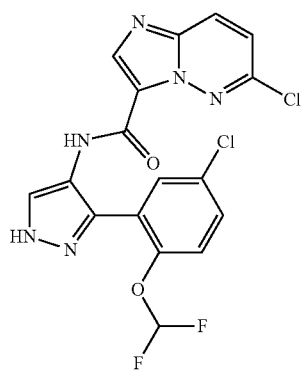
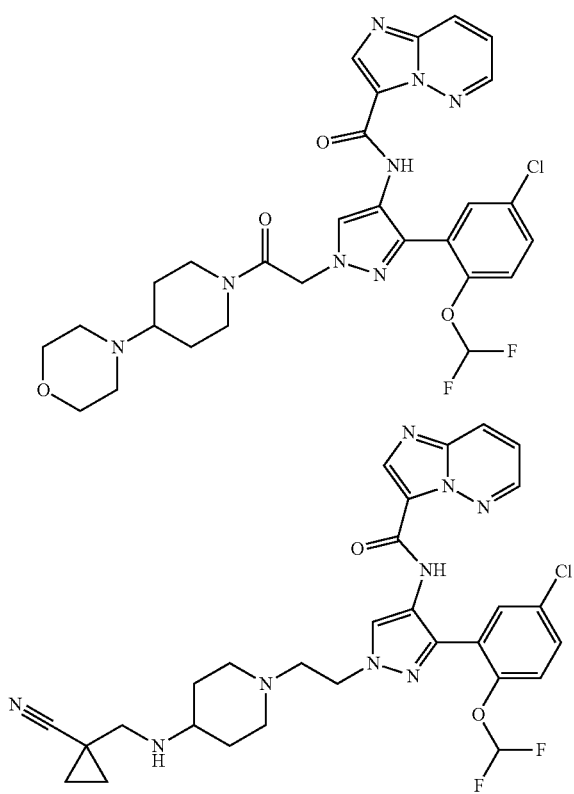
68
-continued
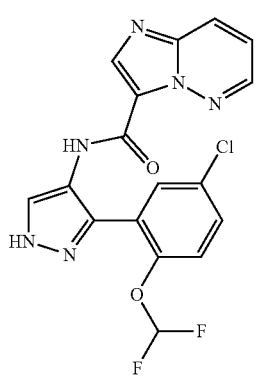
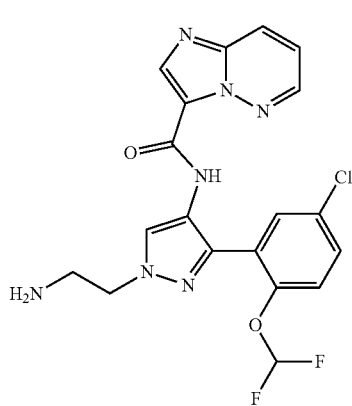

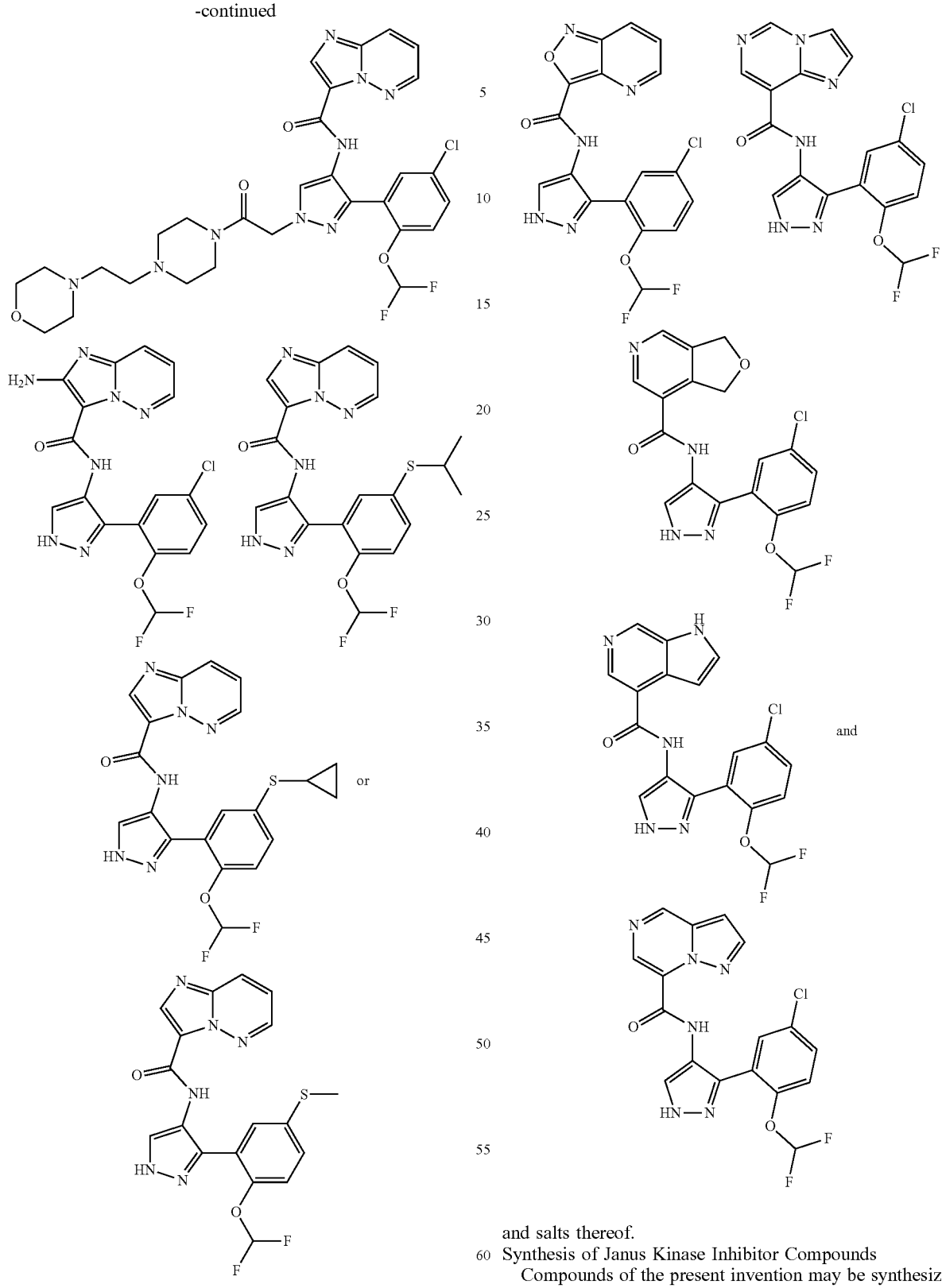

or a salt thereof.

The following compounds of the invention can be prepared using commercially available starting materials in a manner similar to the procedures found herein:

and salts thereof.

Synthesis of Janus Kinase Inhibitor Compounds

Compounds of the present invention may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or Comprehensive Heterocyclic Chemistry, Editors Katrizky and Rees, Pergamon Press, 1984.

Compounds may be prepared singly or as compound libraries comprising at least 2, for example 5 to 1,000 compounds, or 10 to 100 compounds. Libraries of compounds may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of the present invention, such as a compound of Formula I, or a compound of Table 1 or of Examples 1-15.

For illustrative purposes, reaction Schemes 1-16 depicted below provide routes for synthesizing the compounds of the present invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, benzyl, phenylsulfonyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Other conversions commonly used in the synthesis of compounds of the present invention, and which can be carried out using a variety of reagents and conditions, include the following:
(1) Reaction of a carboxylic acid with an amine to form an amide. Such a transformation can be achieved using various reagents known to those skilled in the art but a comprehensive review can be found in *Tetrahedron*, 2005, 61, 10827-10852.
(2) Reaction of a primary or secondary amine with an aryl halide or pseudo halide, e.g., a triflate, commonly known as a "Buchwald-Hartwig cross-coupling," can be achieved using a variety of catalysts, ligands and bases. A review of these methods is provided in *Comprehensive Organic Name Reactions and Reagents*, 2010, 575-581.
(3) A palladium cross-coupling reaction between an aryl halide and a vinyl boronic acid or boronate ester. This transformation is a type of "Suzuki-Miyaura cross-coupling," a class of reaction that has been thoroughly reviewed in *Chemical Reviews*, 1995, 95(7), 2457-2483.
(4) The hydrolysis of an ester to give the corresponding carboxylic acid is well known to those skilled in the art and conditions include: for methyl and ethyl esters, the use of a strong aqueous base such as lithium, sodium or potassium hydroxide or a strong aqueous mineral acid such as HCl; for a tert-butyl ester, hydrolysis would be carried out using acid, for example, HCl in dioxane or trifluoroacetic acid (TFA) in dichloromethane (DCM).

Other exemplary transformations are discussed following the Schemes below.

Reaction Scheme 1

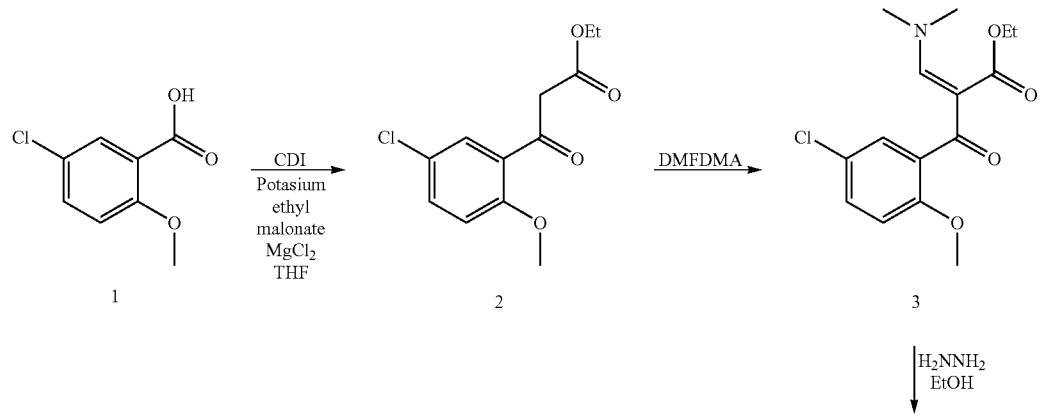

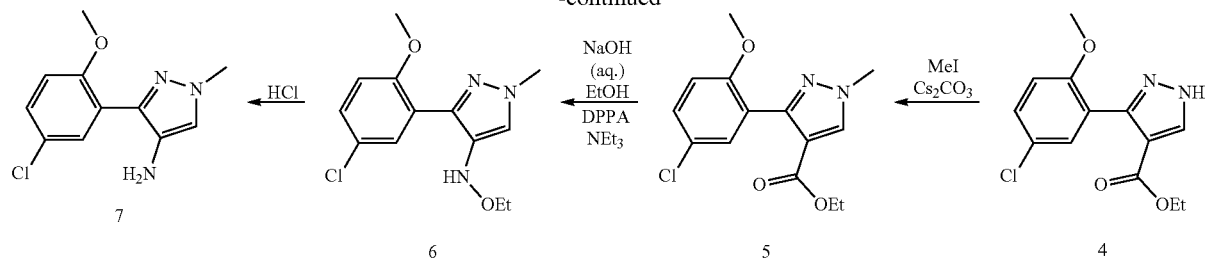

A method for the synthesis of intermediates of Formula 7 is illustrated in Reaction Scheme 1. β-ketoesters 2 may be generated from compound 1 by reaction with the anion of malonate in the presence of magnesium chloride. Compound 2 can be heated with DMFDMA to give compound 3. Cyclization of compound 4 with hydrazine in ethanol provides pyrazole compound 4. Saponification of 5 under basic conditions followed by Curtius rearrangement may be used to give boc-aminopyrazoles 6. Removal of the Boc protecting group by aqueous HCl in ethanol generates compounds 7.

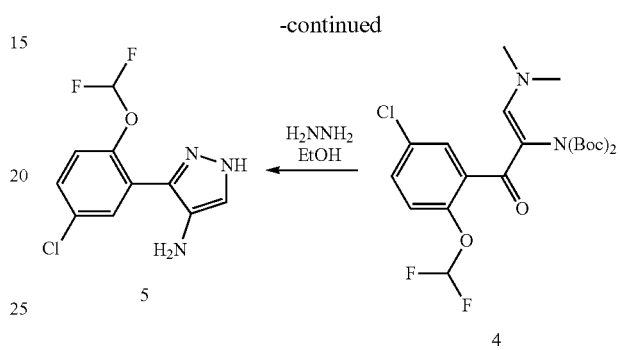

A method for the synthesis of intermediates of Formula 5 is illustrated in Reaction Scheme 2. α-Bromoketones can be generated from compound 1 with a reagent such as bromine. Alkylation of di-tert-butyl iminodicarbonate with sodium hydride and various α-bromoketones 2 generates compound 3. Compound 3 can be heated with DMFDMA to give compound 4. Cyclization of compound 4 with hydrazine in ethanol provides pyrazole compound 5.

Reaction Scheme 2

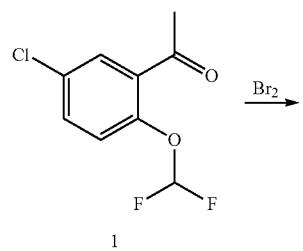

Reaction Scheme 3

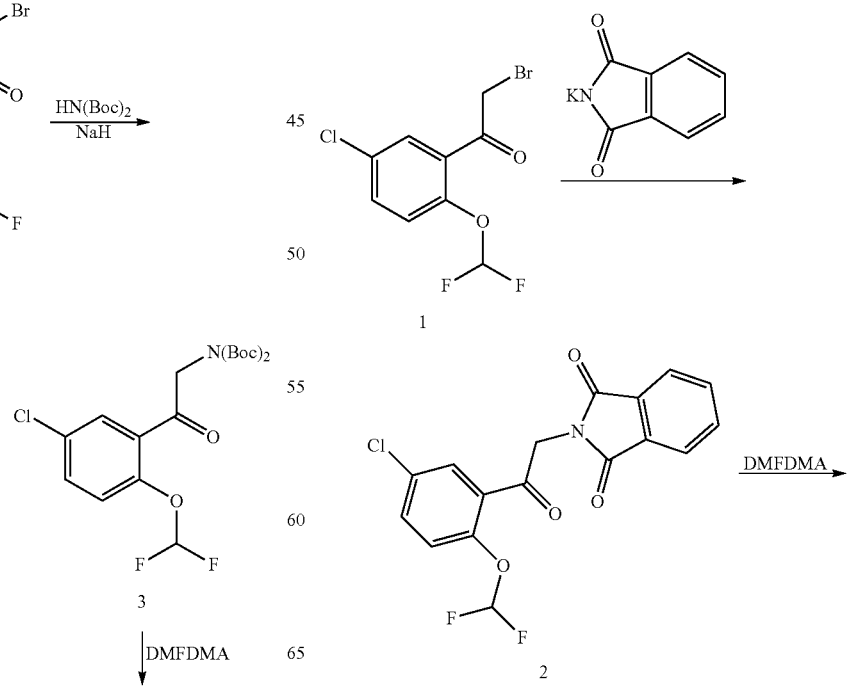

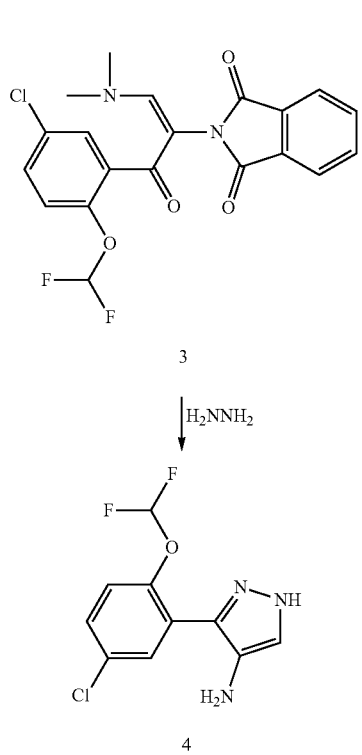

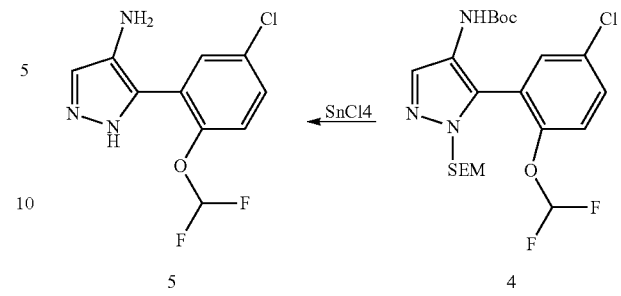

Reaction Scheme 4 illustrates an alternate synthesis for compounds of formula 5. Nitro-SEM pyrazole compound 1, prepared as in Reaction Scheme 5, may be regioselectively deprotonated with lithium hexamethyldisilazide at low temperature and quenched with iodine to yield 2. The nitro group of compound 2 can be reduced in the presence of iron and ammonium chloride, followed by Boc protection to generate compound 3. Compound 3 may be coupled under Suzuki conditions with aryl boronic acids or aryl boronates to yield compounds 4. After cleavage of the Boc group with tin tetrachloride, compounds of formula 5 are obtained.

An alternative method for the synthesis of compounds of Formula 4 is described in Reaction Scheme 3. Alkylation of potassium phthalimide with α-bromoketones 1 generates compound 2. Condensation with DMFDMA yields compounds 3. Compound 3 may be cyclized with hydrazine to yield compound 4.

Reaction Scheme 4

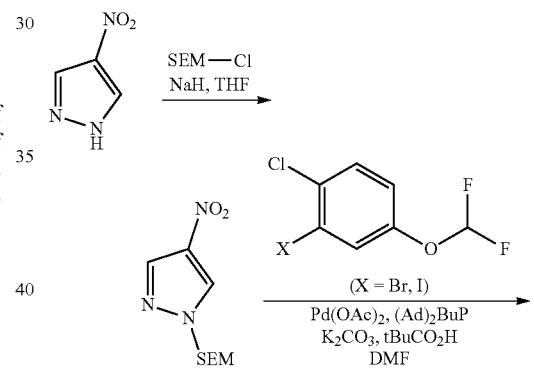

Reaction Scheme 5

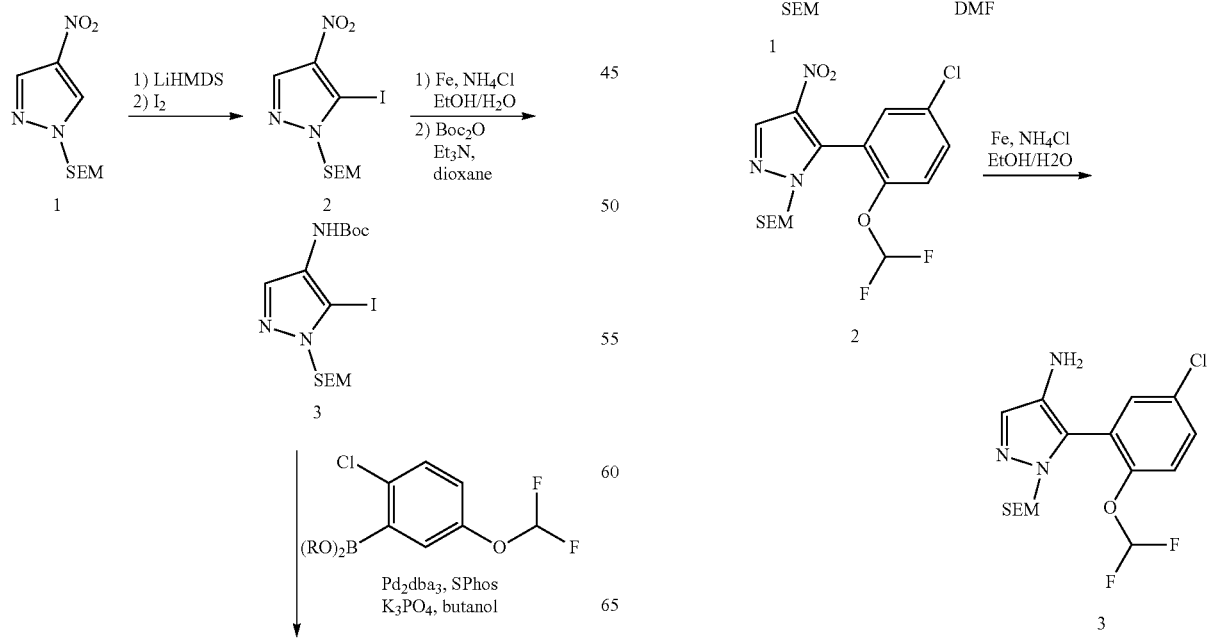

An alternate method for the synthesis of compounds of Formula 3 is shown in Reaction Scheme 5. Commercially available 4-nitro-1H-pyrazole may be protected with a [β-(trimethylsilyl)ethoxy]methyl (SEM) group by treatment with sodium hydride and (2-(chloromethoxy)ethyl)trimethylsilane. The resulting compound 1 can be arylated with aryl bromides or iodides under palladium catalyzed conditions to generated 4-nitro-5-aryl-pyrazoles of formula 2. The nitro group of compounds 2 can be reduced in the presence of iron and ammonium chloride to generate amino pyrazoles 3.

substituent R1, but the reaction generally favors formation of product 2b. Compounds 2a and 2b can be reduced to compounds 3a and 3b in the presence of iron and ammonium chloride in ethanol and water.

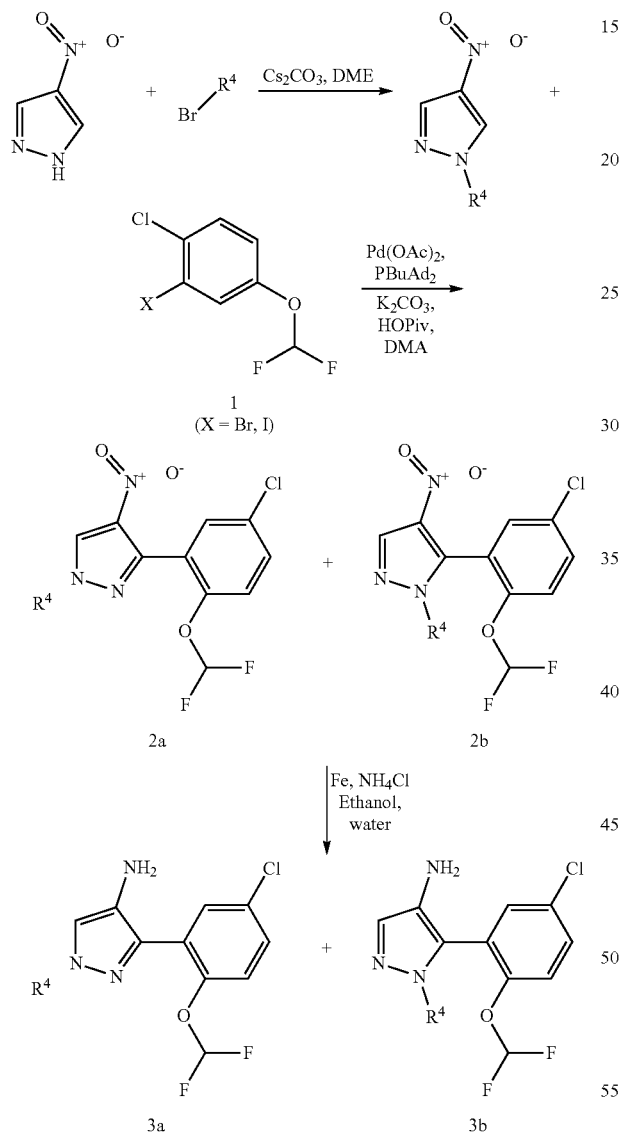

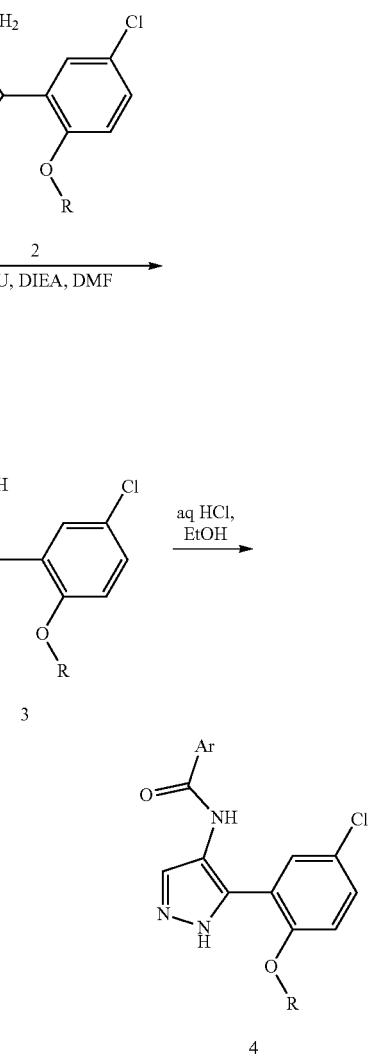

An alternate method for the synthesis of compounds of Formula 3a and 3b is shown in Reaction Scheme 6. Commercially available 4-Nitro-1H-pyrazole can be reacted with alkyl bromides in the presence of cesium carbonate to give compound 1. Compound 1 can be reacted with aryl bromides in N,N-Dimethylacetamide in the presence of Palladium (II) acetate, Di(1-adamntyl)-n-butylphosphine, potassium carbonate and trimethylacetic acid to give compounds 2a and 2b. The ratio of products 2a:2b varies depending on the Reaction Scheme 7 illustrates a synthesis for compounds of formula 4. Amide bond coupling with commercially available substituted pyrazolo[1,5-a]pyrimidine-3-carboxylic acids in the presence of HATU and DIEA provides compounds 3. Removal of the SEM protecting group by aqueous HCl in ethanol generates compounds 4.

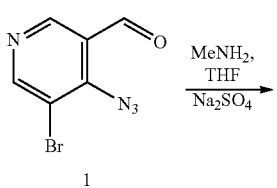

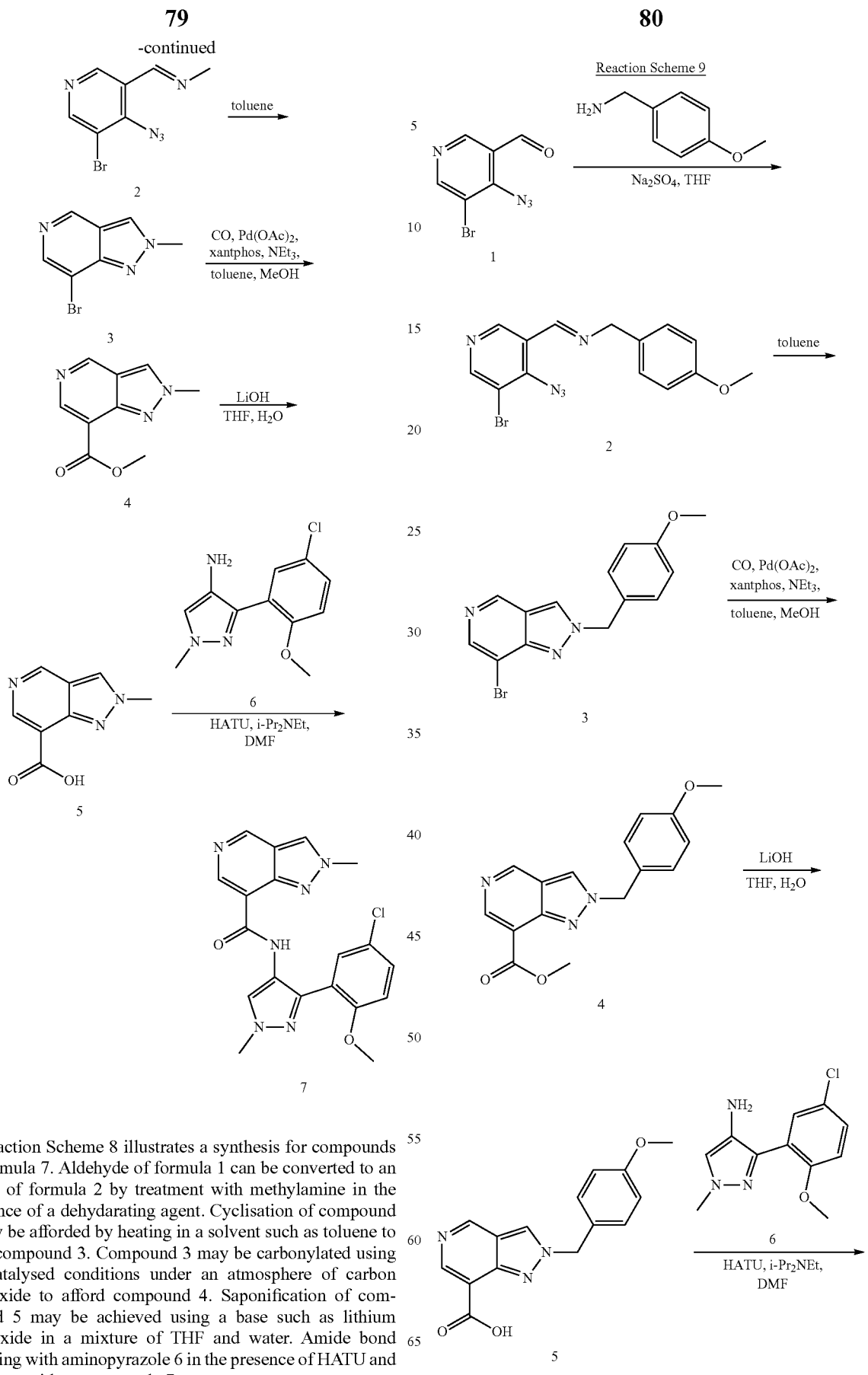

Reaction Scheme 8 illustrates a synthesis for compounds of formula 7. Aldehyde of formula 1 can be converted to an imine of formula 2 by treatment with methylamine in the presence of a dehydarating agent. Cyclisation of compound 2 may be afforded by heating in a solvent such as toluene to give compound 3. Compound 3 may be carbonylated using Pd catalysed conditions under an atmosphere of carbon monoxide to afford compound 4. Saponification of compound 5 may be achieved using a base such as lithium hydroxide in a mixture of THF and water. Amide bond coupling with aminopyrazole 6 in the presence of HATU and DIEA provides compounds 7.

-continued

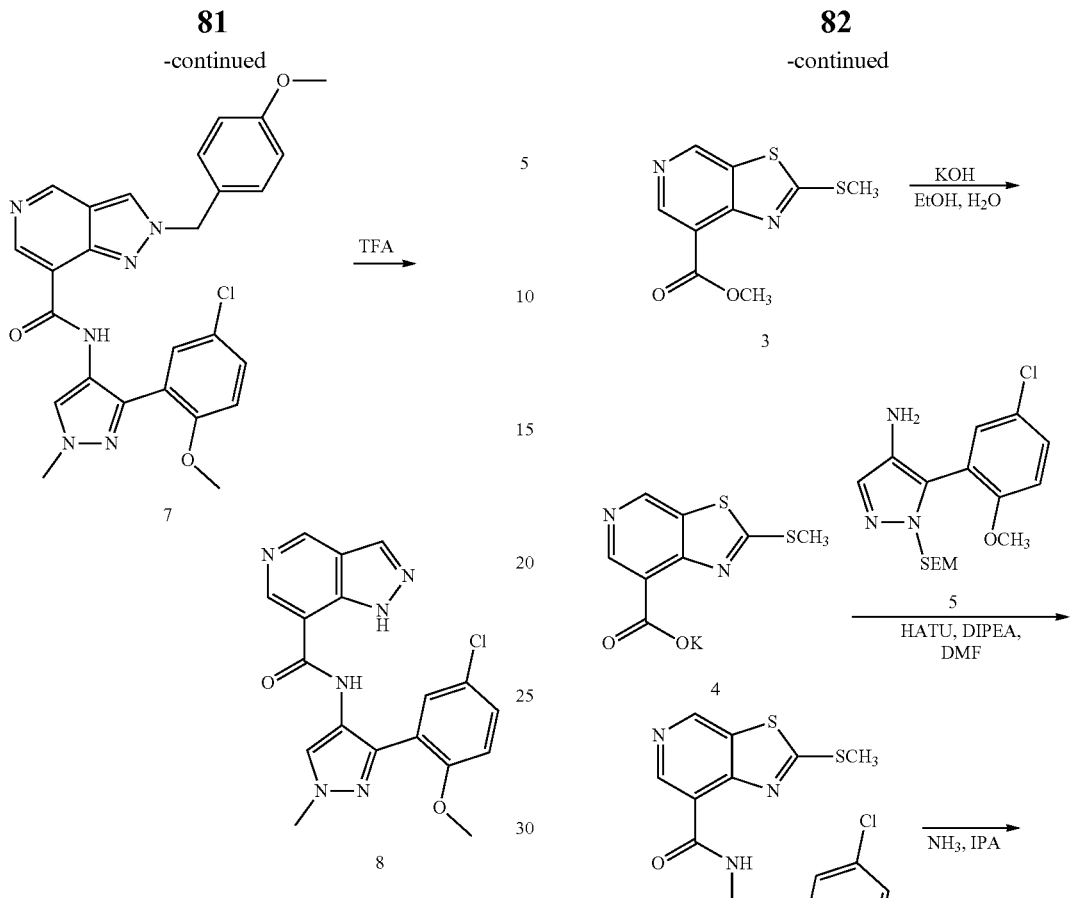

Reaction Scheme 9 illustrates a synthesis for compounds of formula 8. Aldehyde of formula 1 can be converted to a PMB-imine of formula 2 by treatment with 4-methoxybenzylamine in the presence of a dehydarating agent. Cyclisation of compound 2 may be afforded by heating in a solvent such as toluene to give compound 3. Compound 3 may be carbonylated using Pd catalysed conditions under an atmosphere of carbon monoxide to afford compound 4. Saponification of compound 5 may be achieved using a base such as lithium hydroxide in a mixture of THF and water. Amide bond coupling with aminopyrazole 6 in the presence of HATU and DIEA provides compounds 7. Removal of the PMB group may be achieved using by treatment with an acid such as TFA to give compounds of formula 8.

Reaction Scheme 10

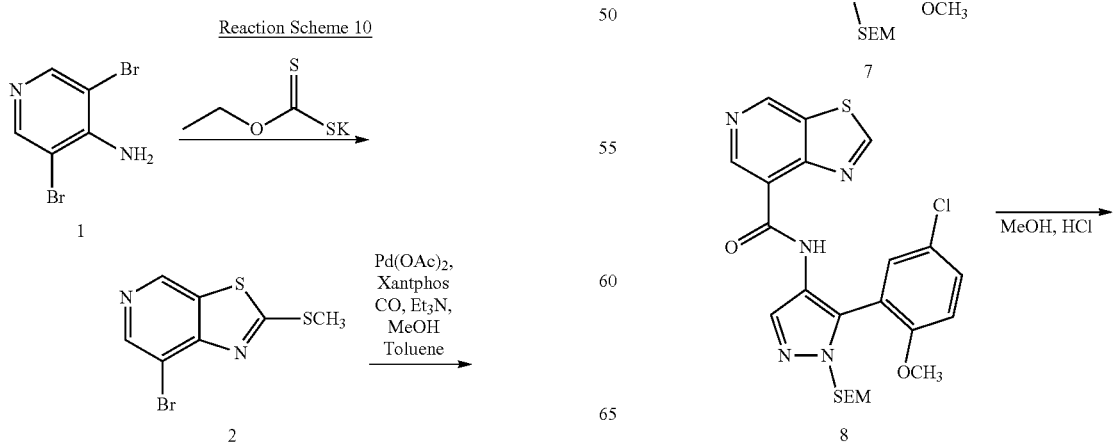

-continued

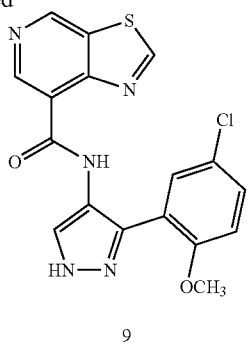

9

Reaction Scheme 10 illustrates a synthesis for compounds of formula 6. Compound of formula 1 may be converted to compounds of formula 2 using a two step process. Cyclisation may be afforded by treating compound 1 with a reagent such as potassium ethyl xanthogenate. Alkylation with methyl iodide may then afford compounds of formula 2. Compound 2 may be carbonylated using Pd catalysed conditions under an atmosphere of carbon monoxide to afford compound 4. Saponification of compound 5 may be achieved using a base such as potassium hydroxide in a mixture of EtOH and water. Amide bond coupling of compound 4 with aminopyrazole 5 in the presence of HATU and DIEA provides compounds 6. Compounds 6 may be treated with ammonia in a solvent such as isoproponal under elevated temperature in a sealed tube to afford compounds 7. Diazotisation of compounds 7 using a reagent such as amyl nitrite may give compounds 8. Removal of the SEM group from compound 8 may be achieved using by treatment with an acid such as HCl to give compounds of formula 9.

Reaction Scheme 11

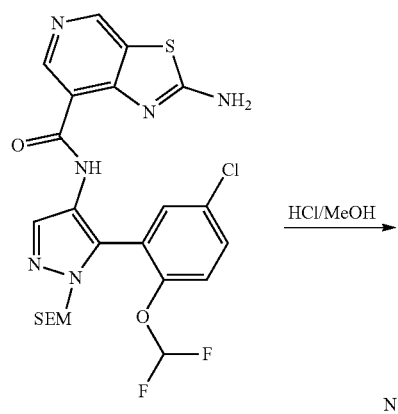

1

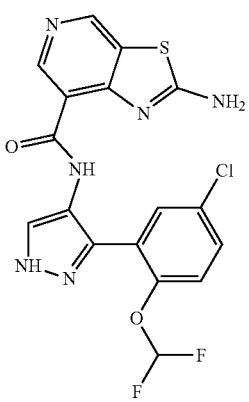

2

Reaction Scheme 11 illustrates a synthesis for compounds of formula 2. Removal of the SEM group from compound 1 may be achieved using by treatment with an acid such as HCl to give compounds of formula 9.

Reaction Scheme 12

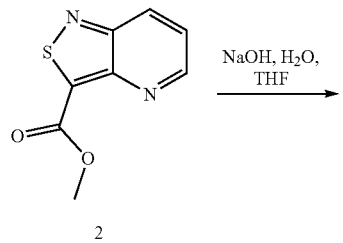

1

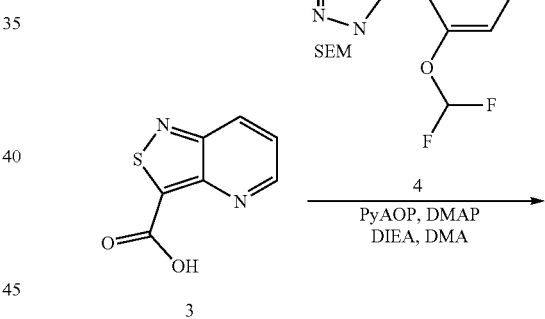

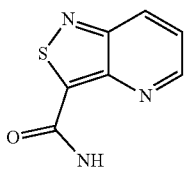

5

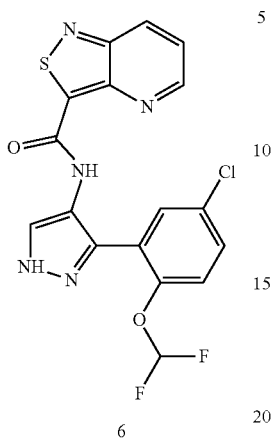

6

Reaction Scheme 12 illustrates a synthesis for compounds of formula 6. Compound 1 may be carbonylated using Pd catalysed conditions under an atmosphere of carbon monoxide to afford compound 2. Saponification of compound 5 may be achieved using a base such as sodium hydroxide in a mixture of THF and water. Amide bond coupling of compound 3 with aminopyrazole 4 in the presence of PyAOP and DIEA provides compounds 5. Removal of the SEM group from compound 5 may be achieved using by treatment with an acid such as HCl to give compounds of formula 6.

Reaction Scheme 13

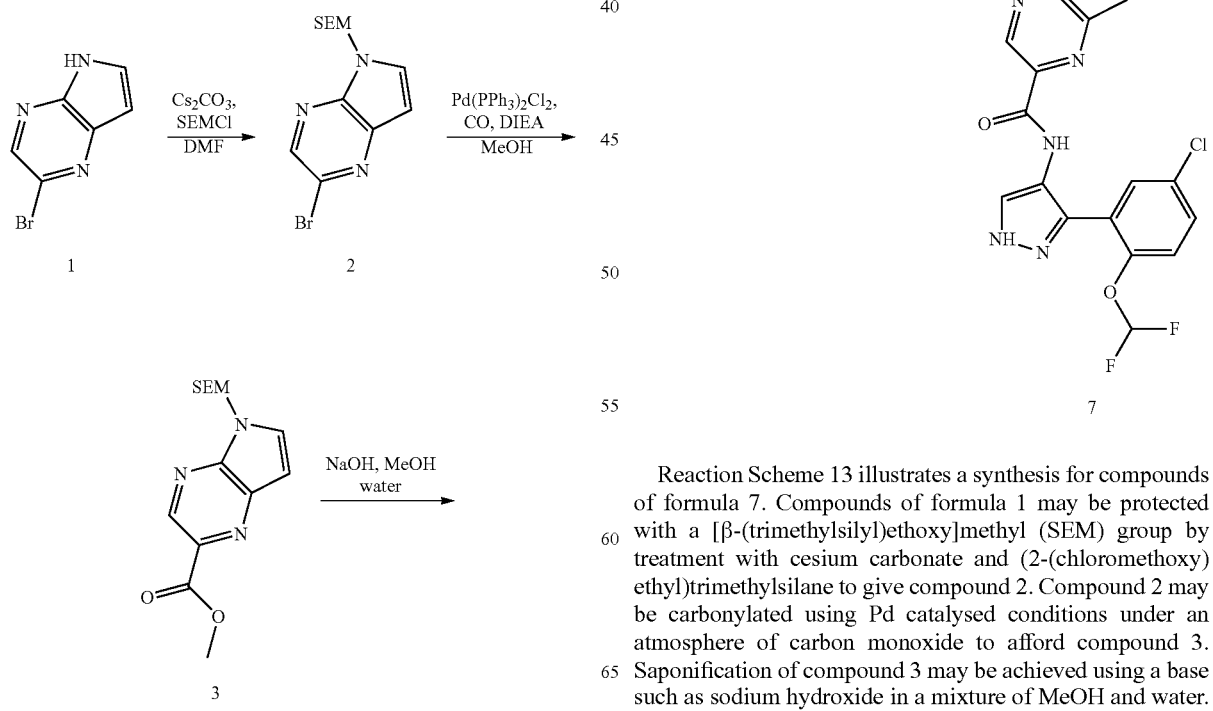

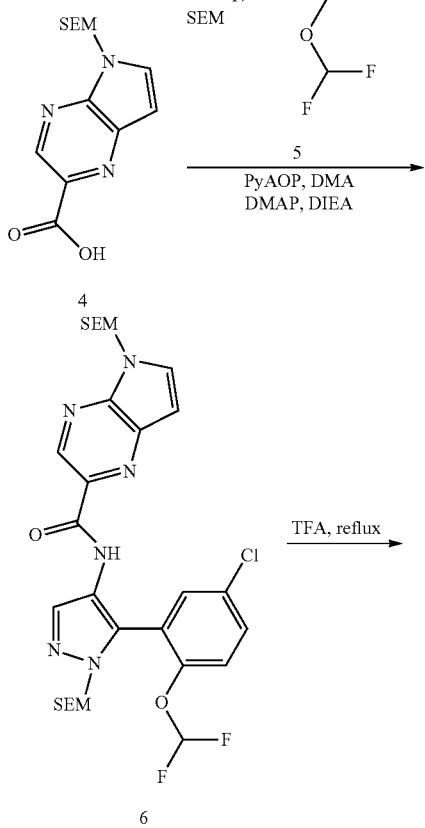

Reaction Scheme 13 illustrates a synthesis for compounds of formula 7. Compounds of formula 1 may be protected with a [β-(trimethylsilyl)ethoxy]methyl (SEM) group by treatment with cesium carbonate and (2-(chloromethoxy) ethyl)trimethylsilane to give compound 2. Compound 2 may be carbonylated using Pd catalysed conditions under an atmosphere of carbon monoxide to afford compound 3. Saponification of compound 3 may be achieved using a base such as sodium hydroxide in a mixture of MeOH and water. Amide bond coupling with aminopyrazole 5 in the presence of PyAOP and DIEA provides compounds 6. Removal of the SEM group may be achieved using by treatment with an acid such as TFA to give compounds of formula 7.

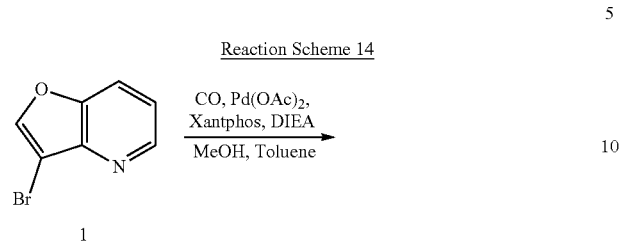

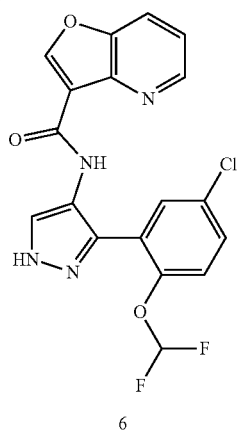

Reaction Scheme 14 illustrates a synthesis for compounds of formula 6. Compound 1 may be carbonylated using Pd catalysed conditions under an atmosphere of carbon monoxide to afford compound 2. Saponification of compound 3 may be achieved using a base such as lithium hydroxide in a mixture of THF and water. Amide bond coupling with aminopyrazole 4 in the presence of PyAOP and DIEA provides compounds 5. Removal of the SEM group may be achieved using by treatment with an acid such as TFA to give compounds of formula 6.

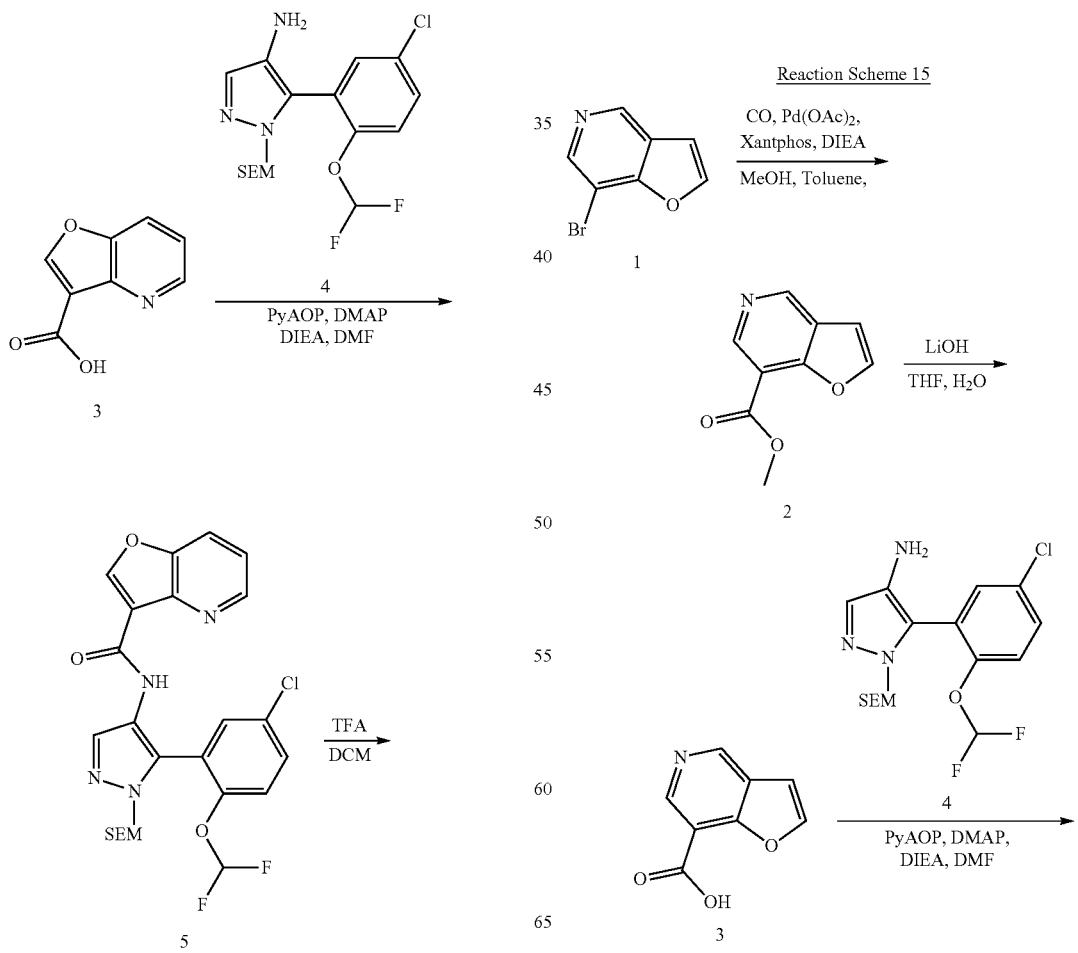

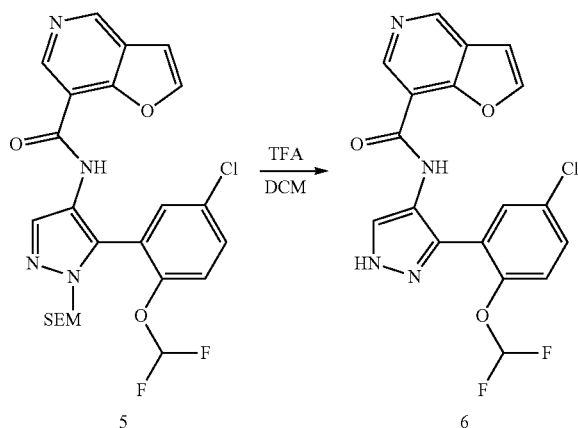

Reaction Scheme 15 illustrates a synthesis for compounds of formula 6. Compound 1 may be carbonylated using Pd catalysed conditions under an atmosphere of carbon monoxide to afford compound 2. Saponification of compound 3 may be achieved using a base such as lithium hydroxide in a mixture of THF and water. Amide bond coupling with aminopyrazole 4 in the presence of PyAOP and DIEA provides compounds 5. Removal of the SEM group may be achieved using by treatment with an acid such as TFA to give compounds of formula 6.

Reaction Scheme 16

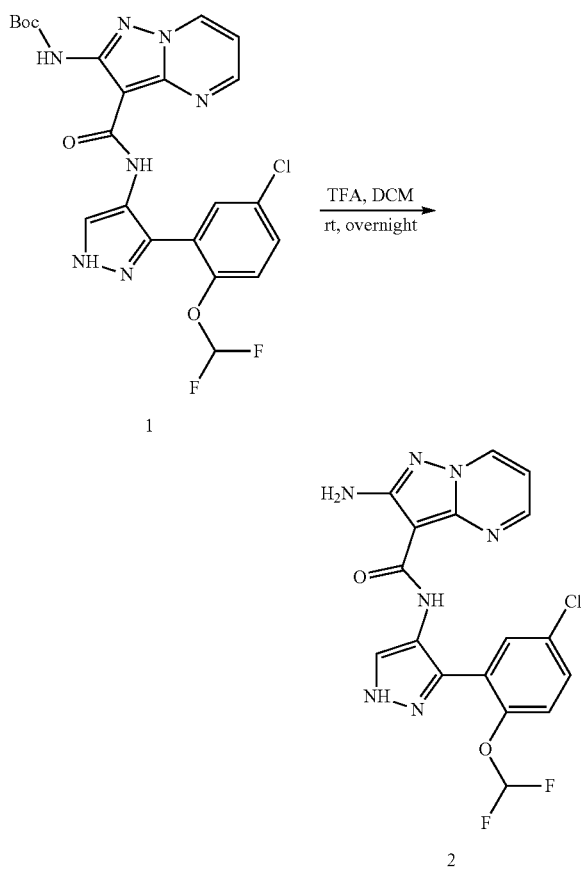

Reaction Scheme 16 illustrates a synthesis for compounds of formula 2. Removal of the Boc group may be achieved using by treatment with an acid such as TFA to give compounds of formula 2.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O(7-azabenzotriazol-1-yl)-N,N,N',N'-tetramethyl-uronium hexafluoro-phosphate) in a suitable solvent such as dichloromethane. Similarly, amine groups may be converted into sulphonamide groups (—NHSO$_2$R' or —NR"SO$_2$R') groups by reaction with an appropriate sulphonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (—NH$_2$) may be obtained by reduction of a nitro (—NO$_2$) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—CH$_2$NH$_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at an appropriate temperature, for example from about −78° C. to the reflux temperature of the solvent.

In a further example, amine (—NH$_2$) groups may be obtained from carboxylic acid groups (—CO$_2$H) by conversion to the corresponding acyl azide (—CON$_3$), Curtius rearrangement and hydrolysis of the resultant isocyanate (—N=C=O).

Aldehyde groups (—CHO) may be converted to amine groups (—CH$_2$NR'R")) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH=CHR') by the use of a Wittig or Wadsworth-Emmons reaction using an appropriate phosphorane or phosphonate under standard conditions known to those skilled in the art.

Aldehyde groups may be obtained by reduction of ester groups (such as —$CO_2Et$) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—$CO_2R'$) may be converted into the corresponding acid group (—$CO_2H$) by acid- or base-catalused hydrolysis, depending on the nature of R. If R is I-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—$CO_2H$) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e —$CO_2H$ to —$CH_2CO_2H$) by conversion to the corresponding acid chloride (—COCl) followed by Arndt-Eistert synthesis.

In a further example, —OH groups may be generated from the corresponding ester (e.g. —$CO_2R'$), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—$CO_2H$), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thioyl chloride in a halogenated hydrocarbon (e.g. dichloromethane) to yield the corresponding chloride. A base (e.g. tri ethyl amine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as w-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

Methods of Separation

In each of the exemplary Schemes it may be advantageous to separate reaction products from one another or from starting materials. The desired products of each step or series of steps is separated or purified (hereinafter separated) to the desired degree of homogeneity by the techniques common in the art. Typically such separations involve multiphase extraction, crystallization or trituration from a solvent or solvent mixture, distillation, sublimation, or chromatography. Chromatography can involve any number of methods including, for example: reverse-phase and normal phase; size exclusion; ion exchange; supercritical fluid; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. Example separation methods include boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column or supercritical fluid chromatography.

A single stereoisomer, e.g., an enantiomer, substantially free of its stereoisomer may be obtained by resolution of the racemic mixture using a method such as formation of diastereomers using optically active resolving agents (Eliel, E. and Wilen, S., Stereochemistry of Organic Compounds, John Wiley & Sons, Inc., New York, 1994; Lochmuller, C. H., J. Chromatogr., 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Drug Stereochemistry, Analytical Methods and Pharmacology, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., Stereochemistry of Organic Compounds, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob, J. Org. Chem. 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111, incorporated herein by reference). By method (3), a racemic mixture of two enantiomers can be separated by chromatography using a chiral stationary phase (Chiral Liquid Chromatography W. J. Lough, Ed., Chapman and Hall, New York, (1989); Okamoto, J. of Chromatogr. 513: 375-378 (1990)). Enriched or purified enantiomers can be distinguished by methods used to distinguish other chiral molecules with asymmetric carbon atoms, such as optical rotation and circular dichroism. The absolute stereochemistry of chiral centers and enatiomers can be determined by x-ray crystallography.

Positional isomers, for example E and Z forms, of compounds of Formula I, and intermediates for their synthesis, may be observed by characterization methods such as NMR and analytical HPLC. For certain compounds where the energy barrier for interconversion is sufficiently high, the E and Z isomers may be separated, for example by preparatory HPLC.

Pharmaceutical Compositions and Administration

The compounds with which the invention is concerned are JAK kinase inhibitors, such as JAK1 inhibitors, and are useful in the treatment of several diseases, for example, inflammatory diseases, such as asthma.

Accordingly, another embodiment provides pharmaceutical compositions or medicaments containing a compound of the invention, such as a compound of Formula I, or a compound of Table 1 or of Examples 1-15, and a pharmaceutically acceptable carrier, diluent or excipient, as well as methods of using the compounds of the invention to prepare such compositions and medicaments.

In one example, a compound of Formula I, or a compound of Table 1 or of Examples 1-15, may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but typically ranges anywhere from about 3 to about 8. In one example, a compound of Formula I, or a compound of Table 1 or of Examples 1-15, is formulated in an acetate buffer, at pH 5. In another embodiment, the compounds of the present invention, such as a compound of Formula I, or a compound of Table 1 or of Examples 1-15, are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 µg to about 1 mg per kg body weight of a human, preferably 0.1 µg to 50 µg per kg, in single or divided doses. On the other hand, it may be necessary to use dosages outside these limits in some cases.

The compounds of the invention, such as a compound of Formula I, or a compound of Table 1 or of Examples 1-15, may be administered by any suitable means, including oral, topical (including buccal and sublingual), rectal, vaginal, transdermal, parenteral, subcutaneous, intraperitoneal, intrapulmonary, intradermal, intrathecal, inhaled and epidural and intranasal, and, if desired for local treatment, intralesional administration. Parenteral infusions include intramuscular, intravenous, intraarterial, intraperitoneal, or subcutaneous administration. In some embodiments, inhaled administration is employed.

The compounds of the present invention, such as a compound of Formula I, or a compound of Table 1 or of Examples 1-15, may be administered in any convenient administrative form, e.g., tablets, powders, capsules, lozenges, granules, solutions, dispersions, suspensions, syrups, sprays, vapors, suppositories, gels, emulsions, patches, etc. Such compositions may contain components conventional in pharmaceutical preparations, e.g., diluents (e.g., glucose, lactose or mannitol), carriers, pH modifiers, buffers, sweeteners, bulking agents, stabilizing agents, surfactants, wetting agents, lubricating agents, emulsifiers, suspending agents, preservatives, antioxidants, opaquing agents, glidants, processing aids, colorants, perfuming agents, flavoring agents, other known additives as well as further active agents.

Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. For example, carriers include solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated. Exemplary excipients include dicalcium phosphate, mannitol, lactose, starch, magnesium stearate, sodium saccharine, cellulose, magnesium carbonate or combinations thereof. A pharmaceutical composition may comprise different types of carriers or excipients depending on whether it is to be administered in solid, liquid or aerosol form, and whether it need to be sterile for such routes of administration.

For example, tablets and capsules for oral administration may be in unit dose presentation form, and may contain conventional excipients such as binding agents, for example syrup, acacia, gelatin, sorbitol, tragacanth, or polyvinylpyrrolidone; fillers, for example, lactose, sugar, maize-starch, calcium phosphate, sorbitol or glycine; tabletting lubricant, for example, magnesium stearate, talc, polyethylene glycol or silica; disintegrants, for example, potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example, sorbitol, syrup, methyl cellulose, glucose syrup, gelatin hydrogenated edible fats; emulsifying agents, for example, lecithin, sorbitan monooleate, or acacia; non-aqueous vehicles (which may include edible oils), for example, almond oil, fractionated coconut oil, oily esters such as glycerine, propylene glycol, or ethyl alcohol; preservatives, for example, methyl or propyl p-hydroxybenzoate or sorbic acid, and if desired conventional flavoring or coloring agents.

For topical application to the skin, a compound may be made up into a cream, lotion or ointment. Cream or ointment formulations which may be used for the drug are conventional formulations well known in the art, for example as described in standard textbooks of pharmaceutics such as the British Pharmacopoeia.

Compounds of the invention, such as a compound of Formula I, or a compound of Table 1 or of Examples 1-15, may also be formulated for inhalation, for example, as a nasal spray, or dry powder or aerosol inhalers. For delivery by inhalation, the compound is typically in the form of microparticles, which can be prepared by a variety of techniques, including spray-drying, freeze-drying and micronisation. Aerosol generation can be carried out using, for example, pressure-driven jet atomizers or ultrasonic atomizers, such as by using propellant-driven metered aerosols or propellant-free administration of micronized compounds from, for example, inhalation capsules or other "dry powder" delivery systems.

By way of example, a composition of the invention may be prepared as a suspension for delivery from a nebulizer or as an aerosol in a liquid propellant, for example, for use in a pressurized metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In some embodiments, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of, for example, greater than 90 µm.

In the case of an aerosol-based formulation, an example is:

Compound of the invention* 24 mg/canister
  *Such as a compound of Formula I, or a compound of Table 1 or of Examples 1-15.
Lecithin, NF Liq. Conc. 1.2 mg/canister
Trichlorofluoromethane, NF 4.025 g/canister
Dichlorodifluoromethane, NF 12.15 g/canister.

A compound, such as a compound of Formula I, or a compound of Table 1 or of Examples 1-15, may be dosed as described depending on the inhaler system used. In addition to the compound, the administration forms may additionally contain excipients as described above, or, for example, propellants (e.g., Frigen in the case of metered aerosols), surface-active substances, emulsifiers, stabilizers, preservatives, flavorings, fillers (e.g., lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g., Nebulator®, Volumatic®), and automatic devices emitting a puffer spray (Autohaler®), for metered aerosols, in the case of powder inhalers in particular, a number of technical solutions are available (e.g., Diskhaler®, Rotadisk®, Turbohaler® or the inhalers, for example, as described in U.S. Pat. No. 5,263,475, incorporated herein by reference). Additionally, compounds of the invention, such as a compound of Formula I, or a compound of Table 1 or of Examples 1-15, may be delivered in multi-chamber devices thus allowing for delivery of combination agents.

The compound, such as a compound of Formula I, or a compound of Table 1 or of Examples 1-15, may also be administered parenterally in a sterile medium. Depending on the vehicle and concentration used, the compound can either be suspended or dissolved in the vehicle. Advantageously, adjuvants such as a local anaesthetic, preservative or buffering agents can be dissolved in the vehicle.

Targeted Inhaled Drug Delivery

Optimisation of drugs for delivery to the lung by topical (inhaled) administration has been recently reviewed (Cooper, A. E. et al. Curr. Drug Metab. 2012, 13, 457-473). Due to limitations in the delivery device, the dose of an inhaled drug is likely to be low (approximately <1 mg/day) in humans which necessitates highly potent molecules. For compounds destined to be delivered via dry powder inhalation there is also a requirement to be able to generate crystalline forms of the compound that can be micronized to 1-5 μm in size. Additionally, the compound needs to maintain a sufficient concentration in the lung over a given time period so as to be able to exert a pharmacological effect of the desired duration, and for pharmacological targets where systemic inhibition of said target is undesired, to have a low systemic exposure. The lung has an inherently high permeability to both large molecules (proteins, peptides) as well as small molecules with concomitant short lung half-lives, thus it is necessary to attenuate the lung absorption rate through modification of one or more features of the compounds: minimizing membrane permeability, reducing dissolution rate, or introducing a degree of basicity into the compound to enhance binding to the phospholipid-rich lung tissue or through trapping in acidic sub-cellular compartments such as lysosomes (pH 5). Accordingly, in some embodiments, compounds of the present invention exhibit one or more of these features.

Methods of Treatment with and Uses of Janus Kinase Inhibitors

The compounds of the present invention, such as a compound of Formula I, or a compound of Table 1 or of Examples 1-15, inhibit the activity of a Janus kinase, such as JAK1 kinase. For example, a compound of the present invention, such as a compound of Formula I, or a compound of Table 1 or of Examples 1-15, inhibits the phosphorylation of signal transducers and activators of transcription (STATs) by JAK1 kinase as well as STAT mediated cytokine production. Compounds of the present invention, such as a compound of Formula I, or a compound of Table 1 or of Examples 1-15, are useful for inhibiting JAK1 kinase activity in cells through cytokine pathways, such as IL-6, IL-15, IL-7, IL-2, IL-4, IL-9, IL-10, IL-13, IL-21, G-CSF, IFNalpha, IFNbeta or IFNgamma pathways. Accordingly, in one embodiment is provided a method of contacting a cell with a compound of the present invention, such as a compound of Formula I, or a compound of Table 1 or of Examples 1-15, to inhibit a Janus kinase activity in the cell (e.g., JAK1 activity).

The compounds of the present invention, such as compounds of Formula I, or a compound of Table 1 or of Examples 1-15, can be used for the treatment of immunological disorders driven by aberrant IL-6, IL-15, IL-7, IL-2, IL-4, IL9, IL-10, IL-13, IL-21, G-CSF, IFNalpha, IFNbeta or IFNgamma cytokine signaling.

Accordingly, one embodiment includes compounds of of the present invention, such as a compound of Formula I, or a compound of Table 1 or of Examples 1-15, for use in therapy.

In some embodiments, there is provided use a compound of the present invention, such as a compound of Formula I, or a compound of Table 1 or of Examples 1-15, in the treatment of an inflammatory disease. Further provided is use of a compound of the present invention, such as a compound of Formula I, or a compound of Table 1 or of Examples 1-15, for the preparation of a medicament for the treatment of an inflammatory disease, such as asthma. Also provided is a compound of the present invention, such as a compound of Formula I, or a compound of Table 1 or of Examples 1-15, for use in the treatment of an inflammatory disease, such as asthma.

Another embodiment includes a method of preventing, treating or lessening the severity of a disease or condition, such as asthma, responsive to the inhibition of a Janus kinase activity, such as JAK1 kinase activity, in a patient. The method can include the step of administering to a patient a therapeutically effective amount of a compound of the present invention, such as a compound of Formula I, or a compound of Table 1 or of Examples 1-15. In one embodiment, the disease or condition responsive to the inhibition of a Janus kinase, such as JAK1 kinase, is asthma.

In one embodiment, the disease or condition is cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation (e.g., transplant rejection), immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the inflammatory disease is rheumatoid arthritis, psoriasis, asthma, inflammatory bowel disease, contact dermatitis or delayed hypersensitivity reactions. In one embodiment, the autoimmune disease is rheumatoid arthritis, lupus or multiple sclerosis.

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia.

In one embodiment, the disease is a myeloproliferative disorder. In one embodiment, the myeloproliferative disorder is polycythemia vera, essential thrombocytosis, myelofibrosis or chronic myelogenous leukemia (CML).

Another embodiment includes the use of a compound of the present invention, such as a compound of Formula I, or a compound of Table 1 or of Examples 1-15, for the manufacture of a medicament for the treatment of a disease described herein (e.g., an inflammatory disorder, an immunological disorder or cancer). In one embodiment, the invention provides a method of treating a disease or condition as described herein e.g., an inflammatory disorder, an immunological disorder or cancer) by targeting inhibition of a JAK kinase, such as JAK1.

Combination Therapy

The compounds of the present invention, such as a compound of Formula I, or a compound of Table 1 or of Examples 1-15, may be employed alone or in combination with other agents for treatment. The second compound of a pharmaceutical composition or dosing regimen typically has complementary activities to the compound of this invention such that they do not adversely affect each other. Such agents are suitably present in combination in amounts that are effective for the purpose intended. The compounds may be administered together in a unitary pharmaceutical composition or separately and, when administered separately this may occur simultaneously or sequentially. Such sequential administration may be close or remote in time.

For example, other compounds may be combined with compounds with which the invention is concerned for the prevention or treatment of inflammatory diseases, such as asthma. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: an adenosine A2A receptor antagonist; an anti-infective; a non-steroidal Glucocorticoid Receptor (GR Receptor) agonist; an antioxidant; a β2 adrenoceptor agonist; a CCR1 antagonist; a chemokine antagonist (not CCR1); a corticosteroid; a CRTh2 antagonist; a DP1 antagonist; a formyl peptide receptor antagonist; a histone deacetylase activator; a chloride channel hCLCA1 blocker; an epithelial sodium channel blocker (ENAC blocker; an inter-cellular adhesion molecule 1 blocker (ICAM blocker); an IKK2 inhibitor; a JNK inhibitor; a cyclooxygenase inhibitor (COX inhibitor); a lipoxygenase inhibitor; a leukotriene receptor antagonist; a dual β2 adrenoceptor agonist/M3 receptor antagonist (MABA compound); a MEK-1 inhibitor; a myeloperoxidase inhibitor (MPO inhibitor); a muscarinic antagonist; a p38 MAPK inhibitor; a phosphodiesterase PDE4 inhibitor; a phosphatidylinositol 3-kinase δ inhibitor (PI3-kinase δ inhibitor); a phosphatidylinositol 3-kinase γ inhibitor (PI3-kinase γ inhibitor); a peroxisome proliferator activated receptor agonist (PPARγ agonist); a protease inhibitor; a retinoic acid receptor modulator (RAR γ modulator); a statin; a thromboxane antagonist; a TLR7 receptor agonist; or a vasodilator.

In addition, compounds of the invention, such as a compound of Formula I, or a compound of Table 1 or of Examples 1-15, may be combined with: (1) corticosteroids, such as alclometasone dipropionate, amelometasone, beclomethasone dipropionate, budesonide, butixocort propionate, biclesonide, blobetasol propionate, desisobutyryl-ciclesonide, dexamethasone, dtiprednol dicloacetate, fluocinolone acetonide, fluticasone furoate, fluticasone propionate, loteprednol etabonate (topical) or mometasone furoate; (2) β2-adrenoreceptor agonists such as salbutamol, albuterol, terbutaline, fenoterol, bitolterol, carbuterol, clenbuterol, pirbuterol, rimoterol, terbutaline, tretoquinol, tulobuterol and long acting β2-adrenoreceptor agonists such as metaproterenol, isoproterenol, isoprenaline, salmeterol, indacaterol, formoterol (including formoterol fumarate), arformoterol, carmoterol, abediterol, vilanterol trifenate, olodaterol; (3) corticosteroid/long acting β2 agonist combination products such as salmeterol/fluticasone propionate (Advair®, also sold as Seretide®), formoterol/budesonide (Symbicort®), formoterol/fluticasone propionate (Flutiform®), formoterol/ciclesonide, formoterol/mometasone furoate, indacaterol/mometasone furoate, vilanterol trifenate/fluticasone furoate, or arformoterol/ciclesonide; (4) anticholinergic agents, for example, muscarinic-3 (M3) receptor antagonists such as ipratropium bromide, tiotropium bromide, aclidinium (LAS-34273), glycopyrronium bromide, umeclidinium bromide; (5) M3-antichobnergic/β2-adrenoreceptor agonist combination products such as vilanterol/umeclidinium (Anoro® Ellipta®), olodaterol/tiotropium bromide, glycopyrronium bromide/indacaterol (Ultibro®, also sold as Xotema®), fenoterol hydrobromide/ipratropium bromide (Berodual®), albuterol sulfate/ipratropium bromide (Combivent®), formoterol fumarate/glycopyrrolate, or aclidinium bromide/formoterol (6) dual pharmacology M3-antichobnergic/β2-adrenoreceptor agonists such as batefenterol succinate, AZD-2115 or LAS-190792; (7) leukotriene modulators, for example, leukotriene antagonists such as montelukast, zafirulast or pranlukast or leukotriene biosynthesis inhibitors such as zileuton, or LTB4 antagonists such as amelubant, or FLAP inhibitors such as fiboflapon, GSK-2190915; (8) phosphodiesterase-IV (PDE-IV) inhibitors (oral or inhaled), such as roflumilast, cilomilast, oglemilast, rolipram, tetomilast, AVE-8112, revamilast, CHF 6001; (9) antihistamines, for example, selective histamine-1 (H1) receptor antagonists such as fexofenadine, citirizine, loratidine or astemizole or dual H1/H3 receptor antagonists such as GSK 835726, or GSK 1004723; (10) antitussive agents, such as codeine or dextramorphan; (11) a mucolytic, for example, N-acetyl cysteine or fudostein; (12) a expectorant/mucokinetic modulator, for example, ambroxol, hypertonic solutions (e.g., saline or mannitol) or surfactant; (13) a peptide mucolytic, for example, recombinant human deoxyribonoclease I (domase-alpha and rhDNase) or helicidin; (14) antibiotics, for example azithromycin, tobramycin or aztreonam; (15) non-selective COX-1/COX-2 inhibitors, such as ibuprofen or ketoprofen; (16) COX-2 inhibitors, such as celecoxib and rofecoxib; (17) VLA-4 antagonists, such as those described in WO97/03094 and WO97/02289, each incorporated herein by reference; (18) TACE inhibitors and TNF-α inhibitors, for example anti-TNF monoclonal antibodies, such as Remicade® and CDP-870 and TNF receptor immunoglobulin molecules, such as Enbrel®; (19) inhibitors of matrix metalloprotease, for example MMP-12; (20) human neutrophil elastase inhibitors, such as BAY-85-8501 or those described in WO2005/026124, WO2003/053930 and WO06/082412, each incorporated herein by reference; (21) A2b antagonists such as those described in WO2002/42298, incorporated herein by reference; (22) modulators of chemokine receptor function, for example antagonists of CCR3 and CCR8; (23) compounds which modulate the action of other prostanoid receptors, for example, a thromboxane $A_2$ antagonist; DPI antagonists such as laropiprant or asapiprant CRTH2 antagonists such as OC000459, fevipiprant, ADC 3680 or ARRY 502; (24) PPAR agonists including PPAR alpha agonists (such as fenofibrate), PPAR delta agonists, PPAR gamma agonists such as pioglitazone, rosiglitazone and balaglitazone; (25) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (26) A2a agonists such as those described in EP1052264 and EP1241176; (27) CXCR2 or IL-8 antagonists such as AZD-5069, AZD-4721, danirixin; (28) IL-R signalling modulators such as kineret and ACZ 885; (29) MCP-1 antagonists such as ABN-912; (30) a p38 MAPK inhibitor such as BCT197, JNJ49095397, losmapimod or PH-797804; (31) TLR7 receptor agonists such as AZD 8848; (32) PI3-kinase inhibitors such as RV1729 or GSK2269557.

In some embodiments, the compounds of the present invention, such as a compound of Formula I, or a compound of Table 1 or of Examples 1-15, can be used in combination with one or more additional drugs, for example anti-hyperproliferative, anti-cancer, cytostatic, cytotoxic, anti-inflammatory or chemotherapeutic agents, such as those agents disclosed in U.S. Publ. Appl. No. 2010/0048557, incorporated herein by reference. A compound of the present invention, such as a compound of Formula I, or a compound of Table 1 or of Examples 1-15, can be also used in combination with radiation therapy or surgery, as is known in the art.

Articles of Manufacture

Another embodiment includes an article of manufacture (e.g., a kit) for treating a disease or disorder responsive to the inhibition of a Janus kinase, such as a JAK1 kinase. The kit can comprise:

(a) a first pharmaceutical composition comprising a compound of the present invention, such as a compound of Formula I, or a compound of Table 1 or of Examples 1-15; and (b) instructions for use.

In another embodiment, the kit further comprises:

(c) a second pharmaceutical composition, such as a pharmaceutical composition comprising an agent for treatment as described above, such as an agent for treatment of an inflammatory disorder, or a chemotherapeutic agent.

In one embodiment, the instructions describe the simultaneous, sequential or separate administration of said first and second pharmaceutical compositions to a patient in need thereof.

In one embodiment, the first and second compositions are contained in separate containers. In another embodiment, the first and second compositions are contained in the same container.

Containers for use include, for example, bottles, vials, syringes, blister pack, etc. The containers may be formed from a variety of materials such as glass or plastic. The container includes a compound of the present invention, such as a compound of Formula I, or a compound of Table 1 or of Examples 1-15, or composition thereof, which is effective for treating the condition and may have a sterile access port (for example the container may be an intravenous solution bag or a vial having a stopper pierceable by a hypodermic injection needle). The label or package insert indicates that the compound or composition is used for treating the condition of choice, such as asthma or cancer. In one embodiment, the label or package inserts indicates that the compound or composition can be used to treat a disorder. In addition, the label or package insert may indicate that the patient to be treated is one having a disorder characterized by overactive or irregular Janus kinase activity, such as overactive or irregular JAK1 activity. The label or package insert may also indicate that the compound or composition can be used to treat other disorders.

Alternatively, or additionally, the kit may further comprise a second (or third) container comprising a pharmaceutically acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of the present invention, and alternative methods for preparing the compounds are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

EXAMPLES

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

Abbreviations

DIPEA Diisopropylethylamine
DMF N,N-Dimethyl form amide
DMSO Dimethylsulfoxide
DMSO-d6 Deuterated dimethylsulfoxide
EtOAc Ethyl acetate
EtOH Ethanol
g Gram
HATU (O-(7-azabenzotriazol-1-yl)-N,N,N',N' tetramethyluroniumhexafluorophosphate)
HCl Hydrochloric acid
HM-N Isolute HM-N is a modified form of diatomaceous earth
L Litre
MeCN Acetonitrile
MeOH Methanol
mg Milligram
mL Millilitre
NaOH Sodium hydroxide
$Pd_2(dba)_3$ Tris(dibenzylidineacetone)palladium(0)
$Pd(dppf)Cl_2$ [1,1'-Bis(diphenylphosphino)ferrocene]-dichloropalladium-(II), complex with dichloromethane
$Pd(OAc)_2$ Palladium (II) acetate
$Pd(PPh_3)_4$ Tetrakis(triphenylphosphine)palladium(0)
RT Ambient temperature
THF Tetrahydrofuran
TFA Trifluoroacetic acid
TLC Thin layer chromatography
XantPhos 4,5-Bis(diphenylphosphino)-9,9-dimethylxanthene NMR Analytical Methods 1H NMR spectra were recorded at ambient temperature using a Bruker Avance III 300 (300 MHz) spectrometer with a 5 mm Broadband liquid probe BBFO with ATM+Z and a Bruker Avance III HD (400 MHz) spectrometer with a 5 mm Broadband liquid probe BBFO with ATM+Z. Chemical shifts are expressed in ppm relative to tetramethylsilane. The following abbreviations have been used: br=broad signal, s=singlet, d=doublet, dd=double doublet, t=triplet, q=quartet, m=multiplet.

LCMS Analytical Methods High Pressure Liquid Chromatography-Mass Spectrometry (LCMS) experiments to determine retention times ($R_T$) and associated mass ions were performed using one of the following methods with either UV detector monitoring at 220 nm and 254 nm or evaporative light scattering detection, and mass spectrometry scanning 110-800 amu in ESI+ ionization mode.

NMR Analytical Methods 1H NMR spectra were recorded at ambient temperature using a Bruker Avance III 300 (300 MHz) spectrometer with a 5 mm Broadband liquid probe BBFO with ATM+Z and a Bruker Avance III HD (400 MHz) spectrometer with a 5 mm Broadband liquid probe BBFO with ATM+Z. Chemical shifts are expressed in ppm relative to tetramethylsilane. The following abbreviations have been used: br=broad signal, s=singlet, d=doublet, dd=double doublet, t=triplet, q=quartet, m=multiplet.

LCMS Analytical Methods High Pressure Liquid Chromatography-Mass Spectrometry (LCMS) experiments to determine retention times ($R_T$) and associated mass ions were performed using one of the following methods with either UV detector monitoring at 220 nm and 254 nm or evaporative light scattering detection, and mass spectrometry scanning 110-800 amu in ESI+ ionization mode.

Method A

Experiments were performed on a SHIMADZU 20A HPLC with Shim-Pack XR-ODS column (50×3 mm, 2.2 μm particle size), elution with solvent A: water+0.05% trifluoroacetic acid; solvent B: acetonitrile+0.05% trifluoroacetic acid. Gradient:

| Gradient-Time | flow ml/min | % A | % B |
| --- | --- | --- | --- |
| 0.00 | 1.0 | 95 | 5 |
| 2.20 | 1.0 | 0 | 100 |
| 3.20 | 1.0 | 0 | 100 |
| 3.30 | 1.0 | 95 | 5 |

Detection-UV (220 and 254 nm) and ELSD

Method B

Experiments were performed on a SHIMADZU 20A HPLC with Shim-Pack XR-ODS column (50×3 mm, 2.2 μm particle size), elution with solvent A: water+0.05% trifluoroacetic acid; solvent B: acetonitrile+0.05% trifluoroacetic acid. Gradient:

| Gradient-Time | flow ml/min | % A | % B |
| --- | --- | --- | --- |
| 0.00 | 1.0 | 95 | 5 |
| 3.50 | 1.0 | 15 | 85 |
| 4.20 | 1.0 | 15 | 85 |
| 4.30 | 1.0 | 95 | 5 |

Detection-UV (220 and 254 nm) and ELSD

Method C

Experiments were performed on a SHIMADZU 20A HPLC with Poroshell HPH-$C_{18}$, column (50×3 mm, 2.7 μm particle size), elution with solvent A: water/5 mM $NH_4HCO_3$; solvent B: acetonitrile. Gradient:

| Gradient-Time | flow ml/min | % A | % B |
| --- | --- | --- | --- |
| 0.00 | 1.5 | 90 | 10 |
| 2.00 | 1.5 | 5 | 95 |
| 2.70 | 1.5 | 5 | 95 |
| 2.80 | 1.5 | 90 | 10 |

Detection-UV (220 and 254 nm) and ELSD

Method D

Experiments were performed on a SHIMADZU 20A HPLC with Shim-Pack XR-ODS column (50×3 mm, 2.2 μm particle size), elution with solvent A: water+0.05% trifluoroacetic acid; solvent B: acetonitrile+0.05% trifluoroacetic acid. Gradient:

| Gradient-Time | flow ml/min | % A | % B |
| --- | --- | --- | --- |
| 0.00 | 1.0 | 95 | 5 |
| 1.10 | 1.0 | 0 | 100 |
| 1.60 | 1.0 | 0 | 100 |
| 1.70 | 1.0 | 95 | 5 |

Detection-UV (220 and 254 nm) and ELSD

Method E

Experiments were performed on a SHIMADZU 20A HPLC with Shim-Pack XR-ODS column (50×3 mm, 2.2 μm particle size), elution with solvent A: water+0.05% trifluoroacetic acid; solvent B: acetonitrile+0.05% trifluoroacetic acid. Gradient:

| Gradient-Time | flow ml/min | % A | % B |
| --- | --- | --- | --- |
| 0.00 | 1.0 | 95 | 5 |
| 4.20 | 1.0 | 20 | 80 |
| 5.20 | 1.0 | 20 | 80 |
| 5.30 | 1.0 | 95 | 5 |

Detection-UV (220 and 254 nm) and ELSD

Method F

Experiments were performed on a SHIMADZU 20A HPLC with Shim-Pack XR-ODS column (50×3 mm, 2.2 μm particle size), elution with solvent A: water+0.05% trifluoroacetic acid; solvent B: acetonitrile+0.05% trifluoroacetic acid. Gradient:

| Gradient-Time | flow ml/min | % A | % B |
| --- | --- | --- | --- |
| 0.00 | 1.0 | 70 | 30 |
| 4.20 | 1.0 | 15 | 85 |
| 5.20 | 1.0 | 15 | 85 |
| 5.30 | 1.0 | 95 | 5 |

Detection-UV (220 and 254 nm) and ELSD

Method G

Experiments were performed on a SHIMADZU 20A HPLC with Shim-Pack XR-ODS column (50×3 mm, 2.2 μm particle size), elution with solvent A: water+0.05% trifluoroacetic acid; solvent B: acetonitrile+0.05% trifluoroacetic acid. Gradient:

| Gradient-Time | flow ml/min | % A | % B |
| --- | --- | --- | --- |
| 0.00 | 1.2 | 95 | 5 |
| 3.50 | 1.2 | 60 | 40 |
| 3.70 | 1.2 | 0 | 100 |
| 4.70 | 1.2 | 0 | 100 |
| 4.75 | 1.2 | 95 | 5 |

Detection-UV (220 and 254 nm) and ELSD

Method H

Experiments were performed on a SHIMADZU 20A HPLC with Shim-Pack XR-ODS column (50×3 mm, 2.2 μm particle size), elution with solvent A: water+0.05% trifluoroacetic acid; solvent B: acetonitrile+0.05% trifluoroacetic acid. Gradient:

| Gradient-Time | flow ml/min | % A | % B |
| --- | --- | --- | --- |
| 0.00 | 1.2 | 95 | 5 |
| 2.00 | 1.2 | 5 | 95 |

| Gradient-Time | flow ml/min | % A | % B |
|---|---|---|---|
| 2.70 | 1.2 | 5 | 95 |
| 2.75 | 1.2 | 95 | 5 |

Detection-UV (220 and 254 nm) and ELSD

Method I

Experiments performed on an Acquity UPLC (binary pump/PDA detector)+ZQ mass spectrometer using ESI as ionization source. The LC separation was using an Acquity UPLC BEH $C_{18}$ 1.7 µm, 100×2.1 mm column with a 0.4 ml/minute flow rate. Solvent A is water with 0.1% formic acid and solvent B is acetonitrile with 0.1% formic acid. The gradient consisted with 5% solvent B for 0.4 min, then 5-95% solvent B to 6 min and hold 95% B to 6.8 min. LC column temperature is 40° C. UV diode array 200-500 nm and mass spec full scan was applied to all experiments.

Method J

Experiments were performed on a Waters ZMD single quadrupole mass spectrometer with an electrospray source operating in positive and negative ion mode linked to a Waters 1525 LC system. Detection was achieved using a UV diode array detector and a Sedex 85 evaporative light scattering detector. The LC column was a Phenomenex Luna 3 micron C18(2) 30×4.6 mm. The flow rate was 2 mL/min. The initial solvent system was 95% water containing 0.1% formic acid (solvent A) and 5% acetonitrile containing 0.1% formic acid (solvent B) for 0.5 min followed by a gradient up to 5% solvent A and 95% solvent B over the next 4 min. The final solvent system was held constant for a further 1 min.

Method K

Experiments were performed on an Agilent 1290 UHPLC coupled with Agilent MSD (6140) mass spectrometer using ESI as ionization source (Phenomenex XB-C18, 1.7 uµm, 50×2.1 mm, 1.7 µm particle size), elution with solvent A: water+0.1% formic acid; solvent B: acetonitrile+0.1% formic acid. Gradient:

| Gradient-Time (min) | flow ml/min | % A | % B |
|---|---|---|---|
| 0 | 0.4 | 98 | 2 |
| 1.5 | 0.4 | 2 | 98 |
| 8.5 | 0.4 | 2 | 98 |
| 10 | 0.4 | 2 | 98 |
| 11.5 | 0.4 | 98 | 2 |

Detection-UV (200 nm, 254 nm)

Method L

Experiments were performed on an Agilent 1200 HPLC coupled with Agilent MSD (6140) mass spectrometer using ESI as ionization source (Agilent ZORBAX SB-C18, 1.8 µm particle size, 2.1*50 mm), elution with solvent A: water+0.1% formic acid; solvent B: acetonitrile+0.1% formic acid. Gradient:

| Min | flow(mL/min) | % A | % B |
|---|---|---|---|
| 0.0 | 0.4 | 97 | 3 |
| 7.0 | 0.4 | 5 | 95 |
| 8.5 | 0.4 | 5 | 95 |
| 8.7 | 0.4 | 97 | 3 |
| 10 | 0.4 | 97 | 3 |

Detection-UV (200 nm, 254 nm)

Preparation of Intermediate 1

3-(5-Chloro-2-methoxyphenyl)-1-methyl-1H-pyrazol-4-amine

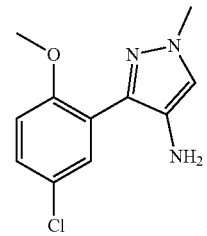 [SMILES: COc1ccc(Cl)cc1-c1nn(C)cc1N]

N,N-carbonyldiimidazole (1.64 g, 10.1 mmol) was added to a stirred solution of 5-chloro-2-methoxybenzoic acid (1.87 g, 10.0 mmol) in tetrahydrofuran (20 mL) and stirring was continued for 20 minutes to generate the acyl-imidazole. Separately, potassium ethyl malonate (4.08 g, 23.99 mmol) and magnesium chloride (1.15 g, 12.10 mmol) were suspended in tetrahydrofuran (20 mL). The acyl-imidazole solution was added to the magnesium chloride mixture. On complete addition, the mixture was heated at 50° C. for 1.5 hours. The reaction mixture was partitioned between ethyl acetate and water, and the organic portion dried over magnesium sulfate, filtered through a pad of celite, and concentrated to provide ethyl 3-(5-chloro-2-methoxyphenyl)-3-oxopropanoate (2.57 g, 101%) which was used without further purification. LC/MS (ESI): $[M+H]^+$=257.2.

A stirred mixture of ethyl 3-(5-chloro-2-methoxyphenyl)-3-oxopropanoate (10.0 mmol) and 1,1-dimethoxy-N,N-dimethylmethanamine (3.0 mL, 22.0 mmol) was heated at 90° C. for 2 hours. The mixture was allowed to cool to RT and evaporated. The crude product was purified by flash chromatography on silica gel (solvent gradient: 0-80% ethyl acetate in dichloromethane) to afford ethyl 2-(5-chloro-2-methoxybenzoyl)-3-(dimethylamino)acrylate (2.49 g, 80%). LC/MS (ESI): $[M+H]^+$=312.2.

A solution of ethyl 2-(5-chloro-2-methoxybenzoyl)-3-(dimethylamino)acrylate (2.49 g, 8.00 mmol) and hydrazine (0.40 mL, 13.0 mmol) in ethanol (20 mL) was heated at 70° C. for 2 hours. The mixture was allowed to cool to room temperature and the solvent evaporated to provide ethyl 5-(5-chloro-2-methoxyphenyl)-1H-pyrazole-4-carboxylate (2.24 g, 100%), which was used without further purification. LC/MS (ESI): $[M+H]^+$=281.3.

To a solution of ethyl 5-(5-chloro-2-methoxyphenyl)-1H-pyrazole-4-carboxylate (2.24 g, 8.00 mmol) in N,N-dimethylformamide (20 mL) was added cesium carbonate (3.417 g, 10.49 mmol) and iodomethane (0.60 mL, 9.60 mmol). The reaction mixture was heated at 40° C. for 4 hours, then additional iodomethane was added (0.2 mL, 3.21 mmol) and heating continued. After a further 2.5 hours, the reaction mixture was allowed to cool to room temperature and partitioned between ethyl acetate and water. The organic layer was dried over magnesium sulfate and concentrated. The crude product was purified by flash chromatography on silica gel (solvent gradient: 0-35% ethyl acetate in dichloromethane) to yield a 1:1 mixture of regioisomeric products, ethyl 3-(5-chloro-2-methoxyphenyl)-1-methyl-1H-pyrazole-4-carboxy late and ethyl 5-(5-chloro-2-methoxyphenyl)-1-methyl-1H-pyrazole-4-carboxylate (2.18 g, 92%). LC/MS (ESI): $[M+H]^+$=295.1.

A mixture of ethyl 3-(5-chloro-2-methoxyphenyl)-1-methyl-1H-pyrazole-4-carboxylate and ethyl 5-(5-chloro-2-methoxyphenyl)-1-methyl-1H-pyrazole-4-carboxylate (1:1 mixture of regioisomers, 2.18 g, 7.40 mmol) and 1.0 M aqueous sodium hydroxide (12 mL, 20.0 mmol) in ethanol (15 mL) was heated at 50° C. for 14 hours. The reaction mixture was allowed to cool to room temperature and evaporated. The residue was diluted with water and the pH adjusted to 2 by the addition of 1.0 M aqueous phosphoric acid. The aqueous phase was extracted twice with dichloromethane. The combined organic extract was dried over $MgSO_4$ and concentrated to yield the corresponding carboxylic acid (1.79 g, 91%) of which was carried forward immediately. LCMS (ESI) M+H=267.2. To a solution of the acid in dioxane (15 mL) was added triethylamine (2.0 mL, 14 mmol) and diphenylphosphonic azide (1.6 mL, 7.4 mmol). The reaction mixture was stirred at room temperature for 1 hour, then heated to 90° C. and tert-butyl alcohol (15 mL) was added. After stirring at 90° C. for 2.5 hours, the mixture was allowed to cool to room temperature, the solvent was evaporated and the residue partitioned between ethyl acetate and water. The organic layer was washed with brine, dried over magnesium sulfate, and concentrated. The crude product was purified by flash chromatography on silica gel (solvent gradient: 0-50% ethyl acetate in dichloromethane), separating the two regioisomers to obtain:

tert-butyl 3-(5-chloro-2-methoxyphenyl)-1-methyl-1H-pyrazol-4-ylcarbamate (543 mg, 48%). LC/MS (ESI): $[M+H]^+$=338.3; $^1$H NMR (400 MHz, $CDCl_3$): δ: 7.84 (s, 1H), 7.39 (d, 1H), 7.23 (s, 1H), 6.96 (d, 1H), 5.92 (s, 1H), 3.89 (m, 6H), 1.48 (s, 9H).

tert-butyl 5-(5-chloro-2-methoxyphenyl)-1-methyl-1H-pyrazol-4-yl carbamate (774 mg, 68%). LC/MS (ESI): $[M+H]^+$=338.3; $^1$H NMR (400 MHz, $CDCl_3$): δ: 7.84 (s, 1H), 7.59 (s, 1H), 7.29 (d, 1H), 6.93 (d, 1H), 3.89 (m, 6H), 1.48 (s, 9H).

To a stirred solution of tert-butyl 3-(5-chloro-2-methoxyphenyl)-1-methyl-1H-pyrazol-4-ylcarbamate (0.23 g, 0.68 mmol) in 1,2-dichloroethane (5 mL) was added hydrogen chloride (2.0 mL of a 4.0 M solution in 1,4-dioxane, 8.0 mmol). The reaction mixture was stirred at room temperature for 3.5 hours and then evaporated to dryness. The solid residue was partitioned between dichloromethane and a saturated aqueous solution of sodium bicarbonate. The aqueous portion was extracted once more with dichloromethane, and the combined organic extract dried over magnesium sulfate and concentrated. The crude product was purified via flash chromatography on silica gel (solvent gradient: 0-100% ethyl acetate in dichloromethane) to yield 3-(5-chloro-2-methoxyphenyl)-1-methyl-1H-pyrazol-4-amine (65.9 mg, 41%). LC/MS (ESI): $[M+H]^+$=238.2; $^1$H NMR (400 MHz, $CDCl_3$): δ:7.53 (s, 1H), 7.28 (d, 1H), 7.02 (s, 1H), 6.91 (d, 1H), 3.91 (d, 2H), 3.87 (s, 3H), 3.84 (s, 3H).

Preparation of Intermediate 2

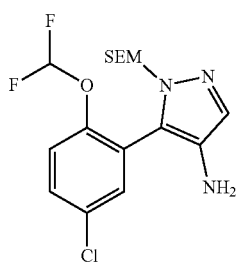 [SMILES: C[Si](C)(C)CCOCn1ncc(N)c1-c1cc(Cl)ccc1OC(F)F]

5-(5-chloro-2-(difluoromethoxy)phenyl)-1-((2-(trimethylsilyl)ethoxy)methyl)-1H-pyrazol-4-amine To a solution of 2-bromo-4-chlorophenol (4.98 g, 24.0 mmol) in DMF (25 mL) was added sodium chlorodifluoroacetate (8.42 g, 55.2 mmol), cesium carbonate (10.97 g, 33.67 mmol) and water (2.5 mL). The reaction was stirred at 100° C. for 16 hours. The reaction mixture was partitioned between ethyl acetate and water, the organic portion washed with brine, dried ($MgSO_4$), and evaporated. The crude product was purified by flash chromatography on silica eluting with 0-20% EtOAc in heptanes to yield 2-bromo-4-chloro-1-(difluoromethoxy)benzene (2.98 g, 48%) as a clear, colorless oil. LCMS (ESI) no m/z signal; $^1$H NMR (400 MHz, DMSO-$d_6$): δ 7.90 (d, 1H), 7.54 (dd, 1H), 7.38 (d, 1H), 7.28 (t, 1H).

To a solution of 4-nitro-1-(2-trimethylsilanylethoxymethyl)-1H-pyrazole (preparation described in WO2011003065) (46.5 g, 191 mmol) in DMA (350 mL) was added 2-bromo-4-chloro-1-difluoromethoxybenzene (64.0 g, 248 mmol), palladium (II) acetate (2.15 g, 9.6 mmol), di-(adamantyl)-n-butylphosphine (5.0 g, 13.4 mmol), potassium carbonate (79.2 g, 573 mmol) and trimethylacetic acid (5.27 g, 51.6 mmol). The mixture was degassed with nitrogen for 10 minutes then heated at 130° C. for 8 hours. The reaction mixture was allowed to cool to room temperature, diluted with ethyl acetate and washed with water and brine, dried ($MgSO_4$), filtered and evaporated. The resultant crude material was purified by flash chromatography on silica eluting with 0-10% EtOAc in cyclohexane to afford 5-(5-chloro-2-difluoromethoxyphenyl)-4-nitro-1-(2-trimethylsilanylethoxymethyl)-1H-pyrazole (62.4 g, 78%). $^1$H NMR (400 MHz, $CDCl_3$): δ 8.24 (s, 1H), 7.52-7.53 (m, 2H), 6.39 (t, 1H), 5.29-5.30 (m, 2H), 3.63-3.64 (m, 2H), 0.90 (s, 9H).

To a solution of 5-(5-chloro-2-difluoromethoxyphenyl)-4-nitro-1-(2-trimethylsilanylethoxymethyl)-1H-pyrazole (62 g, 148 mmol) in ethanol (600 mL) was added water (200 mL), ammonium chloride (32 g, 590 mmol) and iron powder (41 g, 740 mmol). The mixture was heated at 80° C. for 2 hours then allowed to cool to room temperature. The residual solid was removed by filtration through Celite®. The filtrate was evaporated under reduced pressure, diluted with water and extracted twice with DCM. The combined organic extracts were washed with water and brine, dried ($MgSO_4$) and evaporated to afford a dark oil. The oil was purified by flash chromatography on silica eluting with 0-25% EtOAc in DCM. Appropriate fractions were collected and the solvent removed in-vacuo to afford 5-(5-chloro-2-difluoromethoxyphenyl)-1-(2-trimethylsilanyl-ethoxymethyl)-1H-pyrazol-4-ylamine (30.8 g, 54%) as a brown oil. $^1$H NMR (400 MHz, $CDCl_3$) δ 7.56 (d, 1H), 7.44 (dd, 1H), 7.34 (s, 1H), 7.30-7.25 (m, 1H), 6.37 (t, 1H), 5.29 (s, 2H), 3.56 (t, 2H), 0.88 (dd, 2H), 0.00 (s, 9H).

A solution of 5-(5-chloro-2-difluoromethoxyphenyl)-1-(2-trimethylsilanyl-ethoxymethyl)-1H-pyrazol-4-ylamine (60.0 g, 154 mmol) in THF (100 mL) was added dropwise over 30 minutes to an ice/water cooled mixture of pyrazolo[1,5-a]pyrimidine-3-carbonyl chloride (27.8 g, 153 mmol), and DIPEA (49.5 g, 383 mmol) in THF (300 mL). On complete addition the mixture was left to stir at room temperature for 1 hour. The solvent was evaporated and the residue diluted with 0.5 N aqueous HCl and extracted with ethyl acetate. The combined organic extract was passed through Celite® to remove the residual solid and the filtrate washed with 1M aqueous $K_2CO_3$, water and brine, dried ($Na_2SO_4$) and evaporated to give a red solid. The solid was triturated with 10% diethyl ether in cyclohexane. The solid was collected by filtration, washed with 1:1 diethyl ether in cyclohexane and left to air dry to afford pyrazolo[1,5-a]pyrimidine-3-carboxylic acid [5-(5-chloro-2-difluoromethoxyphenyl)-1-(2-trimethylsilanylethoxymethyl)-1H-pyrazol-4-yl]amide (59.2 g, 73%) as an off-white solid. $^1$H NMR (300 MHz, CDCl$_3$): δ 9.61 (s, 1H), 8.77-8.78 (m, 1H), 8.51 (dd, 1H), 8.36 (s, 1H), 7.65 (d, 1H), 7.52 (dd, 1H), 7.36 (d, 1H), 7.29 (s, 1H), 7.01 (dd, 1H), 6.42 (t, 1H), 5.39-5.41 (m, 2H), 3.60-3.64 (m, 2H), 0.87-0.89 (m, 2H), 0.09 (s, 9H).

Example 1

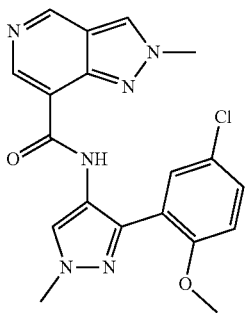 [SMILES: COc1ccc(Cl)cc1-c1nn(C)cc1NC(=O)c1cncc2cn(C)nc12]

N-(3-(5-Chloro-2-methoxyphenyl)-1-methyl-1H-pyrazol-4-yl)-2-methyl-2H-pyrazolo[4,3-c]pyridine-7-carboxamide To a solution of 4-azido-5-bromonicotinaldehyde (0.50 g, 2.2 mmol) in THF (10 mL) was added methylamine (2M in THF, 9.0 mL, 18 mmol) and anhydrous sodium sulfate. The mixture was stirred overnight at room temperature. The solid was removed by filtration and the filtrate evaporated to give crude 1-(4-azido-5-bromopyridin-3-yl)-N-methylmethanimine (0.578 g, assume quantitative). The imine was dissolved in toluene (50 mL) and heated under reflux for 4 h. The cooled reaction mixture was evaporated and the residue partitioned between dichloromethane and dilute sodium hydrogen carbonate. The aqueous phase was extracted with more dichloromethane and the combined organic extract was dried over anhydrous sodium sulfate and concentrated under reduced pressure. The residue was purified by chromatography on silica (10-100% ethyl acetate in dichloromethane) to afford 7-bromo-2-methyl-2H-pyrazolo[4,3-c]pyridine (0.18 g, 38%) as a white solid. TLC: Rf=0.07; DCM/EA=1/1.

Carbon monoxide was passed through a mixture of 7-bromo-2-methyl-2H-pyrazolo[4,3-c]pyridine (0.179 g, 0.844 mmol), palladium(II) acetate (15.1 mg, 0.067 mmol), Xantphos (78 mg, 0.135 mmol), triethylamine (1.5 mL), methanol (0.7 mL) and toluene (3 mL) before placing under a balloon of carbon monoxide and stirring at 70° C. for 18 hours. The cooled reaction mixture was evaporated and the residue partitioned between ethyl acetate and water. The aqueous phase was extracted with more ethyl acetate and the combined organic extract was washed with brine, dried over anhydrous sodium sulfate and concentrated under reduced pressure. The residue was purified by chromatography on silica (2-10% 2M ammonia in methanol in dichloromethane). Appropriate fractions were combined and evaporated to afford methyl 2-methyl-2H-pyrazolo[4,3-c]pyridine-7-carboxylate (30 mg, 19%) as a buff solid. $^1$H NMR (300 MHz, CDCl$_3$): δ 9.28 (s, 1H), 8.99 (s, 1H), 8.26 (s, 1H), 4.35 (s, 3H), 4.04 (s, 3H).

To a solution of methyl 2-methyl-2H-pyrazolo[4,3-c]pyridine-7-carboxylate (30 mg, 0.157 mmol) in THF (3 mL) was added a solution of lithium hydroxide hydrate (13.2 mg, 0.314 mmol) in water (0.5 mL). The mixture was stirred at room temperature for 16 hours. 1M HCl (0.314 mL) was added and the mixture evaporated to dryness. DMF was added and the resulting solution was evaporated to afford crude 2-methyl-2H-pyrazolo[4,3-c]pyridine-7-carboxylic acid. This acid was dissolved in DMF (2 mL), 3-(5-chloro-2-methoxyphenyl)-1-methyl-1H-pyrazol-4-amine (41 mg, 0.173 mmol) and N,N-diisopropylethylamine (0.0816 mL, 0.471 mmol) were added followed by portionwise addition of HATU (90 mg, 0.236 mmol) over 3 min. The mixture was stirred at room temperature for 1 h then partitioned between ethyl acetate and water. The aqueous phase was extracted with more ethyl acetate and the combined organic extract was washed with brine, dried over anhydrous sodium sulfate and concentrated under reduced pressure. The residue was purified by chromatography on silica (solvent gradient: 2-14% methanol in ethyl acetate). NMR showed an impurity of methyl 2-methyl-2H-pyrazolo[4,3-c]pyridine-7-carboxylate. The product was dissolved in THF (1.5 mL) and a solution of lithium hydroxide hydrate (3 mg, 0.071 mmol) in water (0.2 mL) was added. The mixture was stirred at room temperature for 2 h, then evaporated to dryness. The residue was purified by chromatography on silica (solvent gradient: 2-8% 2M ammonia in methanol in dichloromethane) and then triturated from isopropyl acetate to afford methyl 2-methyl-2H-pyrazolo[4,3-c]pyridine-7-carboxylate (21.8 mg, 35%) as a white solid. LC/MS (Method I, ESI): [M+H]$^+$=396.8, R$_T$=2.92 min; $^1$H NMR (400 MHz, DMSO-d$_6$): δ 10.32 (s, 1H), 9.34 (s, 1H), 8.89 (s, 1H), 8.88 (s, 1H), 8.41 (s, 1H), 7.54 (dd, J=8.9, 2.7 Hz, 1H), 7.41 (d, J=2.7 Hz, 1H), 7.34 (d, J=8.9 Hz, 1H), 4.14 (s, 3H), 3.92 (s, 3H), 3.68 (s, 3H).

Example 2

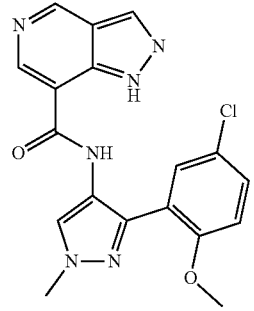 [SMILES: COc1ccc(Cl)cc1-c1nn(C)cc1NC(=O)c1cncc2c[nH]nc12]

N-(3-(5-Chloro-2-methoxyphenyl)-1-methyl-1H-pyrazol-4-yl)-1H-pyrazolo[4,3-c]pyridine-7-carboxamide To a solution of 4-azido-5-bromonicotinaldehyde (0.50 g, 2.2 mmol) in THF (13 mL) was added a solution of 4-methoxybenzylamine (0.343 mL, 2.64 mmol) in THF (2 mL). Anhydrous sodium sulfate was added and the mixture was stirred at room temperature for 3 hours. The mixture was filtered and the filtrate evaporated to give crude 1-(4- azido-5-bromopyridin-3-yl)-N-(4-methoxybenzyl)methanimine. This imine was dissolved in toluene (45 mL) and heated at reflux for 2.5 hours. The cooled reaction mixture was evaporated and the residue was purified by chromatography on silica (solvent gradient: 50-100% ethyl acetate in dichloromethane). Appropriate fractions were combined and evaporated to afford 7-bromo-2-(4-methoxybenzyl)-2H-pyrazolo[4,3-c]pyridine (0.48 g, 69%) as a white solid. $^1$H NMR (300 MHz, CDCl$_3$): δ 8.98 (s, 1H), 8.42 (s, 1H), 8.02 (s, 1H), 7.32 (d, J=8.8 Hz, 2H), 6.93 (d, J=8.8 Hz, 2H), 5.62 (s, 2H), 3.82 (s, 3H).

Carbon monoxide was passed through a mixture of 7-bromo-2-(4-methoxybenzyl)-2H-pyrazolo[4,3-c]pyridine (0.48 g, 1.51 mmol), palladium(II) acetate (27 mg, 0.12 mmol), Xantphos (139 mg, 0.24 mmol), triethylamine (2.7 mL), methanol (1.25 mL) and toluene (5.5 mL) before placing under a balloon of carbon monoxide and stirring at 70° C. for 20 hours. The cooled reaction mixture was partitioned between ethyl acetate and water. The aqueous phase was extracted with more ethyl acetate and the combined organic extract was washed with brine, dried over anhydrous sodium sulfate and concentrated under reduced pressure. The residue was purified by chromatography on silica (solvent gradient: 0-100% methyl acetate in ethyl acetate) to afford methyl 2-(4-methoxybenzyl)-2H-pyrazolo[4,3-c]pyridine-7-carboxylate (0.31 g, 69%) as a buff solid. $^1$H NMR (300 MHz, CDCl$_3$): δ 9.21 (s, 1H), 8.98 (s, 1H), 8.01 (s, 1H), 7.34 (d, J=8.7 Hz, 2H), 6.94 (d, J=8.7 Hz, 2H), 5.67 (s, 2H), 4.05 (s, 3H), 3.83 (s, 3H).

To a solution of methyl 2-(4-methoxybenzyl)-2H-pyrazolo[4,3-c]pyridine-7-carboxylate (0.10 g, 0.336 mmol) in THF (5 mL) was added a solution of lithium hydroxide hydrate (28.3 mg, 0.673 mmol) in water (1 mL). The mixture was stirred at room temperature for 2 hours. 1M HCl (0.67 mL) was added and the mixture evaporated to dryness. DMF was added and evaporated to afford crude 2-(4-methoxybenzyl)-2H-pyrazolo[4,3-c]pyridine-7-carboxylic acid. This acid was dissolved in DMF (3 mL), 3-(5-chloro-2-methoxyphenyl)-1-methyl-1H-pyrazol-4-amine (87.7 mg, 0.369 mmol) and N,N-diisopropylethylamine (0.175 mL, 1.0 mmol) were added followed by HATU (0.193 g, 0.508 mmol) portionwise over 5 min. The mixture was stirred at room temperature for 1 h, then partitioned between ethyl acetate and water. The aqueous phase was extracted with more ethyl acetate and the combined organic extracts were washed with brine, dried over anhydrous sodium sulfate and concentrated under reduced pressure. The residue was purified by chromatography on silica (solvent gradient: 2-12% methanol in ethyl acetate). Appropriate fractions were combined and evaporated and the resultant residue triturated from methanol to afford N-(3-(5-chloro-2-methoxyphenyl)-1-methyl-1H-pyrazol-4-yl)-2-(4-methoxybenzyl)-2H-pyrazolo[4,3-c]pyridine-7-carboxamide (54.2 mg, 32%) as a yellow solid. LC/MS (ESI): [M+H]$^+$=502.9, R$_T$=3.69 min.

A solution of N-(3-(5-chloro-2-methoxyphenyl)-1-methyl-1H-pyrazol-4-yl)-2-(4-methoxybenzyl)-2H-pyrazolo[4,3-c]pyridine-7-carboxamide (29 mg, 0.0576 mmol) in trifluoroacetic acid (0.5 mL) was heated at 100° C. under microwave irradiation for 1 hour. Toluene was added to the cooled reaction mixture and evaporated. The residue was partitioned between dichloromethane and dilute sodium hydrogen carbonate. The aqueous phase was extracted with more dichloromethane and the combined organic extract was dried over anhydrous sodium sulfate and concentrated under reduced pressure. The residue was purified by chromatography on silica (solvent gradient: 1-8% 2M ammonia in methanol in dichloromethane) to afford N-(3-(5-chloro-2-methoxyphenyl)-1-methyl-1H-pyrazol-4-yl)-1H-pyrazolo[4,3-c]pyridine-7-carboxamide (17.7 mg, 80%) as a white solid. LC/MS (Method I, ESI): [M+H]$^+$=382.8, R$_T$=2.82 min; $^1$H NMR (400 MHz, DMSO-d$_6$): δ 9.96 (brs, 1H), 9.26 (s, 1H), 8.84 (s, 1H), 8.88 (s, 1H), 8.45 (brs, 1H), 8.22 (s, 1H), 7.42 (s, 2H), 7.15-7.12 (m, 1H), 3.92 (s, 3H), 3.73 (s, 3H).

Example 3

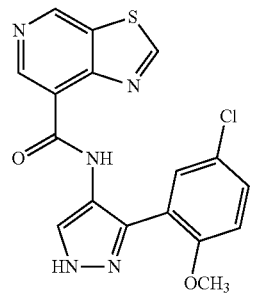 [SMILES: COc1ccc(Cl)cc1-c1n[nH]cc1NC(=O)c1cncc2scnc12]

N-(3-(5-Chloro-2-methoxyphenyl)-1H-pyrazol-4-yl)thiazolo[5,4-c]pyridine-7-carboxamide A sealed reaction vessel charged with 4-amino-3,5-dibromopyridine (643 mg, 2.55 mmol, 1 equiv) and potassium ethyl xanthogenate (495 mg, 3.09 mmol, 1.21 equiv) in N,N-dimethylacetamide (8.0 mL) was heated with microwave irradiation at 160° C. for 20 min. Additional potassium ethyl xanthogenate (0.490 g, 3.06 mmol, 1.20 equiv) was added to the mixture, and the resulting solution was heated with microwave irradiation at 160° C. for a further 20 min. The reaction mixture was cooled to 0° C. before the addition of iodomethane (382 µL, 6.13 mmol, 2.40 equiv). After 20 min, the reaction was concentrated in vacuo and the resultant residue purified by flash column chromatography (solvent: 2:1 heptane/ethyl acetate). Appropriate fractions were combined and evaporated to afford 7-bromo-2-(methylthio)thiazolo[5,4-c]pyridine (505 mg, 75.7%) as a tan solid. $^1$H NMR (500 MHz, CDCl$_3$): δ: 8.88 (s, 1H), 8.66 (s, 1H), 2.85 (s, 3H).

A round bottomed flask charged with 7-bromo-2-(methylthio)thiazolo[5,4-c]pyridine (0.240 g, 0.919 mmol, 1 equiv), palladium acetate (23.5 mg, 0.105 mmol, 0.114 equiv), 4,5-bis(diphenylphosphino)-9,9-dimethylxanthene (77 mg, 0.13 mmol, 0.14 equiv), and triethylamine (0.64 mL, 4.6 mmol, 5.0 equiv) in methanol (2 mL) and toluene (6 mL) was evacuated and purged with carbon dioxide (5×). The reaction was heated at 70° C. under carbon dioxide (1 atm) for 20 hours. The cooled reaction mixture was concentrated in vacuo, and the resulting residue was purified by flash column chromatography (solvent: 1:1 heptane/ethyl acetate). Appropriate fractions were combined and evaporated to provide methyl 2-(methylthio)thiazolo[5,4-c]pyridine-7-carboxylate (162 mg, 73.4%) as a yellow solid. $^1$H NMR (400 MHz, CDCl$_3$): δ: 9.11 (s, 1H), 9.10 (s, 1H), 4.02 (s, 3H), 2.88 (s, 3H).

1.0 M aqueous potassium hydroxide (0.634 mL, 0.634 mmol, 1.10 equiv) was added dropwise at room temperature to a suspension of methyl 2-(methylthio)thiazolo[5,4-c]pyridine-7-carboxylate (139 mg, 0.577 mmol, 1 equiv) in ethanol (6.0 mL). The mixture was allowed to stir for 5 hours then concentrated in vacuo. The resulting residue was lyophilized from acetonitrile to provide crude potassium 2-(methylthio)thiazolo[5,4-c]pyridine-7-carboxylate which was used without further purification.

To a solution of crude potassium 2-(methylthio)thiazolo[5,4-c]pyridine-7-carboxylate (~0.577 mmol, 1 equiv), 5-(5-chloro-2-methoxyphenyl)-1-((2-(trimethylsilyl)ethoxy)-methyl)-1H-pyrazol-4-amine (0.340 g, 0.961 mml, 1.66 equiv, Hanan, E. J., et al. *J. Med. Chem.* 2012, 55, 10090) and N,N-diisopropylethylamine (0.200 µL, 1.15 mmol, 2.00 equiv) in N,N-dimethylformamide (6.0 mL) was sequentially added (7-azabenzotriazol-1-yloxy)tripyrrolidinophosphonium hexafluorophosphate (537 mg, 1.04 mmol, 1.80 equiv) and 4-dimethylaminopyridine (7 mg, 0.06 mmol, 0.1 equiv) at room temperature. After 3 h, the reaction was concentrated in vacuo and the residue was dissolved in ethyl acetate (30 mL). The organic layer was washed with a 1:1 mixture of saturated aqueous sodium chloride solution and water (20 mL), dried over anhydrous sodium sulfate, filtered, and concentrated. The residue was purified by flash column chromatography (solvent: ethyl acetate). Appropriate fractions were combined and evaporated to afford N-(5-(5-chloro-2-methoxyphenyl)-1-((2-(trimethylsilyl)ethoxy)methyl)-1H-pyrazol-4-yl)-2-(methylthio)thiazolo[5,4-c]pyridine-7-carboxamide (316 mg, 97%) as a yellow oil.

A sealed reaction tube charged with N-(5-(5-chloro-2-methoxyphenyl)-1-((2-(trimethylsilyl)ethoxy)methyl)-1H-pyrazol-4-yl)-2-(methylthio)thiazolo[5,4-c]pyridine-7-carboxamide (324 mg, 0.577 mmol, 1 equiv) and isopropanol saturated with ammonia (5 mL, prepared by bubbling ammonia into isopropanol at 0° C. for 20 min) was heated with microwave irradiation at 100° C. for 3.5 hours. The cooled reaction mixture was concentrated in vacuo, and the resulting residue was purified by flash column chromatography (solvent: 95:5 dichloromethane/methanol). Appropriate fractions were combined and evaporated to afford 2-amino-N-(5-(5-chloro-2-methoxyphenyl)-1-((2-(trimethylsilyl)ethoxy)methyl)-1H-pyrazol-4-yl)thiazolo[5,4-c]pyridine-7-carboxamide (121 mg, 39%) as a light yellow solid. LCMS [M+H]$^+$=531.2; $^1$H NMR (CDCl$_3$, 500 MHz): δ: 11.11 (s, 1H), 9.30 (s, 1H), 8.80 (s, 1H), 8.52 (s, 1H), 7.54 (d, J=2.6 Hz, 1H), 7.48 (dd, J=8.8, 2.6 Hz, 1H), 7.02 (d, J=8.8 Hz, 1H), 5.57 (br s, 2H), 5.36 (A of AB, J$_{AB}$=11.1 Hz, 1H), 5.30 (B of AB, J$_{AB}$=11.2 Hz, 1H), 3.75 (s, 3H), 3.70 (m, 1H), 3.52 (m, 2H), 0.80 (m, 2H), −0.07 (s, 9H).

A suspension of 2-amino-N-(5-(5-chloro-2-methoxyphenyl)-1-((2-(trimethylsilyl)-ethoxy)methyl)-1H-pyrazol-4-yl)thiazolo[5,4-c]pyridine-7-carboxamide (62 mg, 0.12 mmol, 1 equiv) and amyl nitrite (175 mg, 1.49 mmol, 12.8 equiv) in 1,4-dioxane (4.5 mL) was heated at 85° C. After 50 min, additional amyl nitrite (0.330 mL, 2.46 mmol, 20.5 equiv) was added, and the suspension was maintained at 85° C. for another 4.5 hours. The reaction was concentrated in vacuo, and the resulting residue was purified by flash column chromatography (solvent: 95:5 dichloromethane/methanol). Appropriate fractions were combined and evaporated to afford N-(5-(5-chloro-2-methoxyphenyl)-1-((2-(trimethylsilyl)ethoxy)methyl)-1H-pyrazol-4-yl)thiazolo[5,4-c]pyridine-7-carboxamide (31 mg, 51%). LCMS [M+H]$^+$=516.

A solution of N-(5-(5-chloro-2-methoxyphenyl)-1-((2-(trimethylsilyl)-ethoxy)methyl)-1H-pyrazol-4-yl)thiazolo[5,4-c]pyridine-7-carboxamide (48.3 mg, 0.0936 mmol, 1 equiv) in 6N aqueous hydrochloric acid (1.5 mL) and ethanol (3 mL) was heated at 70° C. After 1 hour, the reaction was allowed to cool to room temperature, concentrated in vacuo, and the resulting residue was partitioned between ethyl acetate (5 mL), saturated aqueous sodium bicarbonate solution (5 mL), and saturated aqueous sodium chloride solution (5 mL). The organic layer was separated, and the aqueous was extracted with ethyl acetate (2×5 mL). The combined organic layer was dried over anhydrous sodium sulfate, filtered, and concentrated. The residue was purified by flash column chromatography (solvent: 95:5 dichloromethane/methanol). Appropriate fractions were combined and evaporated to afford N-(3-(5-chloro-2-methoxyphenyl)-1H-pyrazol-4-yl)thiazolo[5,4-c]pyridine-7-carboxamide (14.4 mg, 40%) as a light yellow solid. LCMS (Method L, ESI): [M+H]$^+$=386.0, R$_T$=3.97 min; $^1$H NMR (CDCl$_3$, 500 MHz): δ 11.45 (s, 1H), 9.58 (s, 1H), 9.42 (s, 1H), 9.33 (s, 1H), 8.57 (s, 1H), 7.73 (d, J=2.3 Hz, 1H), 7.38 (dd, J=8.8, 2.4 Hz, 1H), 7.00 (d, J=8.8 Hz, 1H), 3.85 (s, 3H).

Example 4

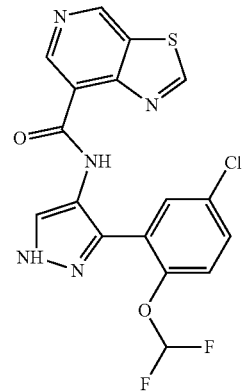 [SMILES: O=C(Nc1c[nH]nc1-c1cc(Cl)ccc1OC(F)F)c1cncc2scnc12]

N-(3-(5-chloro-2-(difluoromethoxy)phenyl)-1H-pyrazol-4-yl)thiazolo[5,4-c]pyridine-7-carboxamide To a solution of 5-[5-chloro-2-(difluoromethoxy)phenyl]-1-[[2-(trimethylsilyl)ethoxy]methyl]-1H-pyrazol-4-amine (2.40 g, 6.15 mmol) in DMA (30 mL) was added 2-(methylsulfanyl)-[1,3]thiazolo[5,4-c]pyridine-7-carboxylic acid (920 mg, 4.06 mmol), PyAOP (3.20 g, 6.13 mmol), 4-dimethylaminopyridine (100 mg, 0.819 mmol) and DIPEA (1.60 g, 12.3 mmol). The resulting solution was stirred at 45° C. for 2 hours. The reaction mixture was allowed to cool to room temperature and partitioned between water and ethyl acetate. The organic phase was washed with brine, dried and concentrated under vacuum. The residue was purified by flash chromatography on silica gel (solvent gradient: 1/2-3/2 ethyl acetate/petroleum ether). The appropriate fractions were combined and concentrated under vacuum to afford N-[5-[5-chloro-2-(difluoromethoxy)phenyl]-1-[[2-(trimethylsilyl)ethoxy]-methyl]-1H-pyrazol-4-yl]-2-(methylsulfanyl)-[1,3]thiazolo[5,4-c]pyridine-7-carboxamide (1.95 g, 80%) as brown oil. LC/MS (Method D, ESI): [M+H]$^+$=598.1, R$_T$=1.30 min.

N-[5-[5-chloro-2-(difluoromethoxy)phenyl]-1-[[2-(trimethylsilyl)ethoxy]-methyl]-1H-pyrazol-4-yl]-2-(methylsulfanyl)-[1,3]thiazolo[5,4-c]pyridine-7-carboxamide (1.90 g, 3.17 mmol) was treated with NH$_3$/EtOH (30 mL) and heated in a sealed vessel overnight at 100° C. The reaction mixture was cooled and concentrated under vacuum. The residue was purified by flash chromatography on silica gel (solvent gradient: 1/1-3/1 ethyl acetate/petroleum ether). The appropriate fractions were combined and concentrated under vacuum to afford 2-amino-N-[5-[5-chloro-2-(difluoromethoxy)phenyl]-1-[[2-(trimethylsilyl)ethoxy]methyl]-1H-pyrazol-4-yl]-[1,3]thiazolo[5,4-c]pyridine-7-carboxamide (950 mg, 53%) as a light yellow solid. LC/MS (Method C, ESI): [M+H]$^+$=567.2, R$_T$=1.46 min.

A solution of 2-amino-N-[5-[5-chloro-2-(difluoromethoxy)phenyl]-1-[[2-(trimethylsilyl) ethoxy]methyl]-1H-pyrazol-4-yl]-[1,3]thiazolo[5,4-c]pyridine-7-carboxamide (150 mg, 0.265 mmol) in 1,4-dioxane (10 mL) was treated with tert-butyl nitrite (140 mg, 1.35 mmol) and heated 80° C. for 1 hour. The reaction mixture was cooled and concentrated under vacuum. The residue was purified by flash chromatography on silica gel (solvent gradient: 1/2~3/2 ethyl acetate/petroleum ether). The appropriate fractions were combined and concentrated under vacuum to afford N-[5-[5-chloro-2-(difluoromethoxy)phenyl]-1-[[2-(trimethylsilyl)ethoxy]-methyl]-1H-pyrazol-4-yl]-[1,3]thiazolo[5,4-c]pyridine-7-carboxamide (110 mg, 75%) as light yellow oil. LC/MS (Method C, ESI): [M+H]$^+$=552.2, R$_T$=1.56 min.

N-[5-[5-chloro-2-(difluoromethoxy)phenyl]-1-[[2-(trimethylsilyl)-ethoxy]methyl]-1H-pyrazol-4-yl]-[1,3]thiazolo[5,4-c]pyridine-7-carboxamide (110 mg, 0.199 mmol) was treated with a solution of concentrated HCl (2.00 mL, 12 M) and methanol (4.00 mL). The resulting solution was stirred overnight at room temperature and concentrated under vacuum. DCM (5.0 mL) and DIPEA (0.50 mL) were added. The resulting mixture was concentrated under vacuum. The residue was purified by flash chromatography on silica gel (solvent: 10/1 dichloromethane/methanol). The crude product was further purified by Prep-HPLC with the following conditions: Column, XBridge Shield RP18 OBD Column, 19*150 mm, 5 um; mobile phase, Water with 10 mmol NH$_4$HCO$_3$ and MeCN (20.0% MeCN up to 50.0% in 11 min); Detector, UV 254 nm. The appropriate fractions were collected and concentrated under vacuum to afford N-[3-[5-chloro-2-(difluoromethoxy)phenyl]-1H-pyrazol-4-yl]-[1,3]thiazolo[5,4-c]pyridine-7-carboxamide (5.40 mg, 6%) as a off-white solid. LC/MS (Method A, ESI): [M+H]$^+$=422.0, R$_T$=1.69 min; $^1$H NMR (300 MHz, DMSO-d$_6$): δ 13.18 (s, 1H), 11.30 (s, 1H), 9.73 (s, 1H), 9.65 (s, 1H), 9.24 (s, 1H), 8.41 (s, 1H), 7.65 (d, J=2.7 Hz, 1H), 7.64 (dd, J=9.3, 2.7 Hz, 1H), 7.43 (d, J=9.3 Hz, 1H), 7.20 (t, J=73.5 Hz, 1H).

Example 5

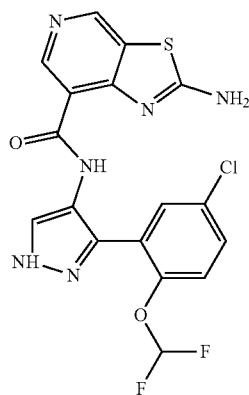 [SMILES: Nc1nc2c(C(=O)Nc3c[nH]nc3-c3cc(Cl)ccc3OC(F)F)cncc2s1]

2-amino-N-(3-(5-chloro-2-(difluoromethoxy)phenyl)-1H-pyrazol-4-yl)thiazolo[5,4-c]pyridine-7-carboxamide 2-Amino-N-[5-[5-chloro-2-(difluoromethoxy)phenyl]-1-[[2-(trimethylsilyl)ethoxy]-methyl]-1H-pyrazol-4-yl]-[1,3]thiazolo[5,4-c]pyridine-7-carboxamide (100 mg, 0.176 mmol) was treated with a solution of HCl (2.0 mL, 12 M) and methanol (4.0 mL) overnight at room temperature. The resulting mixture was concentrated under vacuum. DCM (5.0 mL) and DIPEA (0.50 mL) were added. The resulting mixture was concentrated under vacuum. The residue was purified by flash chromatography on silica gel (solvent: 10/1 dichloromethane/methanol). The appropriate fractions were combined and concentrated under vacuum. The crude product was further purified by Prep-HPLC with the following conditions: Column, XBridge Shield RP18 OBD Column, 19*150 mm, 5 um; mobile phase, Water with 10 mmol NH$_4$HCO$_3$ and MeCN (15.0% MeCN up to 50.0% in 12 min); Detector, UV 254 nm. Appropriate fractions were combined and evaporated to afford 2-amino-N-[3-[5-chloro-2-(difluoromethoxy)phenyl]-1H-pyrazol-4-yl]-[1,3]thiazolo[5,4-c]pyridine-7-carboxamide (27.2 mg, 35%) as a off-white solid. LC/MS (Method A, ESI): [M+H]$^+$=437.1, R$_T$=1.30 min; $^1$H NMR (300 MHz, DMSO-d$_6$): δ 13.14 (s, 1H), 11.02 (s, 1H), 8.90 (s, 1H), 8.88 (s, 1H), 8.20-8.17 (m, 3H), 7.62 (d, J=2.7 Hz, 1H), 7.53 (dd, J=8.8, 2.7 Hz, 1H), 7.35 (d, J=8.8 Hz, 1H), 7.05 (t, J=73.6 Hz, 1H).

Example 6

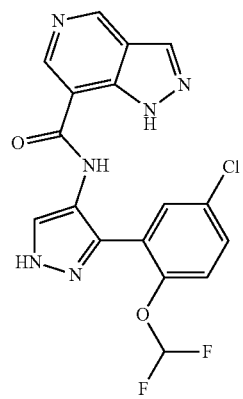 [SMILES: O=C(Nc1c[nH]nc1-c1cc(Cl)ccc1OC(F)F)c1cncc2cn[nH]c12]

Prepared using a similar method as in example 2 above. LC/MS (Method K, ESI): [M+H]$^+$=405.0, R$_T$=4.27 min; $^1$H NMR (400 MHz, DMSO-d$_6$): δ 13.63 (s, 1H), 13.30-13.04 (m, 1H), 10.44-9.98 (m, 1H), 9.22 (s, 1H), 8.86 (s, 1H), 8.39 (s, 1H), 8.19 (s, 1H), 7.69-7.45 (m, 2H), 7.37-6.86 (m, 2H).

Example 7

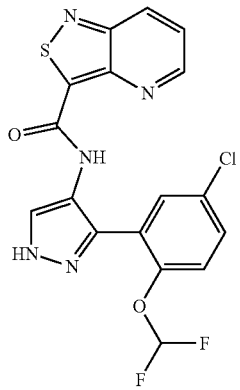 [SMILES: O=C(Nc1c[nH]nc1-c1cc(Cl)ccc1OC(F)F)c1snc2cccnc12]

N-(3-(5-chloro-2-(difluoromethoxy)phenyl)-1H-pyrazol-4-yl)isothiazolo[4,3-b]pyridine-3-carboxamide A solution of commercially available 3-bromo-[1, 2]thiazolo[4,3-b]pyridine (300 mg, 1.39 mmol), DIPEA (300 mg, 2.32 mmol), Pd(dppf)Cl$_2$.CH$_2$Cl$_2$ (114 mg, 0.140 mmol) in methanol (15 mL) was stirred at 95° C. for 5 hours under CO (10 atm) in pressure tank reactor. The reaction mixture was then allowed to cool to room temperature and concentrated under vacuum. The residue was purified by flash chromatography on silica gel (solvent: 1/3 ethyl acetate/petroleum ether). The appropriate fractions were combined and concentrated under vacuum to afford methyl [1, 2]thiazolo[4,3-b]pyridine-3-carboxylate (220 mg, 81%) as a yellow solid. LC/MS (Method D, ESI): [M+H]$^+$=195.1, R$_T$=1.13 min.

To a solution of sodium hydroxide (2.00 g, 50.0 mmol) in tetrahydrofuran (10 mL) and water (20 mL) was added methyl [1,2]thiazolo[4,3-b]pyridine-3-carboxylate (220 mg, 1.13 mmol). The resulting solution was stirred overnight at 50° C. in an oil bath and allowed to cool to room temperature. The mixture was concentrated under vacuum and the pH value of the solution was adjusted to 3 with 1 N HCl. The resulting solution was extracted with ethyl acetate (3×100 mL), the combined organic layer dried over anhydrous sodium sulfate, filtered and concentrated under vacuum to afford [1,2]thiazolo[4,3-b]pyridine-3-carboxylic acid (140 mg, 69%) as an off-white solid. LC/MS (Method D, ESI): [M+H]$^+$=181.1, R$_T$=0.85 min.

To a solution of 5-[5-chloro-2-(difluoromethoxy)phenyl]-1-[[2-(trimethylsilyl)-ethoxy]methyl]-H-pyrazol-4-amine (180 mg, 0.462 mmol) in DMA (20 mL) was added DIPEA (145 mg, 1.12 mmol), 4-dimethylaminopyridine (0.540 mg, 0.00443 mmol), [1,2]thiazolo[4,3-b]pyridine-3-carboxylic acid (80.0 mg, 0.444 mmol), PyAOP (279 mg, 0.536 mmol). The resulting solution was stirred for 5 hours at 45° C. in an oil bath. The reaction was partitioned between ice water and ethyl acetate. The organic phase was washed with brine, dried over anhydrous sodium sulfate, filtered and concentrated under vacuum. The residue was purified by flash chromatography on silica gel (solvent: ethyl acetate/petroleum ether (1/1). The appropriate fractions were combined and concentrated under vacuum to afford N-[5-[5-chloro-2-(difluoromethoxy)phenyl]-1-[[2-(trimethylsilyl)ethoxy]methyl]-1H-pyrazol-4-yl]-[1,2]thiazolo[4,3-b]pyridine-3-carboxamide (200 mg, 78%) as a light yellow solid. LC/MS (Method A, ESI): [M+H]$^+$=552.1, R$_T$=1.79 min.

N-[5-[4-chloro-2-(difluoromethoxy)phenyl]-1-[[2-(trimethylsilyl)-ethoxy]methyl]-1H-pyrazol-4-yl]-[1,2]thiazolo[4,3-b]pyridine-3-carboxamide (200 mg, 0.362 mmol) was treated with HCl/dioxane (30 ml, 4 M). The resulting solution was stirred for 2 hours at room temperature and concentrated under vacuum. The crude product (120 mg) was purified by Prep-HPLC with the following conditions: Column, X Bridge C18, 19*250 mm, 5 um; mobile phase, Mobile Phase A:Water/0.1% FA, Mobile Phase B: ACN; Flow rate: 30 mL/min; Gradient: 28% B to 53% B in 10 min; 254 nm; Detector, 254. Appropriate fractions were combined and evaporated to afford N-[3-[4-chloro-2-(difluoromethoxy)phenyl]-1H-pyrazol-4-yl]-[1,2]thiazolo[4,3-b]pyridine-3-carboxamide (46.5 mg, 30%) as a yellow solid. LC/MS (Method F, ESI): [M+H]$^+$=422.0, R$_T$=2.20 min. $^1$H NMR (300 MHz, DMSO-d$_6$): δ 13.27 (s, 1H), 10.98 (s, 1H), 8.81 (d, J=3.9 Hz, 1H), 8.46 (d, J=9.3 Hz, 1H), 8.39 (s, 1H), 7.69 (dd, J=9.3, 3.9 Hz, 1H), 7.70-7.66 (m, 2H), 7.50 (d, J=9.9 Hz, 1H), 7.23 (t, J=73.5 Hz, 1H).

Example 8

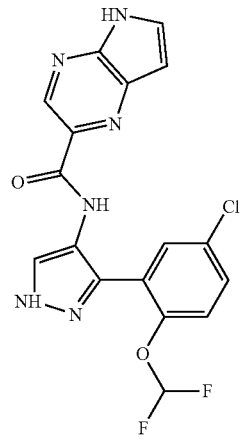 [SMILES: O=C(Nc1c[nH]nc1-c1cc(Cl)ccc1OC(F)F)c1cnc2[nH]ccc2n1]

N-(3-(5-chloro-2-(difluoromethoxy)phenyl)-1H-pyrazol-4-yl)-5H-pyrrolo[3,2-b]pyrazine-2-carboxamide To a solution of commercially available 2-bromo-5H-pyrrolo[2,3-b]pyrazine (1.00 g, 5.05 mmol) in N,N-dimethylformamide (10 mL) was added Cs$_2$CO$_3$ (2.50 g, 7.67 mmol) and [2-(chloromethoxy)ethyl]trimethylsilane (1.26 g, 7.55 mmol). The reaction mixture was stirred overnight at room temperature and concentrated under vacuum. The residue was purified by flash chromatography on silica gel (solvent: 1/10 ethyl acetate/petroleum ether). Appropriate fractions were combined and evaporated to afford 2-bromo-5-[[2-(trimethylsilyl)ethoxy]methyl]-5H-pyrrolo[2,3-b]pyrazine (1.50 g, 90%) as a yellow solid. LC/MS (Method D, ESI): [M+H]$^+$=328.0, R$_T$=1.23 min.

A solution of 2-bromo-5-[[2-(trimethylsilyl)ethoxy]methyl]-5H-pyrrolo[2,3-b]pyrazine (1.00 g, 3.04 mmol), Pd(PPh$_3$)$_2$Cl$_2$ (430 mg, 0.613 mmol), DIPEA (1.18 g, 9.13 mmol) and DMSO (10 mL) was heated at 100° C. overnight under an atmosphere of CO (10 atm). The mixture was allowed to cool to room temperature and the precipitated solid removed by filtration. The filtrate was concentrated under vacuum and the residue was purified by flash chromatography on silica gel (solvent: 2/3 ethyl acetate/petroleum ether). Appropriate fractions were combined and evaporated to afford methyl 5-[[2-(trimethylsilyl)ethoxy]methyl]-5H-pyrrolo[2,3-b]pyrazine-2-carboxylate (850 mg, 91%) as a yellow solid. LC/MS (Method A, ESI): [M+H]$^+$=308.1, R$_T$=1.64 min.

A solution of methyl 5-[[2-(trimethylsilyl)ethoxy]methyl]-5H-pyrrolo[2,3-b]pyrazine-2-carboxylate (850 mg, 2.76 mmol) in methanol (20 mL) was treated with a solution of sodium hydroxide (200 mg, 5.00 mmol) in water (10 mL). The resulting solution was stirred for 4 hours at room temperature. The pH value of the solution was adjusted to 3 with 1 N HCl. The solids were collected by filtration to afford 5-[[2-(trimethylsilyl)ethoxy]methyl]-5H-pyrrolo[2,3-b]pyrazine-2-carboxylic acid (738 mg, 91%) as a white solid. LC/MS (Method D, ESI): [M+H]$^+$=294.1, R$_T$=1.52 min.

To a solution of 5-[[2-(trimethylsilyl)ethoxy]methyl]-5H-pyrrolo[2,3-b]pyrazine-2-carboxylic acid (166 mg, 0.566 mmol) in DMA (3.0 mL) was added 5-[5-chloro-2-(difluoromethoxy)phenyl]-1-[2-(trimethylsilyl)ethoxy]methyl-1H-pyrazol-4-amine (200 mg, 0.513 mmol), DIPEA (199 mg, 1.54 mmol), 4-dimethylaminopyridine (6.30 mg, 0.0520 mmol) and PyAOP (294 mg, 0.564 mmol). The resulting solution was stirred overnight at 45° C. in an oil bath. The reaction mixture was partitioned between water and ethyl acetate. The organic layer was washed with brine, dried over anhydrous sodium sulfate, filtered and concentrated under vacuum. The residue was purified by flash chromatography on silica gel (solvent: 1/1 ethyl acetate/petroleum ether). Appropriate fractions were combined and evaporated to afford N-[5-[5-chloro-2-(difluoromethoxy)phenyl]-1-[[2-(trimethylsilyl)ethoxy]methyl]-1H-pyrazol-4-yl]-5-[[2-(trimethylsilyl)ethoxy]methyl]-5H-pyrrolo[2,3-b]pyrazine-2-carboxamide (220 mg, 64%) as a red solid. LC/MS (Method D, ESI): [M+H]$^+$=665.2, R$_T$=1.42 min.

N-[5-[5-chloro-2-(difluoromethoxy)phenyl]-1-[[2-(trimethylsilyl)ethoxy]-methyl]-1H-pyrazol-4-yl]-5-[[2-(trimethylsilyl)ethoxy]methyl]-5H-pyrrolo[2,3-b]pyrazine-2-carboxamide (220 mg, 0.331 mmol) was treated with trifluoroacetic acid (15 mL). The resulting solution was heated under reflux overnight in an oil bath and allowed to cool to room temperature. The resulting mixture was concentrated under vacuum and the pH value of the solution was adjusted to 7 with saturated aqueous NaHCO$_3$ solution. The resulting mixture was concentrated under vacuum and the residue was filtered through a short pad of silica gel (solvent: 2/3 ethyl acetate/petroleum ether). The crude product was purified by Prep-HPLC with the following conditions: Column, XBridge Prep C18 OBD Column, 19*150 mm, 5 um; mobile phase, water with 0.05% FA and MeCN (40.0% up to 51.0% in 10 min, up to 95.0% in 1 min, hold 95.0% in 1 min, down to 40.0% in 2 min); Detector, UV 254/220 nm. Appropriate fractions were combined and evaporated to afford N-[3-[5-chloro-2-(difluoromethoxy)phenyl]-1H-pyrazol-4-yl]-5H-pyrrolo[2,3-b]pyrazine-2-carboxamide (8.90 mg, 7%) as a white solid. LC/MS (Method B, ESI): [M+H]$^+$=405.0, R$_T$=2.00 min. $^1$H NMR (300 MHz, DMSO-d$_6$): δ 13.20 (s, 1H), 12.51 (s, 1H), 10.10 (s, 1H), 8.94 (s, 1H), 8.29 (s, 1H), 8.09 (d, J=3.9 Hz, 1H), 7.66 (d, J=2.7 Hz, 1H), 7.59 (dd, J=8.7, 2.7 Hz, 1H), 7.41 (d, J=8.7 Hz, 1H), 7.29 (t, J=73.2 Hz, 1H), 6.71 (d, J=3.9 Hz, 1H).

Example 9

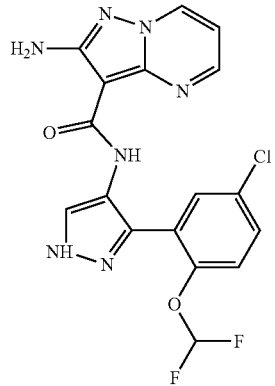 [SMILES: Nc1nn2cccnc2c1C(=O)Nc1c[nH]nc1-c1cc(Cl)ccc1OC(F)F]

2-amino-N-(3-(5-chloro-2-(difluoromethoxy)phenyl)-1H-pyrazol-4-yl)pyrazolo[1,5-a]pyrimidine-3-carboxamide tert-Butyl N-[3-([3-[5-chloro-2-(difluoromethoxy)phenyl]-1H-pyrazol-4-yl]carbamoyl)pyrazolo[1,5-a]pyrimidin-2-yl]carbamate (100 mg, 0.192 mmol) was treated with trifluoroacetic acid (4.0 mL) in dichloromethane (4.0 mL). The resulting solution was stirred overnight at room temperature and concentrated under vacuum. DCM (5.00 mL) and DIPEA (0.50 mL) were added. The resulting mixture was concentrated under vacuum. The crude product was purified by Prep-HPLC with the following conditions: Column, XBridge Shield RP18 OBD Column, 19*150 mm, 5 um; mobile phase, Water with 10 mmol NH$_4$HCO$_3$ and MeCN (15.0% MeCN up to 55.0% in 12 min); Detector, UV 254 nm. Appropriate fractions were combined and evaporated to afford 2-amino-N-[3-[5-chloro-2-(difluoromethoxy)phenyl]-1H-pyrazol-4-yl]pyrazolo[1,5-a]pyrimidine-3-carboxamide (40.3 mg, 50%) as a light yellow solid. LC/MS (Method E, ESI): [M+H]$^+$=420.0, R$_T$=2.76 min. $^1$H NMR (300 MHz, DMSO-d$_6$): δ 13.03 (s, 1H), 9.54 (s, 1H), 8.94 (d, J=6.6 Hz, 1H), 8.36 (d, J=4.8 Hz, 1H), 8.26 (s, 1H), 7.68-7.61 (m, 2H), 7.46 (d, J=8.7 Hz, 1H), 7.25 (t, J=73.2 Hz, 1H), 7.00 (dd, J=6.6 Hz, 4.8 Hz, 1H), 6.56 (s, 2H).

Example 10

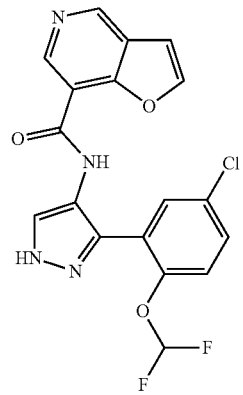 [SMILES: O=C(Nc1c[nH]nc1-c1cc(Cl)ccc1OC(F)F)c1cncc2ccoc12]

N-(3-(5-chloro-2-(difluoromethoxy)phenyl)-1H-pyrazol-4-yl)furo[3,2-c]pyridine-7-carboxamide A solution of 7-bromofuro[3,2-c]pyridine (500 mg, 2.52 mmol), Pd(OAc)$_2$ (56.0 mg, 0.249 mmol), XantPhos (290 mg, 0.501 mmol) and DIPEA (1.63 g, 12.6 mmol) in methanol (2.0 mL) and toluene (6.0 mL) was stirred at 100° C. overnight under an atmosphere of CO (10 atm). The resulting mixture was allowed to cool to room temperature and concentrated under vacuum. The residue was purified by flash chromatography on silica gel (solvent: 1/1 ethyl acetate/petroleum ether). The appropriate fractions were combined and concentrated under vacuum to afford methyl furo[3,2-c]pyridine-7-carboxylate (260 mg, 58%) as a yellow solid. TLC: $R_f$=0.4; PE/EA=1/1.

A solution of methyl furo[3,2-c]pyridine-7-carboxylate (250 mg, 1.41 mmol) in tetrahydrofuran (2.0 mL) was treated with LiOH (68.0 mg, 2.83 mmol) in water (1.0 mL). The resulting solution was stirred for 2 hours at room temperature. The pH value of the solution was adjusted to 3 with 1 N HCl. The resulting mixture was concentrated under vacuum to afford furo[3,2-c]pyridine-7-carboxylic acid (200 mg, 87%) as colorless oil. TLC: $R_f$=0.3; DCM/MeOH=10/1.

A solution of furo[3,2-c]pyridine-7-carboxylic acid (83.0 mg, 0.509 mmol), 4-dimethylaminopyridine (3.00 mg, 0.0250 mmol), DIPEA (101 mg, 0.781 mmol), PyAOP (266 mg, 0.510 mmol) and 5-[5-chloro-2-(difluoromethoxy)phenyl]-1-[2-(trimethylsilyl)ethoxy]methyl-TH-pyrazol-4-amine (100 mg, 0.256 mmol) in N,N-dimethylformamide (2.0 mL) was stirred at 60° C. for 2 hours. The resulting mixture was concentrated under vacuum and the residue was purified by flash chromatography on silica gel (solvent: 9/1 dichloromethane/methanol). The appropriate fractions were combined and concentrated under vacuum to afford N-[5-[5-chloro-2-(difluoromethoxy)phenyl]-1-[[2-(trimethylsilyl)ethoxy]methyl]-1H-pyrazol-4-yl]furo[3,2-c]pyridine-7-carboxamide (80 mg, 29%) as brown oil. TLC: $R_f$=0.4; DCM/MeOH=5/1.

N-[5-[5-chloro-2-(difluoromethoxy)phenyl]-1-[[2-(trimethylsilyl)-ethoxy]methyl]-1H-pyrazol-4-yl]furo[3,2-c]pyridine-7-carboxamide (80.0 mg, 0.150 mmol) was treated with trifluoroacetic acid (1.0 mL) in dichloromethane (2.0 mL). The resulting solution was stirred at room temperature for 2 hours and concentrated under vacuum. The crude product was purified by Prep-HPLC with the following conditions: Column, XBridge Prep C18 OBD Column, 19*150 mm, 5 um; mobile phase, Water (0.05% NH$_3$H$_2$O) and ACN (40% ACN up to 70% in 7 min); Detector, UV 254, 220 nm. Appropriate fractions were combined and evaporated to afford N-[3-[5-chloro-2-(difluoromethoxy)phenyl]-1H-pyrazol-4-yl]furo[3,2-c]pyridine-7-carboxamide (7.2 mg, 12%) as a white solid. LC/MS (Method G, ESI): [M+H]$^+$=405.1, $R_T$=2.84 min; $^1$H NMR (300 MHz, DMSO-d$_6$): δ 13.20 (s, 1H), 9.83 (s, 1H), 9.10 (s, 1H), 8.78 (s, 1H), 8.28 (s, 1H), 8.18 (d, J=2.4 Hz, 1H), 7.64 (d, J=2.8 Hz, 1H), 7.57 (dd, J=8.8, 2.8 Hz, 1H), 7.36 (d, J=8.8 Hz, 1H), 7.24 (d, J=2.4 Hz, 1H), 7.16 (t, J=73.6 Hz, 1H).

Example 11

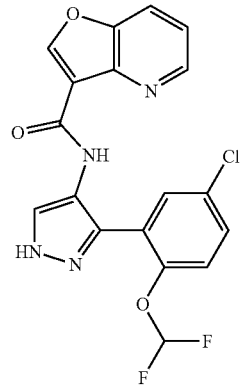 [SMILES: O=C(Nc1c[nH]nc1-c1cc(Cl)ccc1OC(F)F)c1coc2cccnc12]

N-(3-(5-chloro-2-(difluoromethoxy)phenyl)-1H-pyrazol-4-yl)furo[3,2-b]pyridine-3-carboxamide A solution of 3-bromofuro[3,2-b]pyridine (700 mg, 3.53 mmol), Pd(OAc)$_2$ (79.0 mg, 0.352 mmol), Xantphos (405 mg, 0.700 mmol) and DIPEA (2.28 g, 17.6 mmol) in methanol (15 mL) and toluene (45 mL) was stirred at 100° C. for 48 hours under an atmosphere of CO (20 atm). The resulting mixture was allowed to cool to room temperature and concentrated under vacuum. The residue was purified by flash chromatography on silica gel (solvent: 95/5 dichloromethane/methanol). The appropriate fractions were combined and concentrated under vacuum to afford methyl furo[3,2-b]pyridine-3-carboxylate (300 mg, 48%) as a white solid. TLC: $R_f$=0.4, EA/Hex=1/1.

A solution of methyl furo[3,2-b]pyridine-3-carboxylate (170 mg, 0.960 mmol) in tetrahydrofuran (2.00 mL) was treated with LiOH (35.0 mg, 1.46 mmol) in water (1.00 mL). The resulting solution was stirred at room temperature for 2 hours. The pH value of the solution was adjusted to 3 with 1 N HCl. The resulting mixture was concentrated under vacuum to afford furo[3,2-b]pyridine-3-carboxylic acid (150 mg, 96%) as a white solid. TLC: $R_f$=0.2; DCM/MeOH=5/1.

A solution of furo[3,2-b]pyridine-3-carboxylic acid (128 mg, 0.785 mmol), 4-dimethylaminopyridine (6.00 mg, 0.0490 mmol), DIPEA (303 mg, 2.34 mmol), PyAOP (532 mg, 1.02 mmol), 5-[5-chloro-2-(difluoromethoxy)phenyl]-1-[2-(trimethylsilyl)ethoxy]methyl-1H-pyrazol-4-amine (200 mg, 0.513 mmol) in N,N-dimethylformamide (4.0 mL) was stirred at 60° C. for 2 hours. The resulting mixture was concentrated under vacuum and the residue was purified by flash chromatography on silica gel (solvent: 95/5 dichloromethane/methanol). The appropriate fractions were combined and concentrated under vacuum to afford N-[5-[5-chloro-2-(difluoromethoxy)phenyl]-1-[[2-(trimethylsilyl)ethoxy]methyl]-1H-pyrazol-4-yl]furo[3,2-b]pyridine-3-carboxamide (190 mg (45%) as yellow oil. TLC: $R_f$=0.3; DCM/MeOH=10/1.

N-[5-[5-chloro-2-(difluoromethoxy)phenyl]-1-[[2-(trimethylsilyl)-ethoxy]methyl]-1H-pyrazol-4-yl]furo[3,2-b]pyridine-3-carboxamide (190 mg, 0.355 mmol) was treated with trifluoroacetic acid (1.0 mL) in dichloromethane (4.0 mL). The resulting solution was stirred at room temperature for 2 hours and concentrated under vacuum. The crude product was purified by Prep-HPLC with the following conditions: Column, XBridge Prep C18 OBD Column, 19*150 mm, 5 um; mobile phase, Water (0.05% NH₃H₂O) and ACN (40% ACN up to 70% in 7 min); Detector, UV 254, 220 nm. Appropriate fractions were combined and evaporated to afford N-[3-[5-chloro-2-(difluoromethoxy)phenyl]-1H-pyrazol-4-yl]furo[3,2-b]pyridine-3-carboxamide (32.7 mg, 23%) as a white solid. LC/MS (Method H, ESI): [M+H]⁺=405.1, $R_T$=1.80 min; ¹H NMR (300 MHz, DMSO-d₆): δ 13.20 (s, 1H), 10.40 (s, 1H), 8.99 (s, 1H), 8.50 (dd, J=4.4, 1.2 Hz, 1H), 8.34 (s, 1H), 8.25 (dd, J=8.4, 1.2 Hz, 1H), 7.66 (dd, J=8.8, 2.8 Hz, 1H), 7.63 (d, J=2.8 Hz, 1H), 7.52 (dd, J=8.4, 4.4 Hz, 1H), 7.48 (d, J=8.8 Hz, 1H), 7.22 (t, J=73.2 Hz, 1H).

Example 12

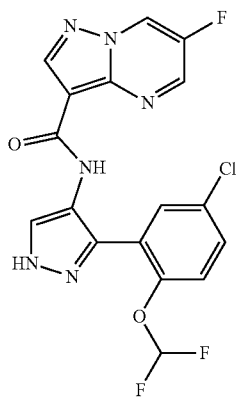 [SMILES: O=C(Nc1c[nH]nc1-c1cc(Cl)ccc1OC(F)F)c1cnn2cc(F)cnc12]

N-(3-(5-chloro-2-(difluoromethoxy)phenyl)-1H-pyrazol-4-yl)-6-fluoropyrazolo[1,5-a]pyrimidine-3-carboxamide A solution of (2Z)-3-(diethylamino)-2-fluoro-2-propenal (326 mg, 2.25 mmol-synthesised according to the literature procedure: K. Funabiki, T. Ohtsuki, T. Ishihara and. Yamanaka, Chem. Lett., 1994, 1075-78.) and ethyl 3-amino-1H-pyrazole-4-carboxylate (698 mg, 4.50 mmol) in acetic acid (6 ml) was heated under reflux for 4 h. The mixture was allowed to cool to room temperature and concentrated under vacuum afford a pale yellow solid. The resultant residue was treated with 2M aqueous NaOH (15 ml) then extracted with DCM. The organic layer was dried over anhydrous sodium sulfate, filtered and evaporated. The residue was purified by flash chromatography on silica gel (solvent gradient: 0-50% ethyl acetate in pentane). Appropriate fractions were combined and evaporated to afford ethyl 6-fluoropyrazolo[1,5-a]pyrimidine-3-carboxylate (24 mg, 5%) as a pale yellow solid. LC/MS (Method K, ESI): [M+H]⁺=325, $R_T$=3.89 min; ¹H NMR (400 MHz, CDCl₃): δ 8.82 (d, J=2.7 Hz, 1H), 8.72 (dd, J=3.6, 2.7 Hz, 1H), 8.60 (s, 1H), 4.45 (q, J=7.1 Hz, 2H), 4.45 (q, J=7.1 Hz, 2H), 1.42 (t, J=7.1 Hz, 3H).

A suspension of ethyl 6-fluoropyrazolo[1,5-a]pyrimidine-3-carboxylate (54 mg, 0.26 mmol) and 1M aqueous lithium hydroxide solution (290 μl, 0.29 mmol) in IMS (1.5 ml) was stirred at room temperature for 4 days. The reaction mixture was treated with 1N HCl (20 ml) and extracte with ethyl acetate (3×25 mL). The combined organic layer was washed with brine, dried over anhydrous sodium sulfate, filtered and evaporated to afford 6-fluoropyrazolo[1,5-a]pyrimidine-3-carboxylic acid (40 mg, 68%) as a yellow powder. This crude material was used directly in the subsequent reaction.

A solution 6-fluoropyrazolo[1,5-a]pyrimidine-3-carboxylic acid (40 mg, 0.17 mmol), DIPEA (89 μl, 0.51 mmol), HATU (76 mg, 0.20 mmol) and 5-[5-chloro-2-(difluoromethoxy)phenyl]-1-[2-(trimethylsilyl)-ethoxy]methyl-1H-pyrazol-4-amine (71 mg, 0.18 mmol) in N,N-dimethylformamide (3.0 mL) was stirred at room temperature for 20 hours. The resulting mixture was concentrated under vacuum. The residue was diluted with ethyl acetate and washed with brine (×3), dried over anhydrous sodium sulfate, filtered and evaporated. The residue was purified by flash chromatography on silica gel (solvent gradient: ethyl acetate in pentane (0-50%). The appropriate fractions were combined and concentrated under vacuum to afford N-(5-(5-chloro-2-(difluoromethoxy)phenyl)-1-((2-(trimethylsilyl)ethoxy)methyl)-1H-pyrazol-4-yl)-6-fluoropyrazolo[1,5-a]pyrimidine-3-carboxamide (30 mg, 32%) as yellow oil. LC/MS (Method K, ESI): [M+H]⁺=553.0, $R_T$=4.24 min; ¹H NMR (400 MHz, CDCl₃): δ 9.42-9.39 (m, 1H), 8.78-8.73 (m, 2H), 8.57-8.56 (m, 1H), 8.34-8.33 (m, 1H), 7.65-7.64 (m, 1H), 7.55-7.51 (m, 1H), 7.38-7.35 (m, 1H), 6.43 (t, J=71.5 Hz, 1H), 5.47-5.33 (m, 2H), 3.68-3.54 (m, 2H), 1.31-1.26 (m, 3H), 0.93-0.84 (m, 4H).

To a solution of N-(5-(5-chloro-2-(difluoromethoxy)phenyl)-1-((2-(trimethylsilyl)ethoxy)methyl)-1H-pyrazol-4-yl)-6-fluoropyrazolo[1,5-a]pyrimidine-3-carboxamide (30 mg, 0.05 mmol) in IMS (10 mL) was added HCl (6N, 1 mL) and the reaction mixture heated at 70° C. for 19 hours. The reaction mixture was allowed to cool to room temperature and concentrated in vacuo. The solid residue was purified by flash chromatography on silica gel (solvent gradient: 0-50% ethyl acetate in pentane). The appropriate fractions were combined and concentrated under vacuum to afford N-(3-(5-chloro-2-(difluoromethoxy)phenyl)-1H-pyrazol-4-yl)-6-fluoro-pyrazolo[1,5-a]pyrimidine-3-carboxamide (17 mg, 80%) as an off-white solid. LC/MS (Method I, ESI): [M+H]⁺=422.9, $R_T$=3.89 min; ¹H NMR (400 MHz, DMSO-d₆): δ 13.13 (s, 1H), 9.84-9.80 (m, 1H), 9.56 (s, 1H), 8.94 (d, J=2.3 Hz, 1H), 8.70 (s, 1H), 8.29 (s, 1H), 7.68-7.60 (m, 2H), 7.52-7.43 (m, 1H), 7.27 (t, J=72.8 Hz, 1H)

Example 13

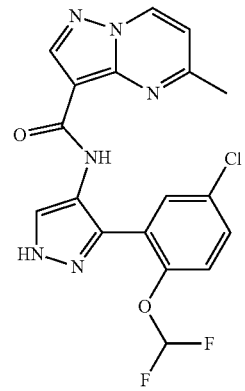 [SMILES: Cc1ccn2ncc(C(=O)Nc3c[nH]nc3-c3cc(Cl)ccc3OC(F)F)c2n1]

N-(3-(5-chloro-2-(difluoromethoxy)phenyl)-1H-pyrazol-4-yl)-5-methylpyrazolo[1,5-a]pyrimidine-3-carboxamide Prepared using a similar method as in example 12 above. LC/MS (Method I, ESI): [M+H]⁺=419.0, $R_T$=3.80 min; ¹H NMR (400 MHz, DMSO-$d_6$): δ 13.05 (s, 1H), 10.44-9.70 (s, 1H), 9.16 (d, J=7.0 Hz, 1H), 8.56 (s, 1H), 8.32 (s, 1H), 7.68-7.60 (m, 2H), 7.48-7.42 (m, 1H), 7.15 (d, J=Hz, 1H), 7.09 (t, J=73.4 Hz, 1H), 2.42 (s, 3H).

Example 14

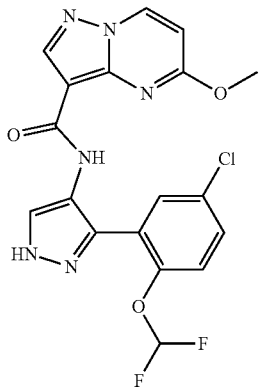 [SMILES: COc1ccn2ncc(C(=O)Nc3c[nH]nc3-c3cc(Cl)ccc3OC(F)F)c2n1]

N-(3-(5-chloro-2-(difluoromethoxy)phenyl)-1H-pyrazol-4-yl)-5-methoxypyrazolo[1,5-a]pyrimidine-3-carboxamide Prepared using a similar method as in example 12 above. LC/MS (Method I, ESI): [M+H]$^+$=435.0, $R_T$=3.84 min; $^1$H NMR (400 MHz, DMSO-$d_6$): δ 13.05 (s, 1H), 9.05 (d, J=7.7 Hz, 1H), 8.96 (s, 1H), 8.45 (s, 1H), 8.26 (s, 1H), 7.64-7.57 (m, 2H), 7.38-7.34 (m, 1H), 7.08 (t, J=73.4 Hz, 1H), 6.72 (d, J=7.5 Hz, 1H), 3.46 (s, 3H).

Example 15

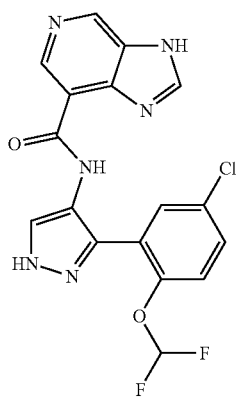 [SMILES: O=C(Nc1c[nH]nc1-c1cc(Cl)ccc1OC(F)F)c1cncc2[nH]cnc12]

N-(3-(5-chloro-2-(difluoromethoxy)phenyl)-1H-pyrazol-4-yl)-3H-imidazo[4,5-c]pyridine-7-carboxamide Prepared using a similar method as in example 12 above. LC/MS (Method I, ESI): [M+H]$^+$=405.1, $R_T$=3.74 min; $^1$H NMR (400 MHz, DMSO-$d_6$) δ 13.48 (s, 1H), 11.12 (s, 1H), 9.06 (s, 1H), 8.93 (s, 1H), 8.61 (s, 1H), 8.37 (s, 1H), 7.49 (dd, J=8.8, 2.7 Hz, 1H), 7.38 (d, J=2.7 Hz, 1H), 7.22 (d, J=8.9 Hz, 1H), 3.92 (s, 3H), 3.76 (s, 3H).

JAK Enzyme Assays were Carried Out as Follows:

The activity of the isolated recombinant JAK1 and JAK2 kinase domain was measured by monitoring phosphorylation of a peptide derived from JAK3 (Val-Ala-Leu-Val-Asp-Gly-Tyr-Phe-Arg-Leu-Thr-Thr, fluorescently labeled on the N-terminus with 5-carboxyfluorescein) using the Caliper LabChip® technology (Caliper Life Sciences, Hopkinton, Mass.). To determine inhibition constants ($K_i$), compounds were diluted serially in DMSO and added to 50 µL kinase reactions containing purified enzyme (1.5 nM JAK1, or 0.2 nM JAK2), 100 mM HEPES buffer (pH 7.2), 0.015% Brij-35, 1.5 µM peptide substrate, ATP (25 µM), 10 mM $MgCl_2$, 4 mM DTT at a final DMSO concentration of 2%. Reactions were incubated at 22° C. in 384-well polypropylene microtiter plates for 30 minutes and then stopped by addition of 25 µL of an EDTA containing solution (100 mM HEPES buffer (pH 7.2), 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip® 3000 according to the manufacturer's specifications. $K_i$ values were then determined using the Morrison tight binding model (Morrison, J. F., Biochim. Biophys. Acta. 185:269-296 (1969); William, J. W. and Morrison, J. F., Meth. Enzymol., 63:437-467 (1979)) modified for ATP-competitive inhibition $[K_i=K_{i,app}/(1+[ATP]/K_{m,app})]$.

JAK1 Pathway Assay in Cell Lines was Carried Out as Follows:

Inhibitor potency ($EC_{50}$) was determined in cell-based assays designed to measure JAK1 dependent STAT phosphorylation. As noted above, inhibition of IL-4, IL-13, and IL-9 signalling by blocking the Jak/Stat signaling pathway can alleviate asthmatic symptoms in pre-clinical lung inflammation models (Mathew et al., 2001, J Exp Med 193(9): 1087-1096; Kudlacz et. al., 2008, Eur J. Pharmacol 582(1-3): 154-161).

In one assay approach, TF-1 human erythroleukemia cells obtained from the American Type Culture Collection (ATCC; Manassas, Va.) were used to measure JAK1-dependent STAT6 phosphorylation downstream of IL-13 stimulation. Prior to use in the assays, TF-1 cells were starved of GM-CSF overnight in OptiMEM medium (Life Technologies, Grand Island, N.Y.) supplemented with 0.5% charcoal/dextran stripped fetal bovine serum (FBS), 0.1 mM non-essential amino acids (NEAA), and 1 mM sodium pyruvate. The assays were run in 384-well plates in serum-free OptiMEM medium using 300,000 cells per well. In a second assay approach, BEAS-2B human bronchial epithelial cells obtained from ATCC were plated at 100,000 cells per well of a 96-well plate one day prior to the experiment. The BEAS-2B assay was run in complete growth medium (bronchial epithelial basal medium plus bulletkit; Lonza; Basel, Switzerland).

Test compounds were serially diluted 1:2 in DMSO and then diluted 1:50 in medium just before use. Diluted compounds were added to the cells, for a final DMSO concentration of 0.2%, and incubated for 30 min (for the TF-1 assay) or 1 hr (for the BEAS-2B assay) at 37° C. Then, cells were stimulated with human recombinant cytokine at their respective $EC_{90}$ concentrations, as previously determined for each individual lot. Cells were stimulated with IL-13 (R&D Systems, Minneapolis, Minn.) for 15 min at 37° C. The TF-1 cell reactions were stopped by the direct addition of 10× lysis buffer (Cell Signaling Technologies, Danvers, Mass.), whereas the BEAS-2B cell incubations were halted by the removal of medium and addition of 1× lysis buffer.

The resultant samples were frozen in the plates at −80° C. Compound mediated inhibition of STAT6 phosphorylation was measured in the cell lysates using MesoScale Discovery (MSD) technology (Gaithersburg, Md.). $EC_{50}$ values were determined as the concentration of compound required for 50% inhibition of STAT phosphorylation relative to that measured for the DMSO control.

Table 2 provides JAK1 $K_i$, JAK2 $K_i$ and IL-13-pSTAT6 $IC_{50}$ information for the noted Examples.

TABLE 2

| Example number | JAK1 Ki (µM) | JAK2 Ki (µM) | IL-13-pSTAT6 IC50 (µM) |
| --- | --- | --- | --- |
| 1 | 0.00363 | 0.00366 | 0.0928 |
| 2 | 0.00135 | 0.00035 | 0.0359 |
| 3 | 0.00655 | 0.00096 | |
| 4 | 0.00950 | 0.00202 | |
| 5 | 0.00097 | 0.00006 | |
| 6 | 0.00735 | 0.00048 | |
| 7 | 0.00054 | 0.00060 | 0.0202 |
| 8 | 0.00057 | 0.00034 | |
| 9 | 0.00049 | 0.00017 | 0.0079 |
| 10 | 0.00085 | 0.00033 | 0.0506 |
| 11 | 0.00056 | 0.00049 | 0.0175 |
| 12 | 0.00041 | 0.00009 | 0.0168 |
| 13 | 0.00229 | 0.00041 | 0.0415 |
| 14 | 0.00018 | 0.00004 | 0.0038 |
| 15 | 0.00567 | 0.00255 | |

What is claimed is:

1. A compound selected from the group consisting of:

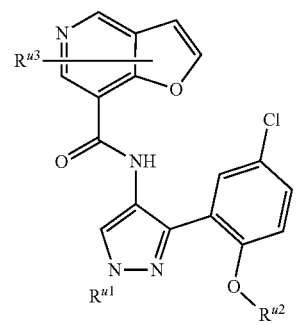

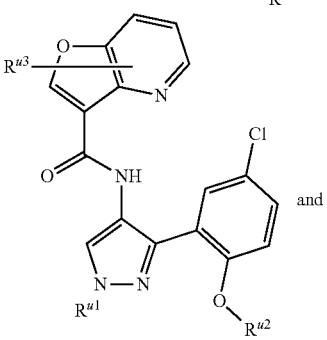

and

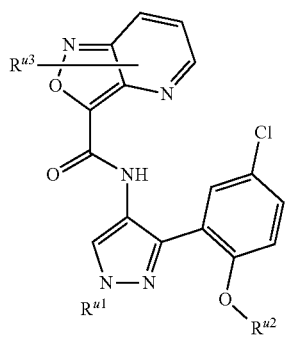

wherein:

$R^{u1}$ is H or methyl;

$R^{u2}$ is methyl or difluoromethyl; and $R^{u3}$ is hydrogen, methyl, methoxy, halo, or $NH_2$;

or a pharmaceutically acceptable salt thereof.

2. The compound of claim 1, selected from the group consisting of:

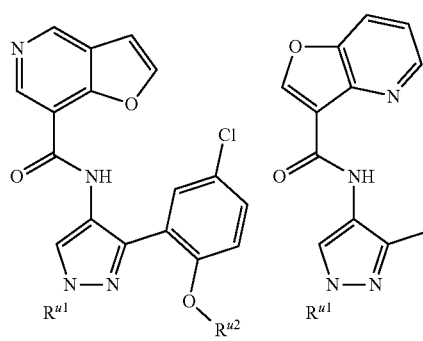

and

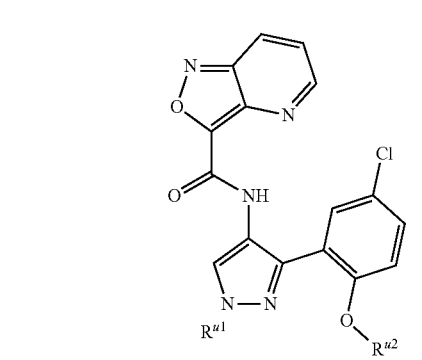

wherein:

$R^{u1}$ is H or methyl; and $R^{u2}$ is methyl or difluoromethyl;

or a pharmaceutically acceptable salt thereof.

3. A pharmaceutical composition comprising a compound of claim 1 or a pharmaceutically acceptable salt thereof, and a pharmaceutically acceptable excipient.

4. The compound of claim 2, selected from the group consisting of:
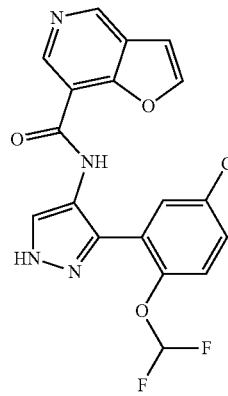 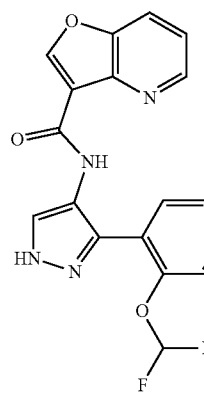 and
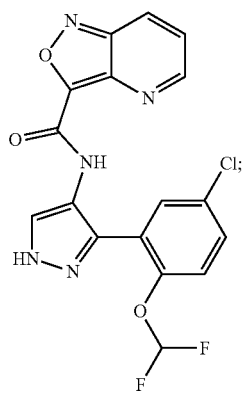
or a pharmaceutically acceptable salt thereof.
* * * * *